US008690808B2

(12) United States Patent
Reiley et al.

(10) Patent No.: US 8,690,808 B2
(45) Date of Patent: Apr. 8, 2014

(54) SYSTEMS, DEVICES, AND METHODS FOR MECHANICALLY REDUCING AND FIXING BONE FRACTURES

(75) Inventors: Mark A. Reiley, Washington, DC (US); James C. Colin, Walnut Creek, CA (US); Mattew Thompson, Corte Madera, CA (US); Kurt Vedder, Danville, CA (US)

(73) Assignee: Fixes 4 Kids Inc., Salt Lake City, UT (US)

( * ) Notice: Subject to any disclaimer, the term of this patent is extended or adjusted under 35 U.S.C. 154(b) by 291 days.

(21) Appl. No.: 13/051,774

(22) Filed: Mar. 18, 2011

(65) Prior Publication Data

US 2012/0071802 A1    Mar. 22, 2012

Related U.S. Application Data

(60) Provisional application No. 61/443,080, filed on Feb. 15, 2011, provisional application No. 61/396,562, filed on May 28, 2010.

(51) Int. Cl.
*A61F 5/00* (2006.01)
(52) U.S. Cl.
USPC ............... 602/16; 602/23; 602/32; 602/39
(58) Field of Classification Search
USPC ............. 602/5, 16, 20–28, 39, 32; 606/54, 57
See application file for complete search history.

(56) References Cited

U.S. PATENT DOCUMENTS

| | | | |
|---|---|---|---|
| 5,546,942 A * | 8/1996 | Zhang | 600/427 |
| 6,001,097 A * | 12/1999 | Campopiano et al. | 606/57 |
| 6,283,964 B1 * | 9/2001 | Weiner | 606/55 |
| 6,328,737 B1 | 12/2001 | Moorcroft | |
| 7,479,142 B2 | 1/2009 | Weiner et al. | |
| 2009/0149855 A1 | 6/2009 | Iwaki | |

OTHER PUBLICATIONS

International Preliminary Report on Patentability, PCT/US11/37732, dated May 2, 2012.
Search Report/Written Opinion dated Sep. 6, 2011, in International Patent Application Serial No. PCT/US2011/037732.

* cited by examiner

*Primary Examiner* — Michael A. Brown
(74) *Attorney, Agent, or Firm* — Ryan Kromholz & Manion, S.C.

(57) ABSTRACT

A fracture reduction is mechanically achieved by supporting a body region having the bone fracture on a frame. A first reduction mechanism on the frame is operated to apply to the bone fracture a first predefined force reduction vector that returns the bone fracture to a corrective alignment in a first anatomic orientation, while also mechanically maintaining the corrective alignment in the first anatomic orientation. Independently, a second reduction mechanism on the frame is operated to apply a second predefined force reduction vector that returns the bone fracture to a corrective alignment in a second anatomic orientation different than the first anatomic orientation without altering the corrective alignment in the first anatomic orientation, while mechanically maintaining the corrective alignment in the second anatomic orientation. The fracture reduction is mechanically fixed by mechanically guiding the placement at least one bone fixing device into the reduced bone fracture.

40 Claims, 62 Drawing Sheets

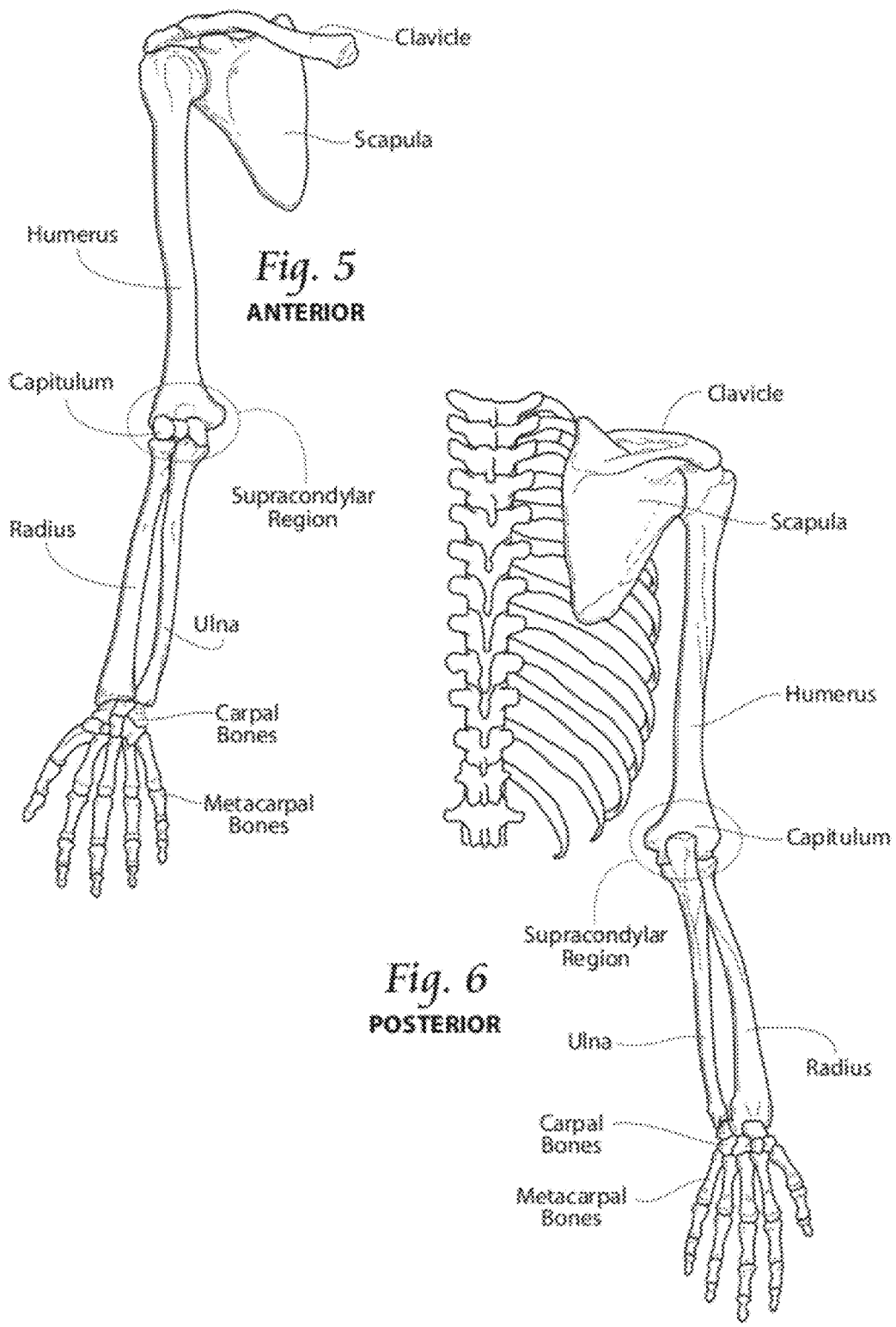

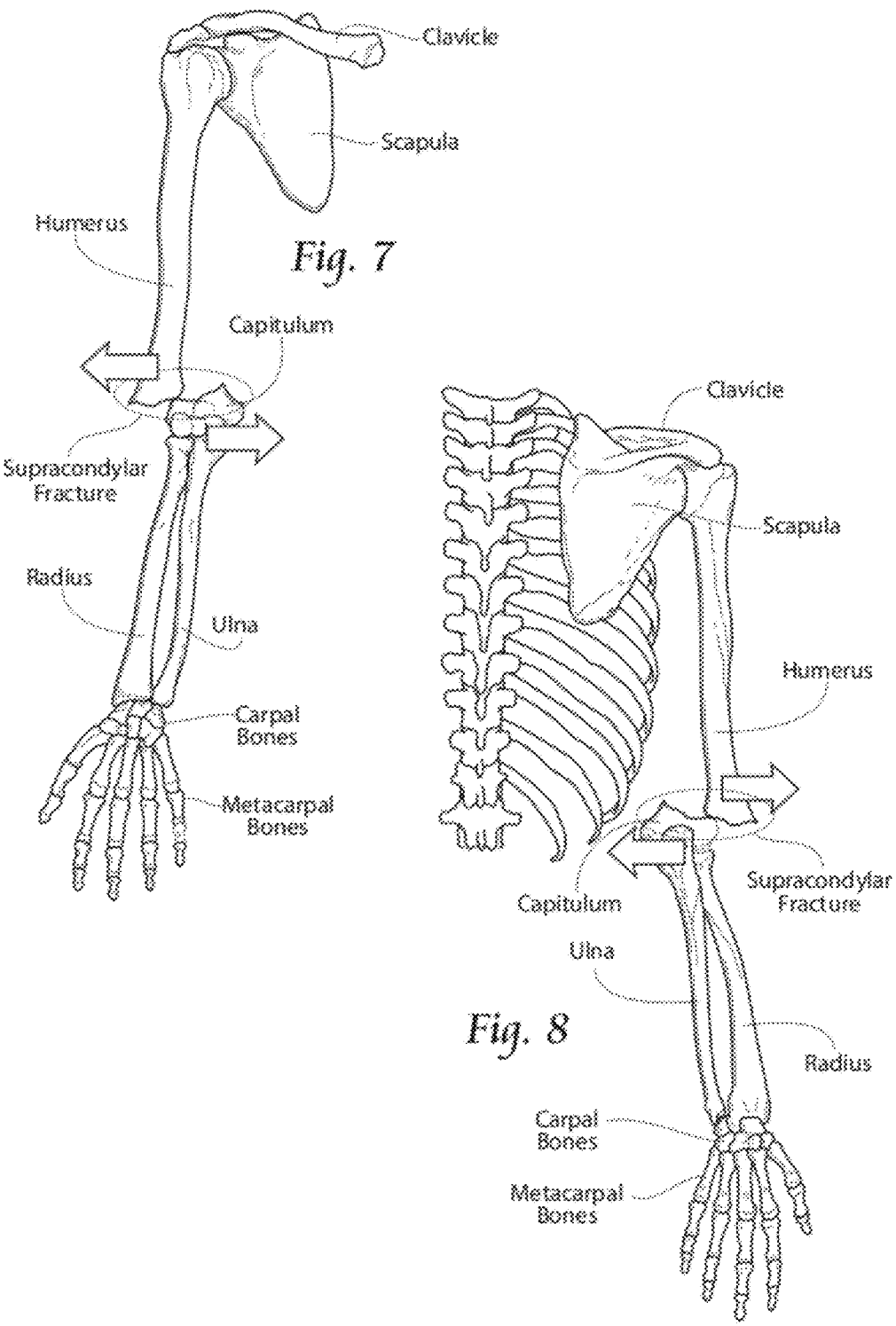

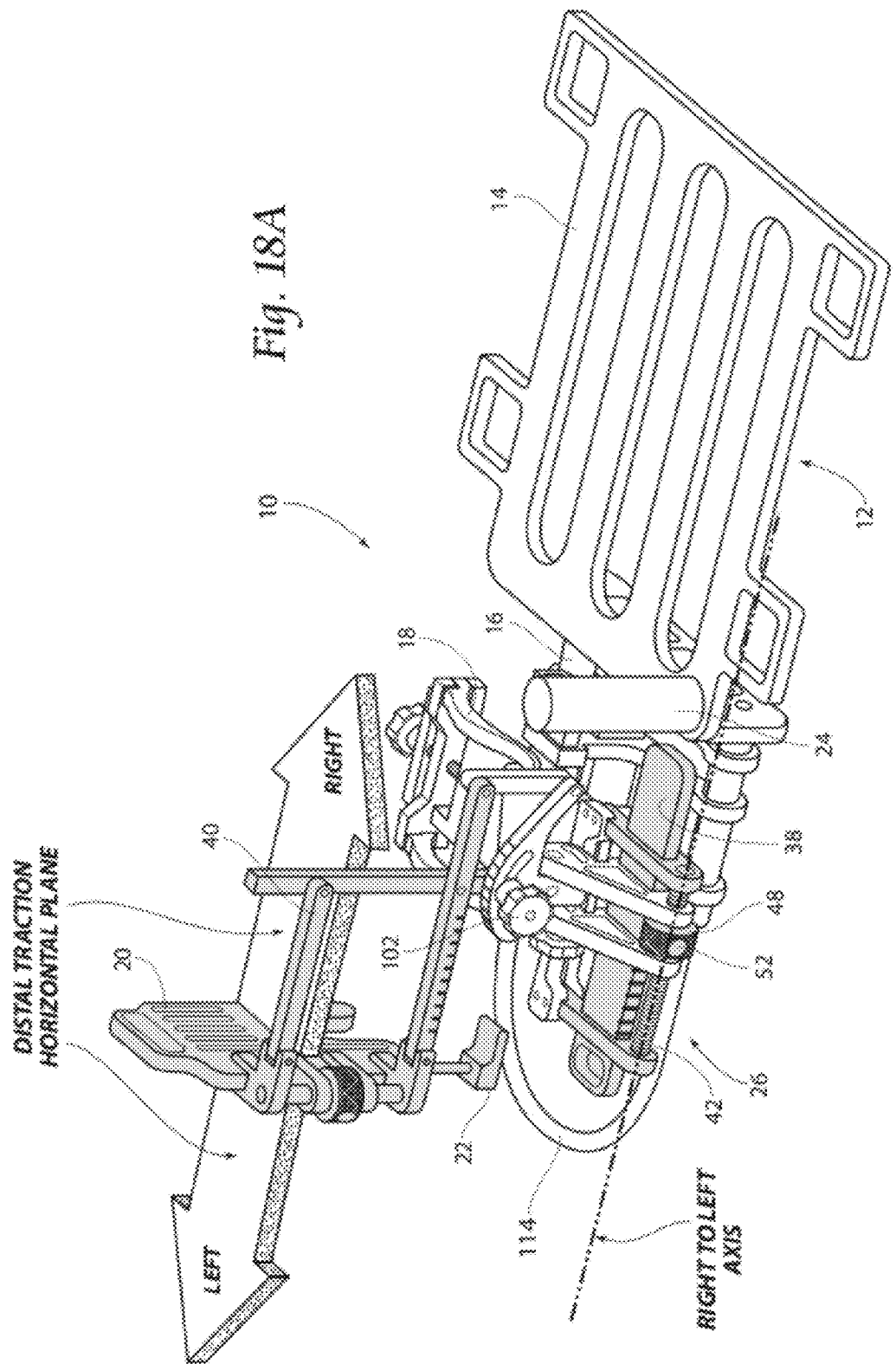

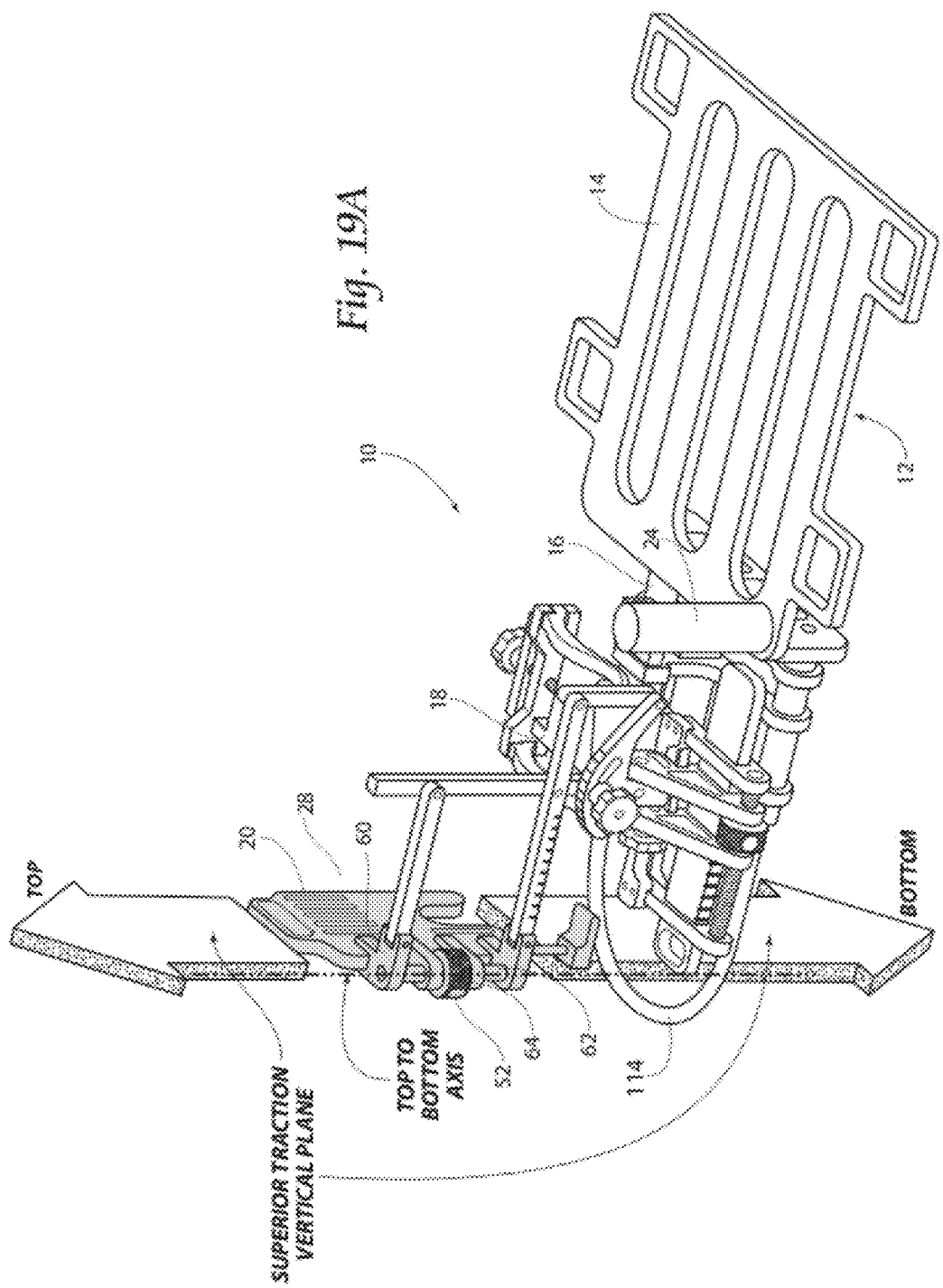

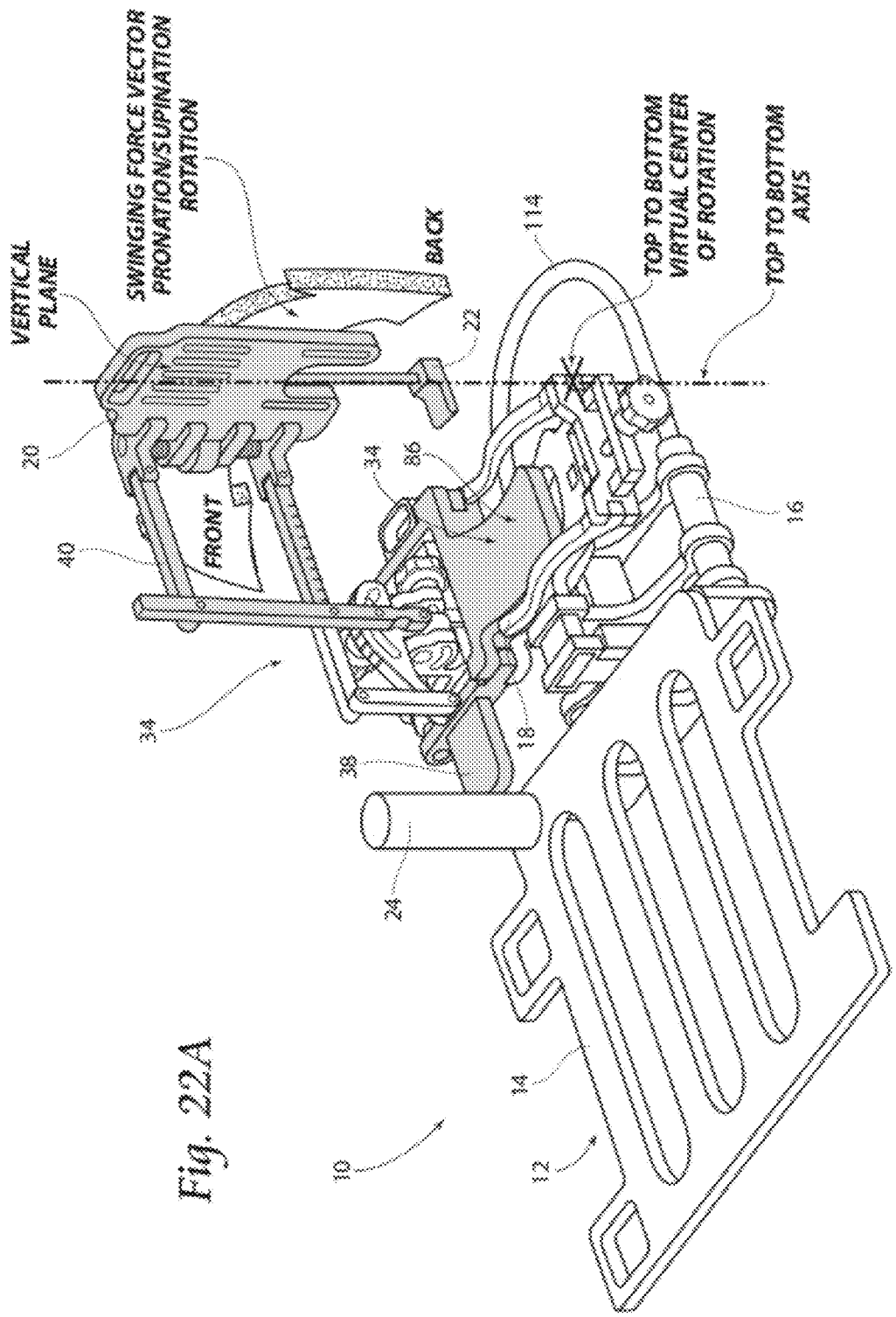

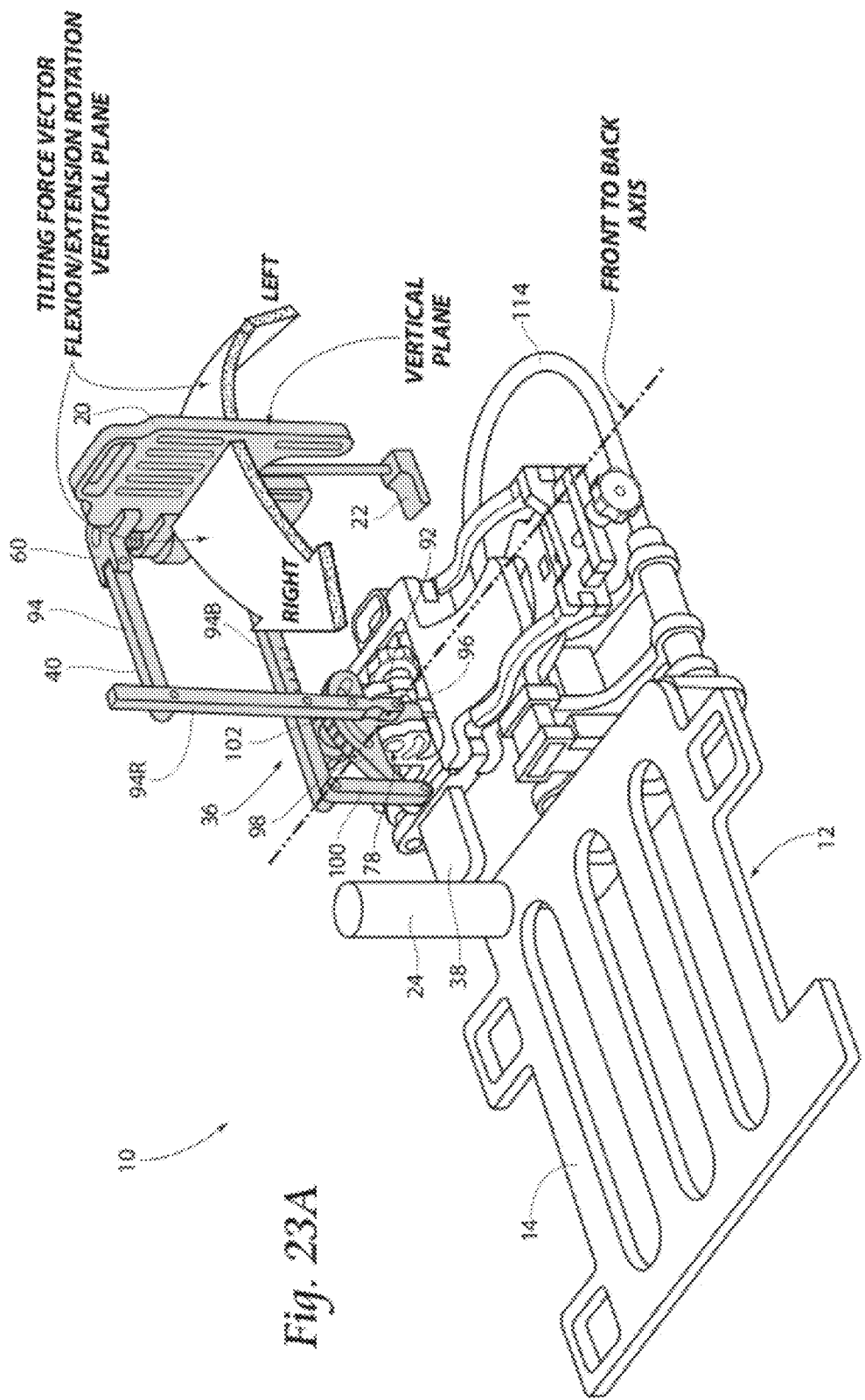

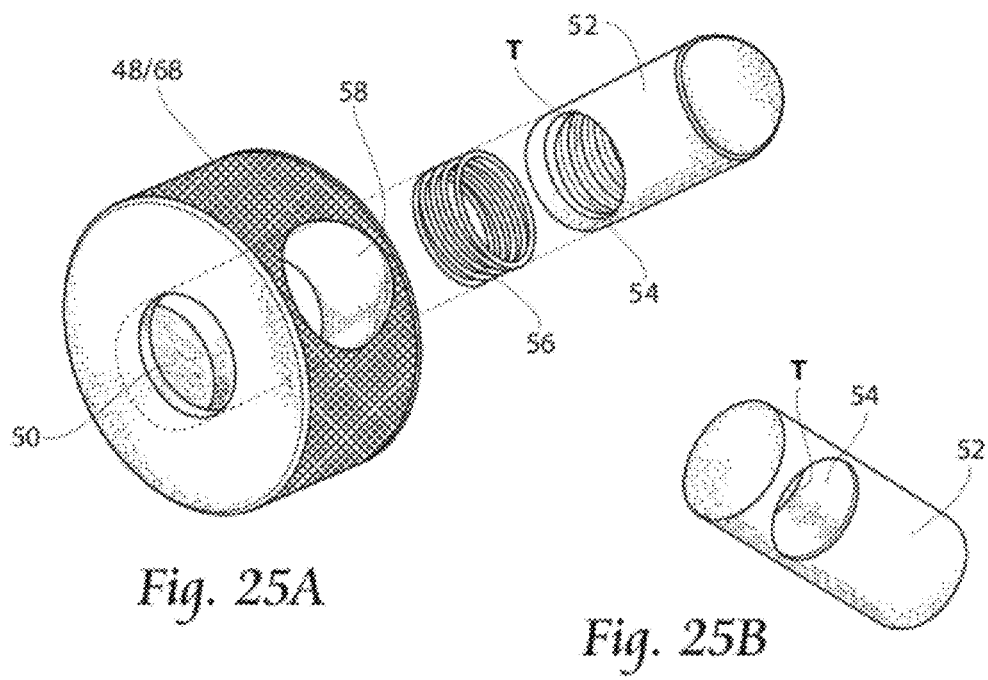
Fig. 25A
Fig. 25B
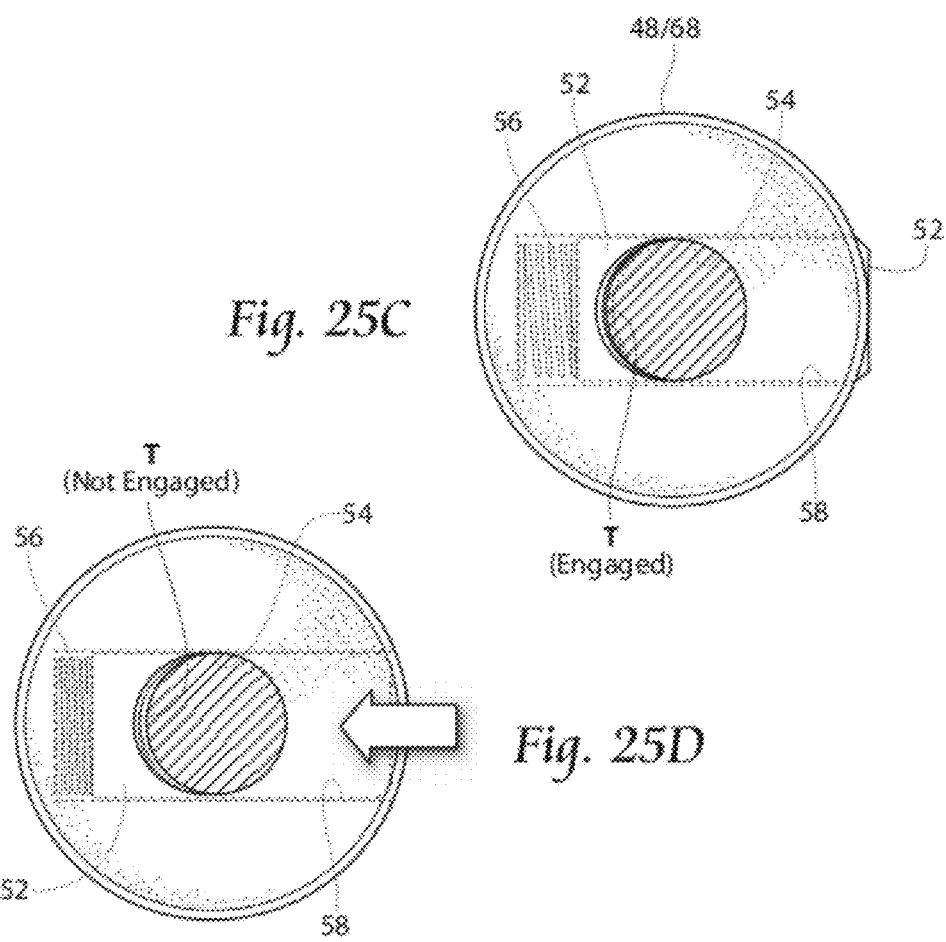
Fig. 25C
Fig. 25D

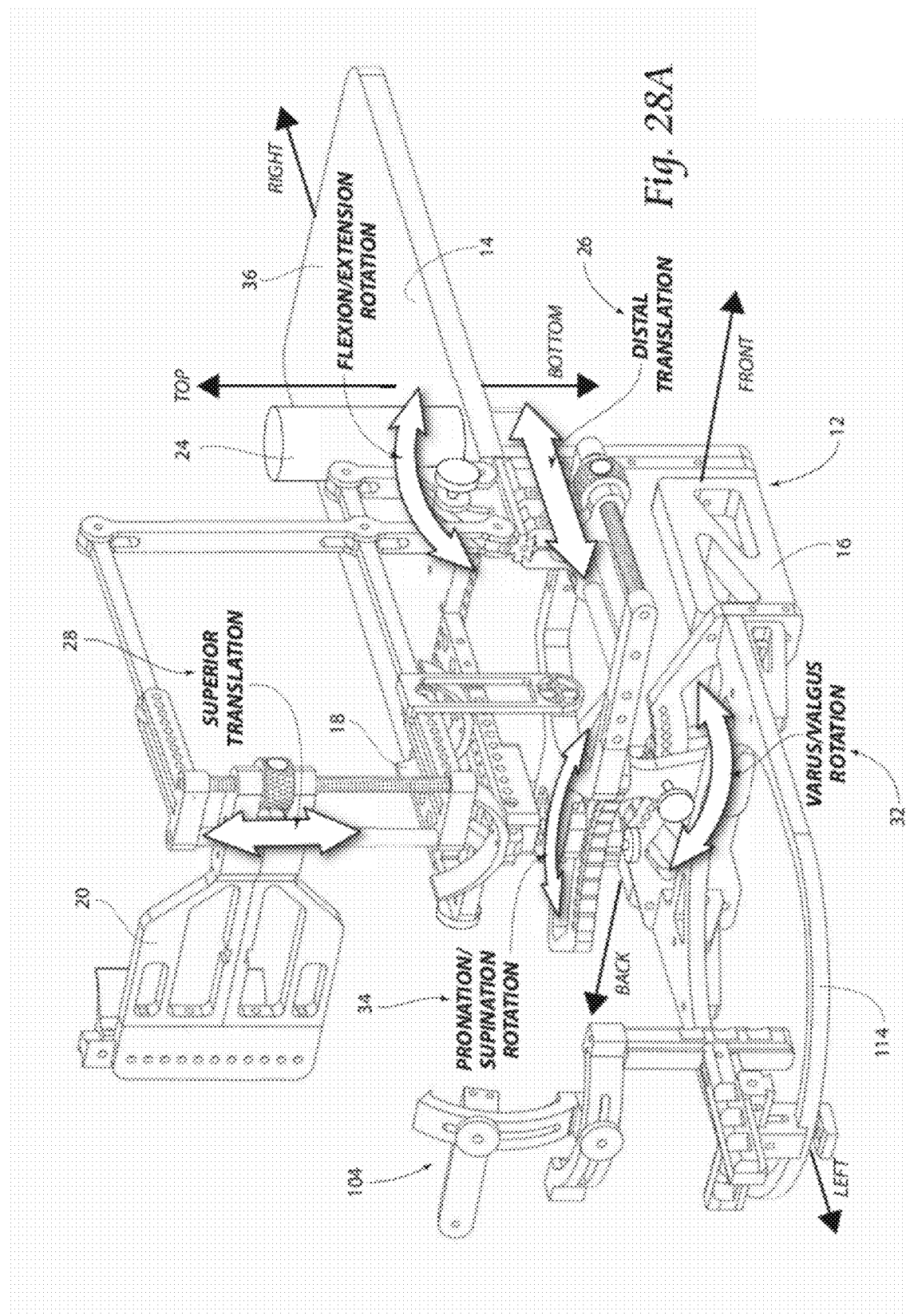

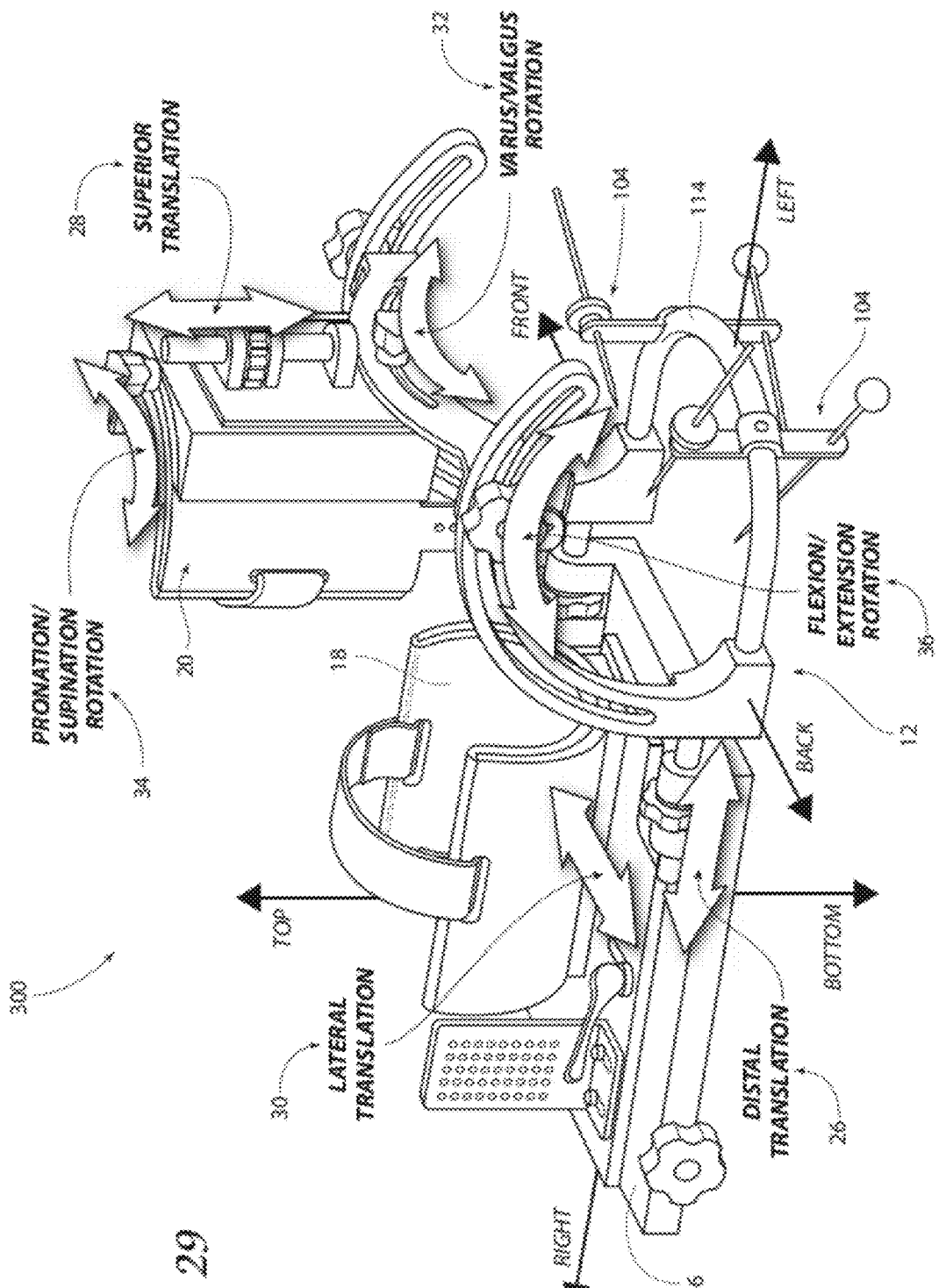

Radiographic
Lateral View

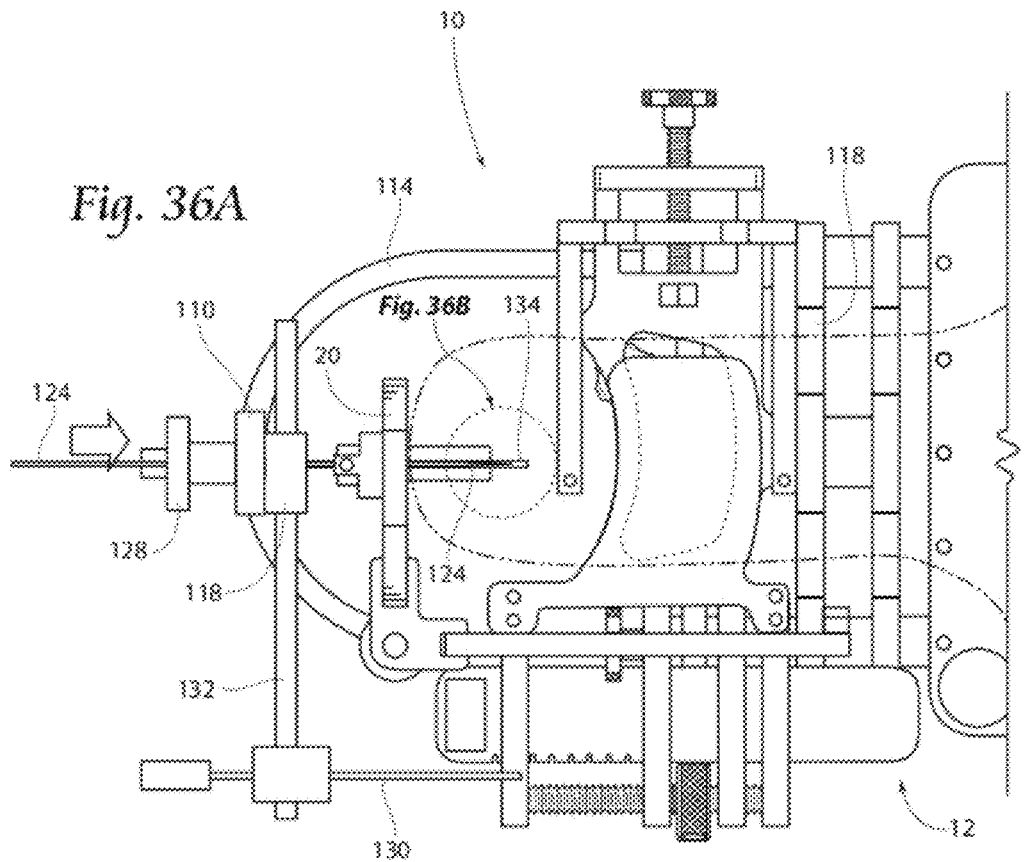
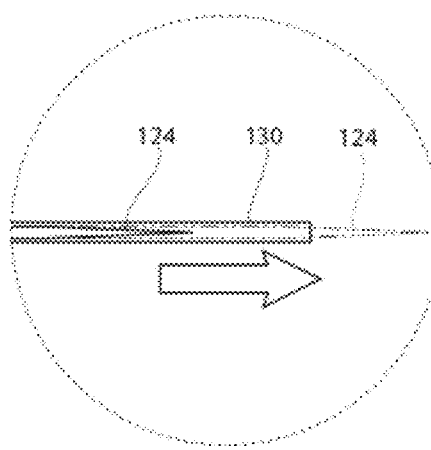

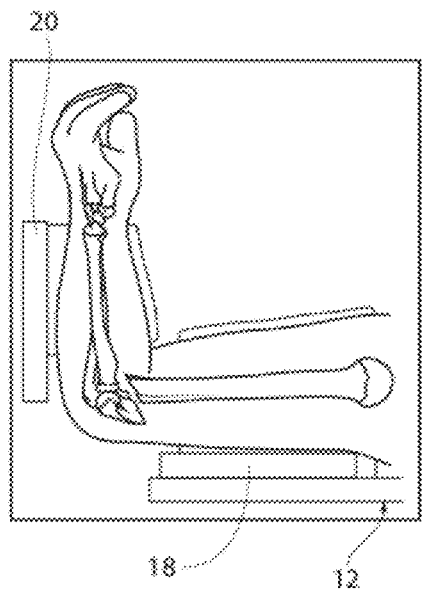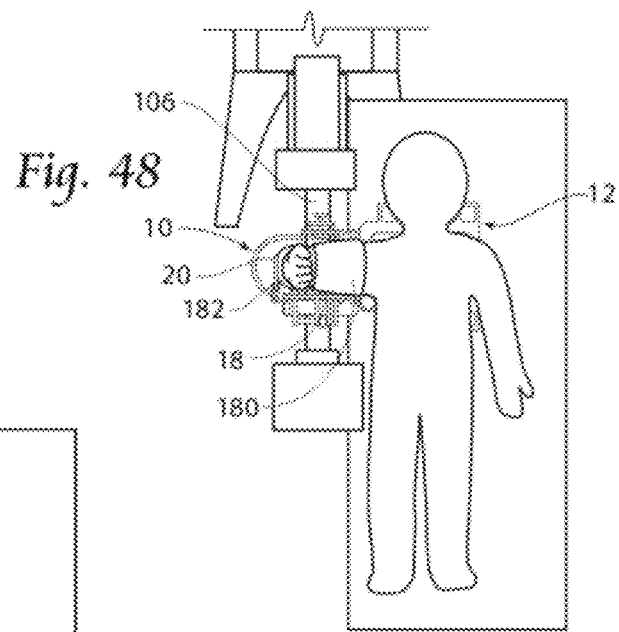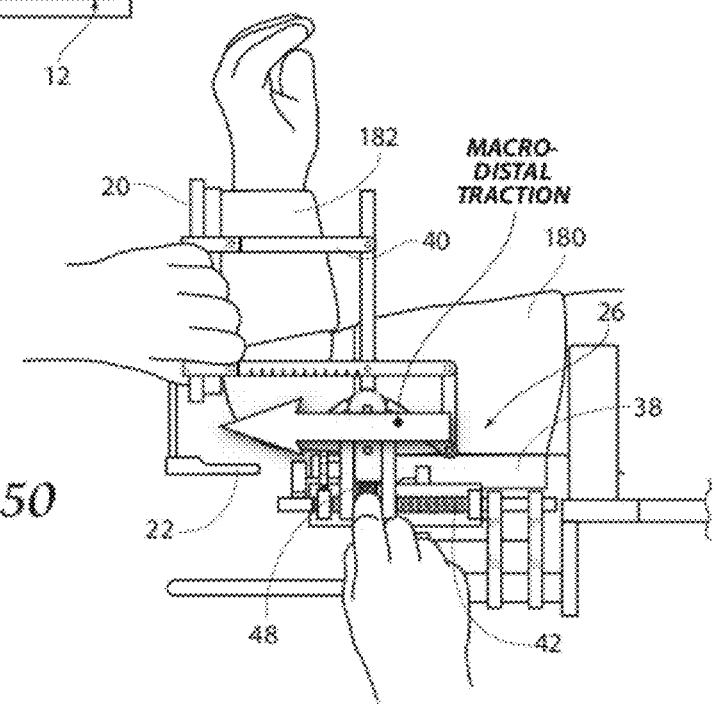
Fig. 48
Fig. 49
Fig. 50

SYSTEMS, DEVICES, AND METHODS FOR MECHANICALLY REDUCING AND FIXING BONE FRACTURES

RELATED APPLICATIONS

This application claims the benefit of U.S. Provisional Patent Application Ser. No. 61/443,080, filed Feb. 15, 2011, entitled "Systems, Devices, and Methods, for Mechanically Reducing and Fixing Bone Fractures," which is incorporated herein by reference. This application also claims the benefit of U.S. Provisional Application No. 61/396,562, filed May 28, 2010, entitled "Apparatus and Method for Reduction and Stabilization of Bone Fractures," which is incorporated herein by reference.

FIELD OF THE INVENTION

The invention generally relates to systems, devices and methods for reducing and fixing bone fractures.

BACKGROUND OF THE INVENTION

Bone fractures can occur in various regions of the body, and affect both children and adults. Bone fractures can occur, e.g., in the arm, involving the humerus and/or forearm and/or wrist; in the leg, involving the tibia and/or fibula; or at, in, or near articulating condyles (also called a condular fracture), e.g. at, in, or near the elbow, or at, in, or near the knee.

Under some circumstances bone fractures may require more intensive treatment than simple immobilization. For example, due to the severity of the fracture, certain bone fractures may require surgical reducing and fixing, including placement of pins, screws, or other fixation devices, which must be precisely positioned to ensure that the fracture is properly reduced (i.e., aligned) and fixed during recovery and healing.

By way of example, several different treatment options exist for condylar fractures above the elbow, called supracondylar fractures. A supracondylar fracture is shown in FIGS. 7 and 8. Supracondular fractures are relatively common in children, and may occur for example, when a child falls onto an outstretched arm. Fractures of this type may be classified according to the degree of fracture fragment separation, with the resultant treatment being predicated upon the fracture classification.

For example, Type 1 fractures are un-displaced or minimally displaced fractures, such as hairline fractures and are treated with simple immobilization in a cast without any manipulation. Type 2 fractures are partially displaced such that the fragments are nearly aligned, with some bony contact present. This type is typically treated by manipulation followed by immobilization in a cast. Type 3 fractures (see, e.g., FIGS. 7 and 8) are completely displaced with fracture fragments far apart from each other.

In known methods for treating type 2 and 3 fractures (see FIGS. 1 to 3), the current standard of care is, by manual manipulation of the arm (see FIG. 1), a surgeon attempts to return the fractured bone fragments to an anatomically normal alignment, which can also be called "manual reduction." Following manual reduction, the fracture is "fixed" (see FIG. 2), during which the surgeon will hold the manually reduced bone fragments in place and insert pins or other fixation device, while checking radiographs to verify pin placement, to prevent the manually reduced bone fragments from moving out of alignment during the healing process (see FIG. 3).

In the current standard of care, both manual reduction and fixing are performed "free hand" with the aid of radiation imaging. The current standard of care is, at best, problematic in several respects. First, by free hand manual manipulation, the surgeon can at best only approximate a complete anatomic reduction of a complex fracture in all anatomic planes. Manual reduction competes against itself: manually bringing the fracture into alignment in one anatomic plane, can move the fracture out of alignment in another anatomic plane. Second, the surgeon must by free hand manual manipulation attempt to hold the free hand reduction in place, while also in a free hand fashion simultaneously insert the pins to fix the reduction. A loss of manual reduction, imperfect to begin with, occurs. As a result, the current standard of care is frequently inaccurate, with patient injury resulting from incomplete reduction. Third, the repeated radiation imaging of the fracture during manual reduction and pin placement process exposes both the patient and the surgeon's hands again and again to radiation.

While the traditional manual treatment method is effective in some instances, exposure of the fracture through an open incision is often required. Such treatment is invasive. Further, operative time for these difficult to treat fractures may become lengthy and exceed seven hours.

Due to the obvious risks involved, improvement in manual fracture reduction and fixation is desired.

SUMMARY OF THE INVENTION

One aspect of the invention provides devices, systems, and methods for mechanically reducing bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee.

In one embodiment, devices, systems, and methods are provided that are sized and configured to provide reduction of a bone fracture by the application of mechanical force, which in shorthand will be called "mechanical force reduction." As used herein, the terms "mechanical" and "mechanism" broadly connote the presence of one or more tools or instruments that generate and transform the direction or magnitude of a force to reduce a bone fracture by applying kinetic energy and/or electrical energy and/or pneumatic energy and/or hydraulic energy and/or chemical energy, and/or thermal energy, and/or elastic energy, and combinations thereof. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that generates/applies force to reduce a bone fracture that includes, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

In one representative implementation, mechanical force reduction includes (i) supporting a body region having the bone fracture on a frame; (ii) operating a first reduction mechanism on the frame to apply to the bone fracture a first predefined force reduction vector that returns the bone fracture to a corrective alignment in a first anatomic orientation;

(iii) mechanically maintaining the corrective alignment in the first anatomic orientation; (iv) independent of (ii) and operating a second reduction mechanism on the frame to apply a second predefined force reduction vector that returns the bone fracture to a corrective alignment in a second anatomic orientation different than the first anatomic orientation without altering the corrective alignment in the first anatomic orientation, and (v) mechanically maintaining the corrective alignment in the second anatomic orientation.

The predefined force reduction vectors can be applied with manual control and/or guidance by the caregiver. Alternatively, on in combination, the predefined force reduction vectors can be applied with computer or robotic control and/or guidance.

Reduction can proceed in a systematic, stepwise fashion, by applying predefined force reduction vectors one at a time, and mechanically maintaining one corrective alignment before proceeding with the next, until alignment in all desired anatomic orientations is achieved. Alternatively, the caregiver can chose to proceed to apply two or more predefined force reduction vectors concurrently, to achieve concurrent corrective alignments in more than one anatomic orientation at the same time (including moving one bone region relative to another bone region or the movement of both bone regions concurrently), and mechanically maintaining the concurrently-achieved corrective alignments. The former, stepwise approach is preferred, particularly when the predefined force reduction vectors are applied with manual control and/or guidance. Still, it should be appreciated that the technical features of the invention can be achieved without a stepwise approach.

The invention makes possible the systematic identification of the mechanical force vectors required to achieve, for a given bone fracture, reduction of a bone fracture in all possible anatomic orientations that result in a complete reduction of the fracture. For example, in one representative embodiment, mechanical force reduction comprises applying predefined force reduction vectors to achieve desired by (i) distal traction; and/or (ii) superior traction; and/or (iii) lateral traction; and/or (iv) varus/valgus rotation; and/or (v) pronation/supination rotation; and/or (vi) flexion/extension.

Another aspect of the invention provides devices, systems, and methods for mechanically guiding the fixing of a reduced bone fracture, simple or complex, involving any bone region, in children or adults, which in shorthand will be called "mechanical bone fixing guidance." As used herein, the terms "mechanical" and "mechanism" broadly connote the presence of one or more tools or instruments that guide the insertion of a bone fixing device. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that guides the insertion of a bone fixing device using, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

In one representative implementation, mechanical bone fixing guidance is combined with mechanical force reduction of a bone fracture.

Yet another aspect of the invention provides devices, systems, and methods that include instrumentation sized and configured to achieve reduction and fixing of a bone fracture of an individual. The instrumentation includes a companion orthotic. The companion orthotic structure may at first reside with the instrumentation or be separate from the instrumentation, where it is fitted to the individual. On the instrumentation, the fitted companion orthotic structure conforms to and reinforces the fixed fracture reduction that the instrumentation achieves. After the instrumentation achieves the desired fixed reduction of the fracture, the fitted companion orthotic, conforming to and reinforcing the fixed reduction, can be separable from the instrumentation, to maintain and reinforce the fixed reduction while the individual goes on with their life. The fitted companion orthotic maintains and reinforces the fixed reduction as the individual ambulates and healing proceeds. In one representative implementation, the instrumentation comprises mechanical force reduction and/or mechanical bone fixing guidance.

The various aspects of the invention, whether implemented alone or in combination, provide devices, systems, and methods that significantly advance the standard of care for the treatment of fractures, simple or complex, of all bone types, in children or adults. Compared to manual fracture reduction and fixation, which are performed "free hand" with the aid of persistent radiation imaging, mechanical force reduction and/or mechanical bone fixing guidance, with or without the accompaniment of an ambulatory fitted companion orthotic, make possible a complete anatomic reduction of a complex fracture in all desired anatomic planes. Mechanical force reduction does not compete against itself: it returns a bone fracture to a corrective alignment in at least one anatomic orientation and holds stationary the corrective alignment in the at least one anatomic orientation while the bone fracture is returned to corrective alignment in at least one other anatomic orientation, without altering any corrective alignment in an already-achieved anatomic alignment. Patient injury resulting from incomplete reduction is minimized. Mechanical bone fixing guidance, with or without mechanical force reduction, minimizes the loss of reduction and achieves fixation accuracy that protects the patient from injury. An ambulatory companion orthotic further minimizes the loss of reduction and preserves fixation accuracy as healing occurs to achieve the therapeutic objectives underlying the reduction and fixing in the first place. The deliberateness and precision of mechanical force reduction and/or mechanical bone fixing guidance make it possible to reduce the time of exposure to radiation while reducing and fixing the fracture to the benefit of both the patient and the surgeon.

Other objects, advantages, and embodiments of the invention are set forth in part in the description which follows, and in part, will be obvious from this description, or may be learned from the practice of the invention.

BRIEF DESCRIPTION OF THE DRAWINGS

FIGS. 5 and 6 are, respectively, an anterior and a posterior view of the supracondylar region and adjoin bone structures in a right human arm.

FIGS. 7 and 8 are, respectively, an anterior and a posterior view of bone structures in the right human arm, like that shown in FIGS. 5 and 6, but also showing a supracondylar fracture, showing left-right displacement of the proximal and distal bone fragments of the fracture.

FIGS. 18A to 18C are perspective views of the components of the system shown in FIGS. 17A to 17F that function to achieve distal traction.

FIGS. 19A to 19C are perspective views of the components of the system shown in FIGS. 17A to 17F that function to achieve superior traction.

FIGS. 22A to 22C are perspective views of the components of the system shown in FIGS. 17A to 17F that function to achieve pronation/supination rotation.

FIGS. 23A to 23C are perspective views of the components of the system shown in FIGS. 17A to 17F that function to achieve flexion/extension rotation.

FIGS. 25A to 25D are further views of the control knob shown in FIGS. 24A and 24B showing further details of the form and function of the control knob.

FIGS. 28A to 28C are perspective views of another exemplary system for achieving mechanical force reduction of a bone fracture by the application of force reduction vectors comprising distal traction, superior traction, lateral traction, varus/valgus rotation, pronation/suprination rotation, and flexion/extension.

FIG. 29 is a perspective view of yet another exemplary system for achieving mechanical force reduction of a bone fracture by the application of force reduction vectors comprising distal traction, superior traction, lateral traction, varus/valgus rotation, pronation/suprination rotation, and flexion/extension.

FIGS. 36A and 36B show an a-p view of the exemplary mechanism shown FIGS. 33 and 34 in use providing mechanical guidance for the placement of one or more bone fixing devices to fix a reduced bone fracture.

FIGS. 46 to 73 are views exemplifying a method for achieving mechanical force reduction of a bone fracture by the application of force reduction vectors comprising distal traction, superior traction, lateral traction, varus/valgus rotation, pronation/suprination rotation, and flexion/extension.

DESCRIPTION OF THE PREFERRED EMBODIMENTS

This Specification discloses various devices, systems, and methods for reducing and/or fixing bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. The technical features of the devices systems and methods can be well exemplified and highlighted with respect to the reduction and fixation of supracondylar fractures of the elbow. For this reason, the devices, systems, and methods will be described in this context.

Still, it is to be appreciated that the devices, systems, and methods that embody features of the invention are not restricted to supracondylar applications. It is to be appreciated that the disclosed devices, systems, and methods are readily applicable for use in treating all types of bone fractures, simple or complex, of any bone type, in children or adults, anywhere in the body.

I. Anatomy of the Elbow

Figure 4:
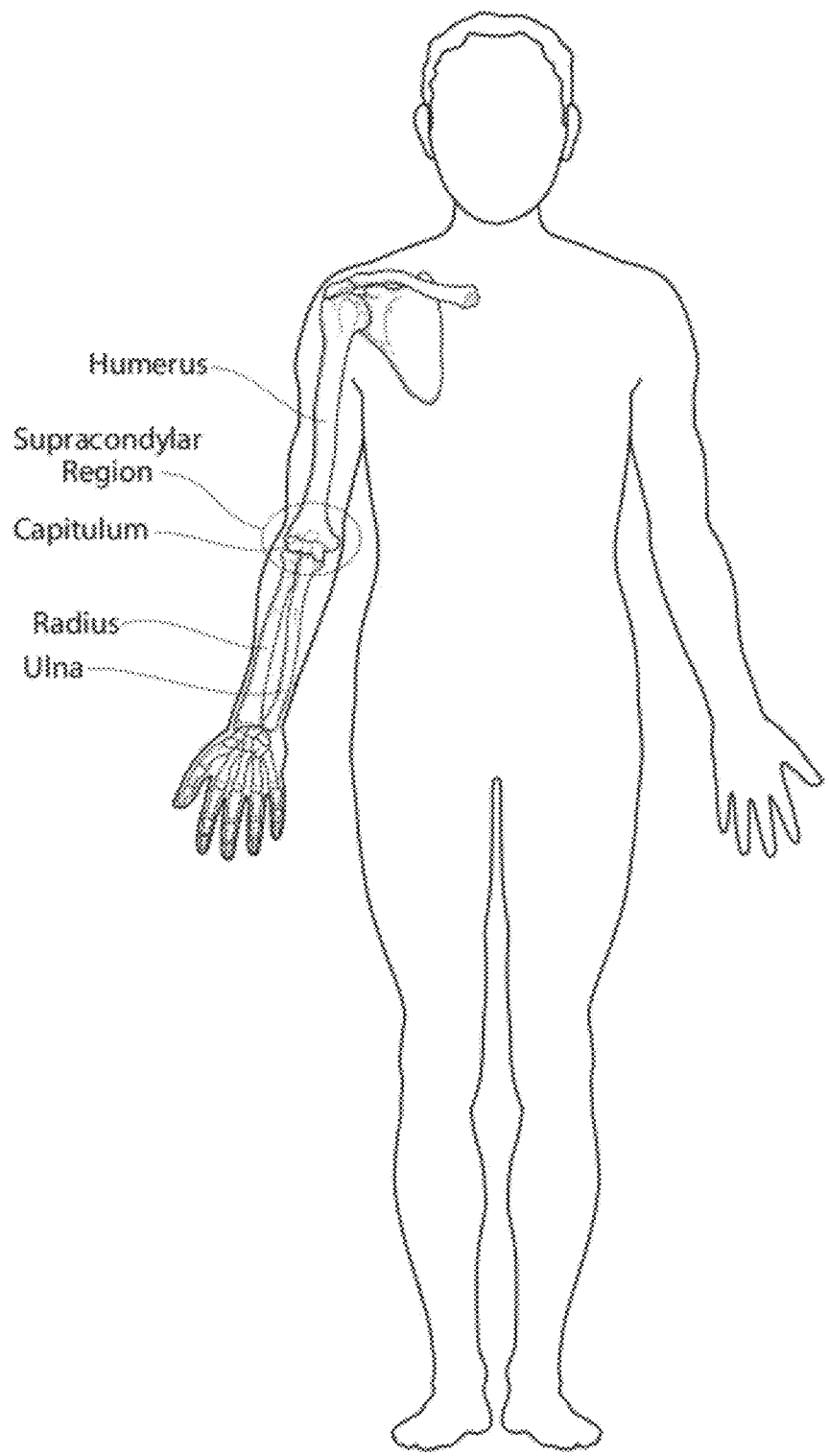
FIG. 4 is an anatomic view of a human torso, showing the supracondylar region of the right arm.

FIGS. 4, 5, and 6 exemplify the complex nature of the human elbow 10 and its various interacting components.

As can be seen in FIGS. 4, 5, and 6, the human elbow 10 is formed by the articulation of three bones; namely, the lower end of the humerus 12, the upper end of the radius 14, and the upper end of the ulna 16. Involvement of these three bones 10, 12, 14 means that the human elbow 10 consists of three joints; namely, those located (i) between the humerus 12 and the ulna 16 (the ulno-humeral joint); (ii) between the humerus 12 and the radius 14 (the radio-humeral joint); and (iii) between the ulna 16 and the radius 14 (the radio-ulnar joint).

Part of the ulna 16 that articulates with the humerus 12 includes the olecranon process 18 and the coronoid process 20. The corresponding part of humerus 12 that articulates with these processes 18, 20 is called the trochlea 22. The head of the radius 14 articulates with the capitulum 24 of the humerus 12.

II. Supracondylar Fractures

The supracondylar region (see FIGS. 4, 5, and 6) in general encompasses an area of relatively thin, weak bone located in the distal humerus 12. This region is bordered posteriorly by the olecranon fossa 26 and anteriorly by the coronoid fossa 28.

One type of fracture to the elbow 10 is a supracondylar fracture 30 (see FIGS. 7 and 8). Supracondylar fractures 30 are relatively common in children, and may occur for example, when a child falls onto an outstretched arm. With attention to the illustrated detailed views, it may be seen that the force of a fall is transmitted through the olecranon 18 to the weak supracondylar region, causing a supracondylar fracture 30.

The fracture line 30 typically propagates transversely across the distal humerus 12 through the center of the olecranon fossa 26. As FIGS. 7 and 8 show, the supracondylar fracture 30 separates the supracondylar region into a proximal fracture fragment and a distal fracture fragment. The proximal fracture fragment includes the humerus 12 (in this context, "proximal" meaning on the side of the fracture line 30 closer to the shoulder). The distal fracture fragment includes the radius 14 and the ulna 16 (in this context, "distal" meaning the side of the fracture line 30 closer to the hand).

Depending on the severity of the fracture, the separated proximal and distal bone fragments can be displaced laterally right and left (i.e., anatomically, in a medial direction toward the body or laterally away from the body). For example, FIGS. 7 and 8 show, respectively, anterior and posterior views of a supracondylar fracture 30 of the right elbow, with the distal fracture fragment displaced laterally to the left (toward the body) and the proximal fracture fragment displaced medially to the right (away from the body).

Figure 9:
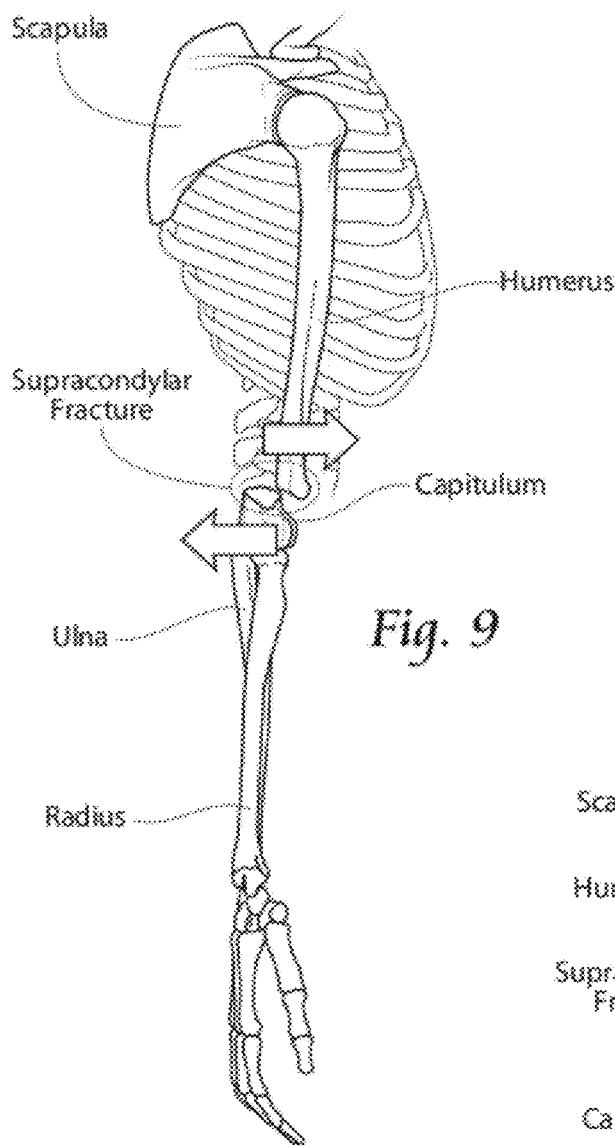
FIGS. 9 and 10 are medial views of the supracondylar fracture shown in FIGS. 7 and 8, FIG. 9 showing an anterior-posterior displacement of the proximal and distal bone fragments of the fracture, and FIG. 10 showing a rotational displacement of the proximal and distal bone fragments of the fracture.

Also depending on the severity of the fracture, the separated proximal and distal bone fragments can be displaced forward or backwards (i.e., anatomically, to the anterior (front) or to the posterior (back), respectively). For example, FIG. 9 shows a medial view (looking toward the body) of a supracondylar fracture 30 of the right elbow, with the distal fracture fragment displaced in a posterior direction (toward the back) and the proximal fracture fragment displaced in an anterior direction (toward the front).

Figure 10:
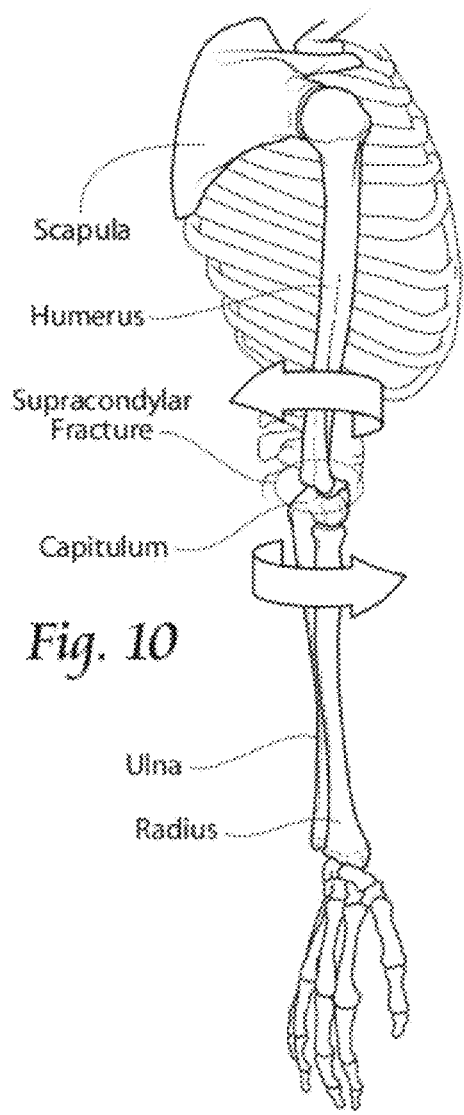

In addition to the forgoing separations and displacements of the distal fracture segment relative to the proximal fracture segment, the angular alignment of the anterior, posterior, and medial cortical surfaces of the bones in the supracondylar region may be displaced rotationally about the native longitudinal axis of the bones. For example, FIG. 10 shows a medial view (looking toward the body) of a supracondylar fracture 30 of the right elbow, with the distal fracture fragment and proximal fracture fragment displaced rotationally out of their native axial alignment.

III. Reducing and Fixing a Bone Fracture

In conventional meaning, a fracture is "reduced" by the application of one or more forces to return the bone fragments separated and displaced by the fracture back toward the native state of alignment, i.e., that which existed prior to the fracture. In conventional meaning, a fracture is "fixed" following a reduction, by stabilizing the alignment of the reduction, to prevent the reduced bone fragments from moving out of reduction as healing occurs.

Depending upon the native anatomic structure of a given fracture site, and the nature of the fracture itself, reduction and fixation of a given fracture can be difficult, inexact, and time consuming. This is particularly true for fractures in the supracondylar region, as previously described, due to the nature and extent to which the native bone structures can be separated and displaced by the fracture.

The morphology and interrelationship of native anatomic structures in a given region of the body can be generally understood by medical professionals using textbooks of human skeletal anatomy along with their knowledge of the site. The physician is also able to ascertain the nature and extent of the fracture in that region of the body using, for example, plain film x-ray, fluoroscopic x-ray, or MRI or CT scanning. Based upon this information, the physician can ascertain the magnitude and direction of forces that ideally should be applied to achieve a complete reduction of the fracture. In this specification, the magnitude and direction of these forces will be called "force reduction vectors." A force reduction vector represents a reduction force operating in a defined direction and magnitude.

Figure 11A:
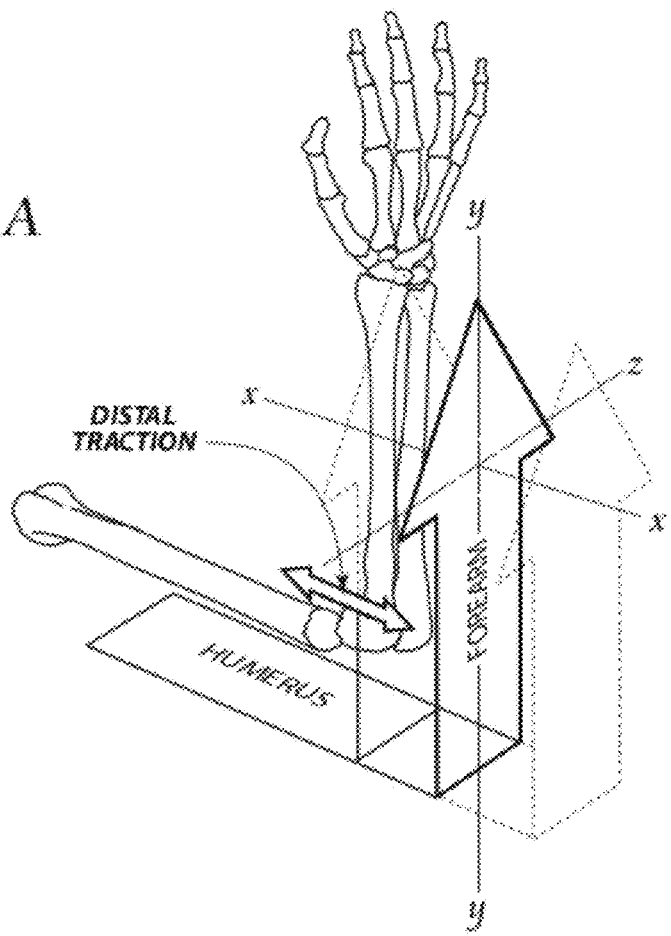
FIGS. 11A to 11D are anatomic and partially schematic views of a right human arm with a supracondylar fracture, demonstrating the application of a force reduction vector comprising distal traction.

These general principles can be applied for the purpose of illustration to the humerus and elbow to treat the supracondylar region. For example, as shown in FIG. 11A, a coordinate system comprising an x-axis, y-axis, and z-axis can be used to define the morphology and interrelationship of the native anatomic structures in the supracondylar region, which comprises the humerus, the forearm (comprising the ulna and radius), joined by the elbow joint. In FIG. 11A, the forearm is articulated relative to the humerus about the elbow joint, so that the force reduction vectors can be more readily called out and/or identified. In this coordinate system, the x-axis defines the native longitudinal axis of the humerus. The y-axis defines the native longitudinal axis of the articulated forearm, the a-axis and y-axis being perpendicular to each other. The z-axis defines the native articulation axis of the elbow joint. FIG. 11A also shows the presence of a supracondylar fracture, like that shown in FIGS. 7 to 10, thereby also defining the existence of the proximal bone fragment and the distal bone fragment as previously described.

Figure 11B:
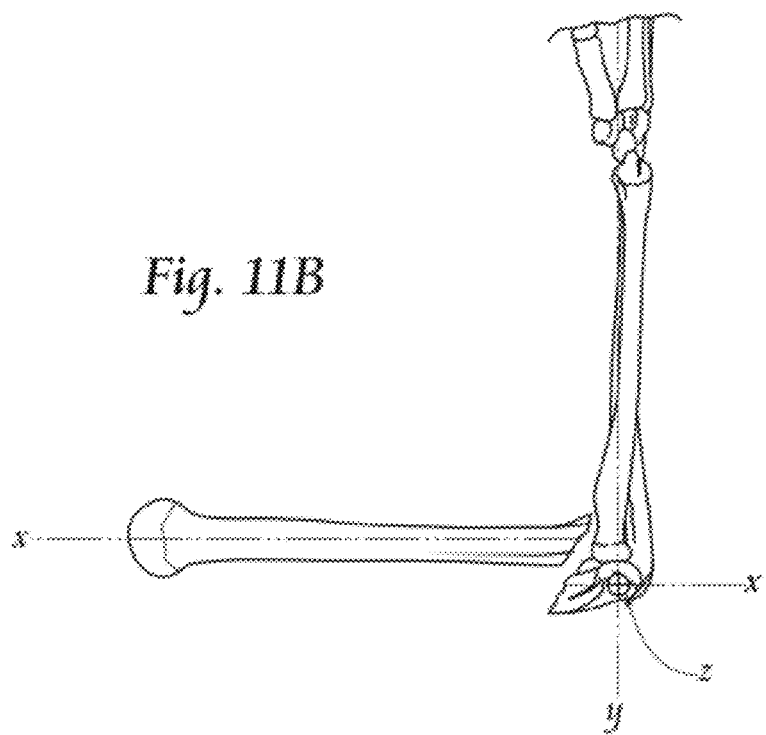
Figure 11C:
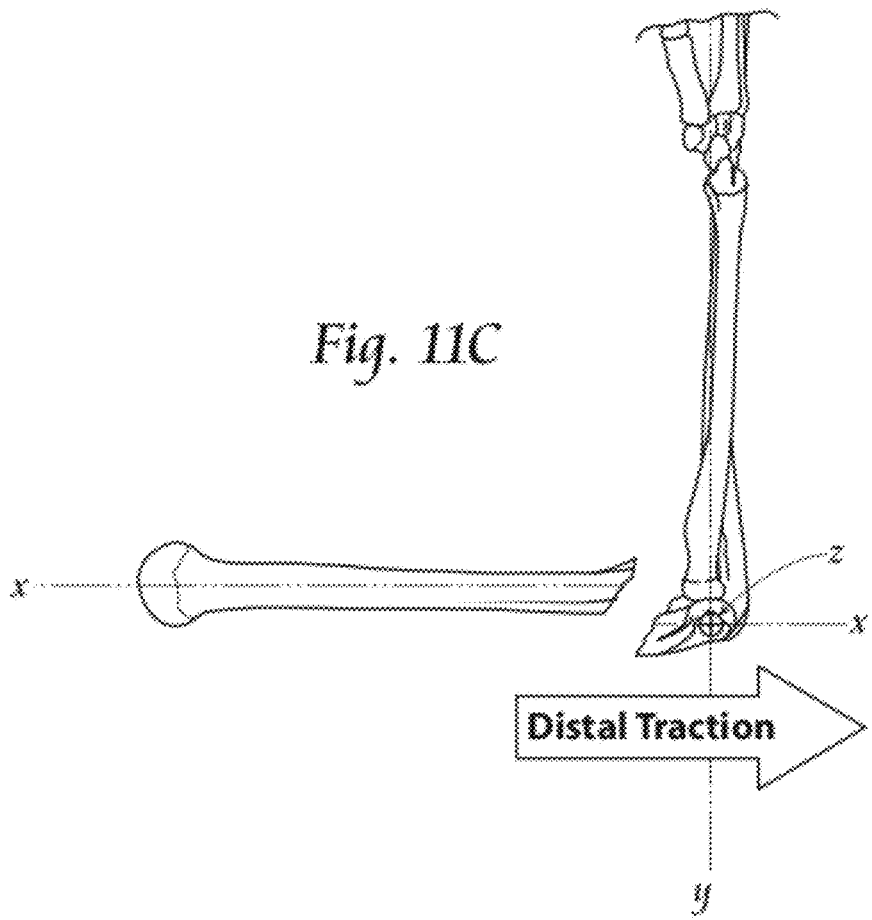
Figure 11D:
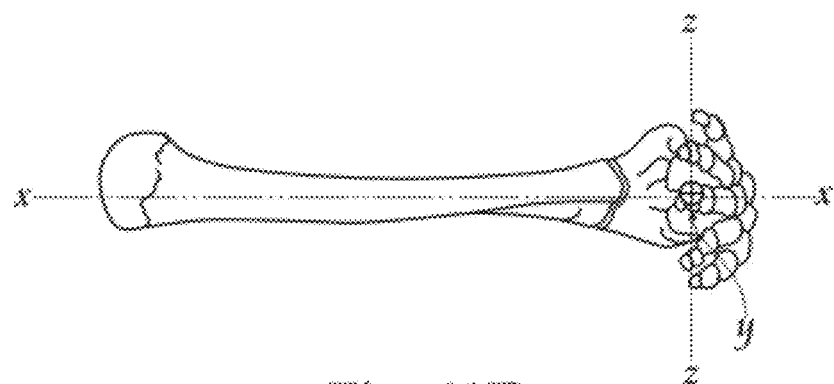

With reference to the coordinate system shown in FIG. 11A, the force reduction vectors required to achieve a complete reduction of the supracondylar fracture can be identified. As will now be described in greater detail, there are a total of six possible force reduction vectors for a supracondylar fracture. These are (i) distal traction (FIGS. 11A to 11D); (ii) superior traction (FIGS. 12A to 12D); (iii) lateral traction (FIGS. 13A to 13D); (iv) varus/valgus rotation (FIGS. 14A to 14D); (v) pronation/supination rotation (FIGS. 15A to 15D); and (vi) flexion/extension A. Distal Traction FIG. 11A illustrates a first force reduction vector called distal traction. Distal traction comprises a force vector applied along the x-axis. As shown in FIGS. 11B, 11C, and 11D, distal traction along the x-axis separates the distal bone fragment and the proximal fracture fragment so that subsequent force reduction vectors can be applied to return the proximal and distal bone fragments separated and displaced by the fracture back toward the native state of alignment.

B. Superior Traction

Figure 12A:
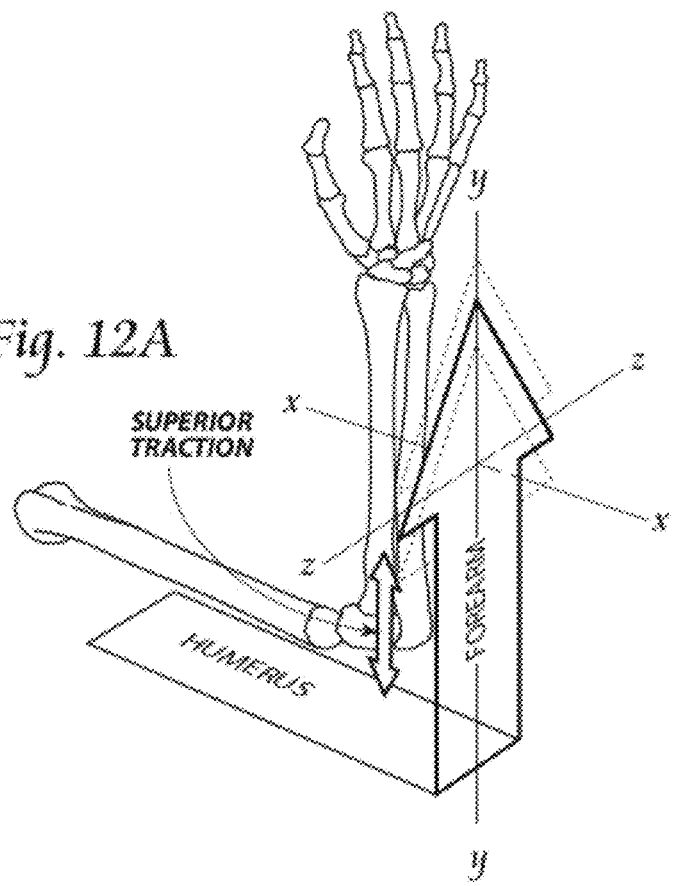
FIGS. 12A to 12D are anatomic and partially schematic views of a right human arm with a supracondylar fracture, demonstrating the application of a force reduction vector comprising superior traction.
Figure 12B:
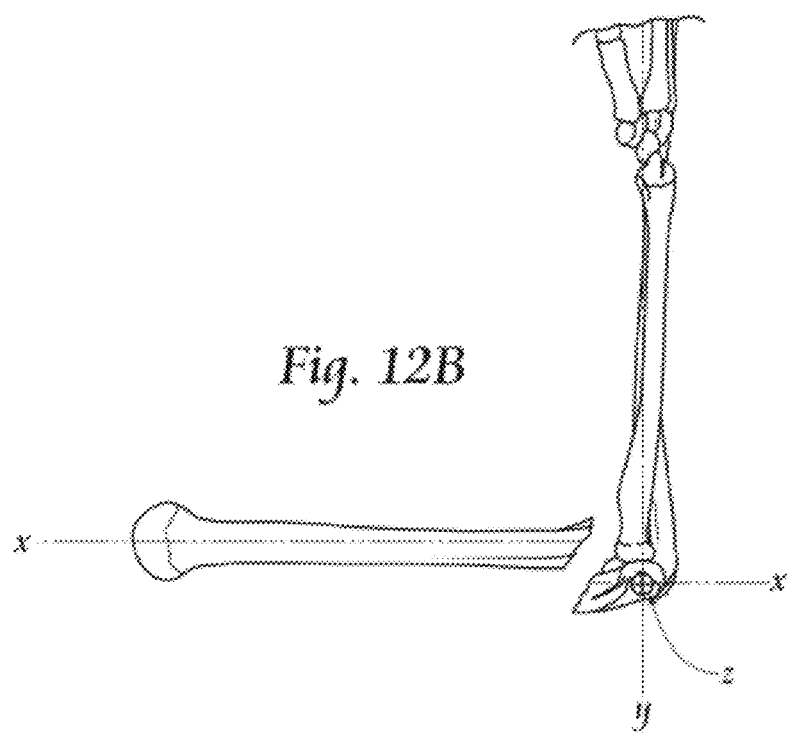
Figure 12C:
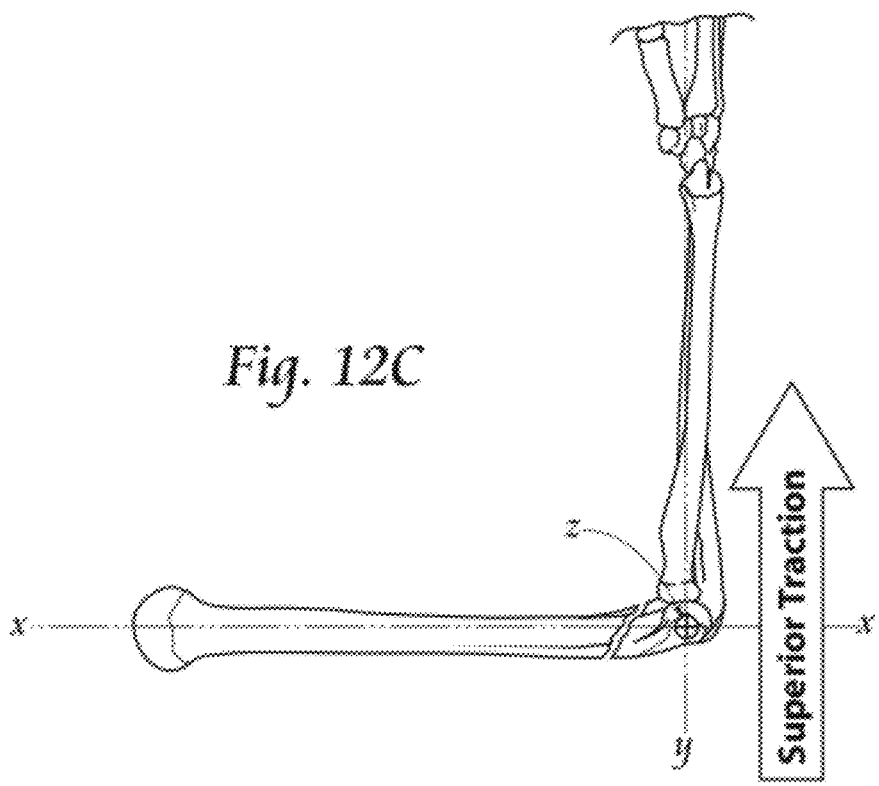
Figure 12D:
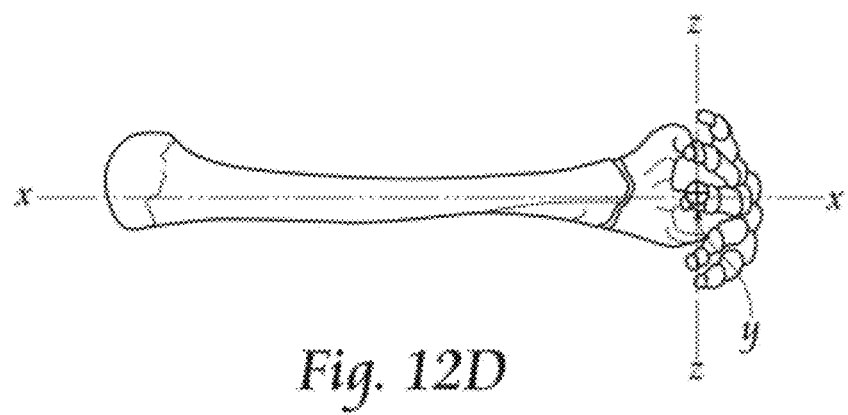

FIG. 12A illustrates a second force reduction vector called superior traction. Superior traction comprises a force vector applied along the y axis. As shown in FIGS. 12B, 12C, and 12D, superior traction along the y-axis lifts (or, in reserve, lowers) the distal bone fragment as a unit relative to the proximal bone fragment. Superior traction returns proximal and distal bone fragments that have been displaced due to the fracture forward or backwards (as shown in FIG. 9) back toward the native state of alignment.

C. Lateral Traction

Figure 13A:
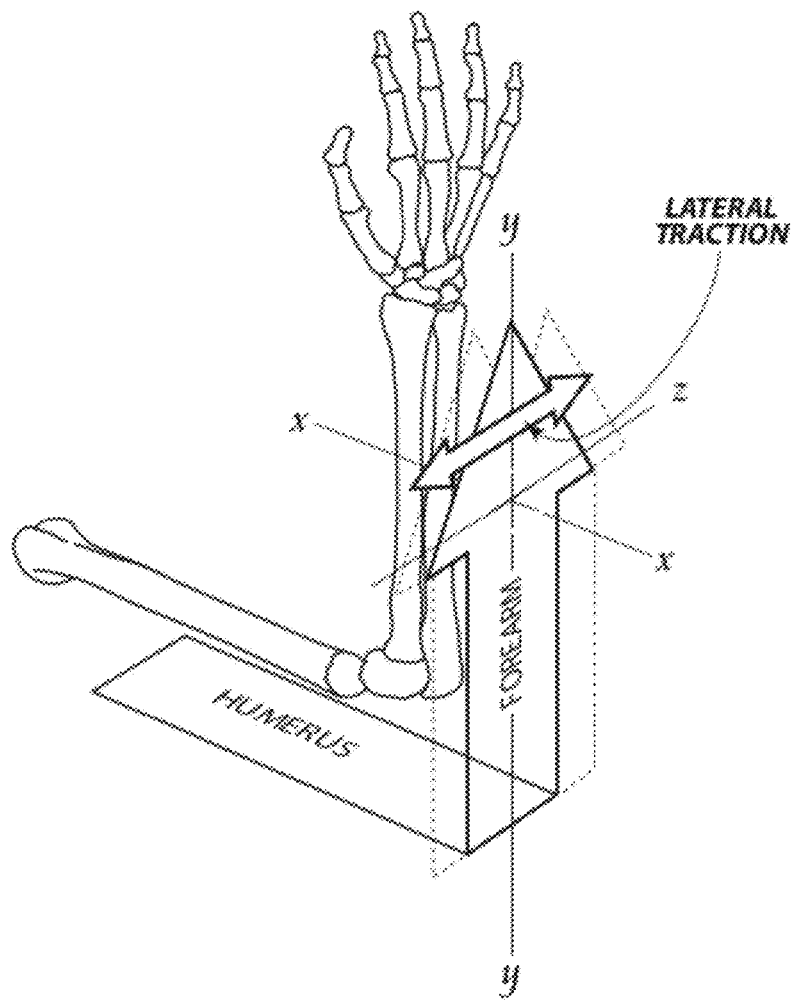
FIGS. 13A to 13D are anatomic and partially schematic views of a right human arm with a supracondylar fracture, demonstrating the application of a force reduction vector comprising lateral traction.
Figure 13B:
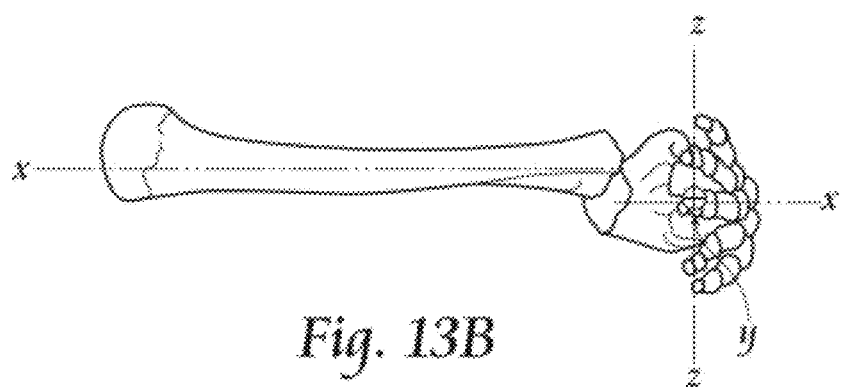
Figure 13C:
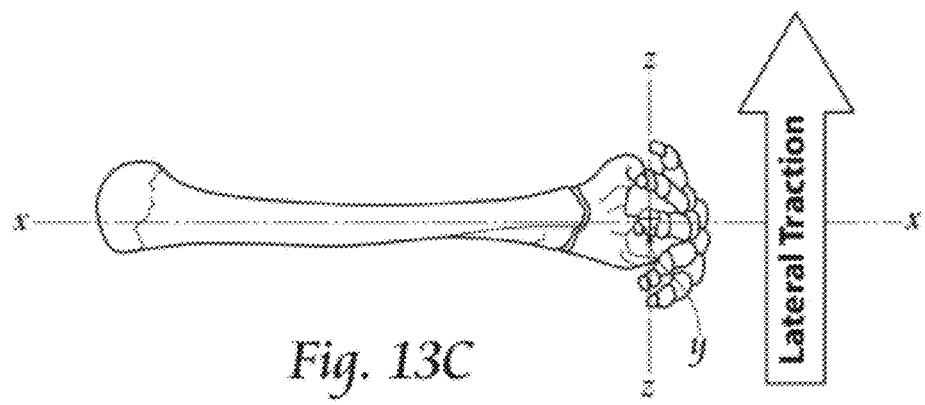
Figure 13D:
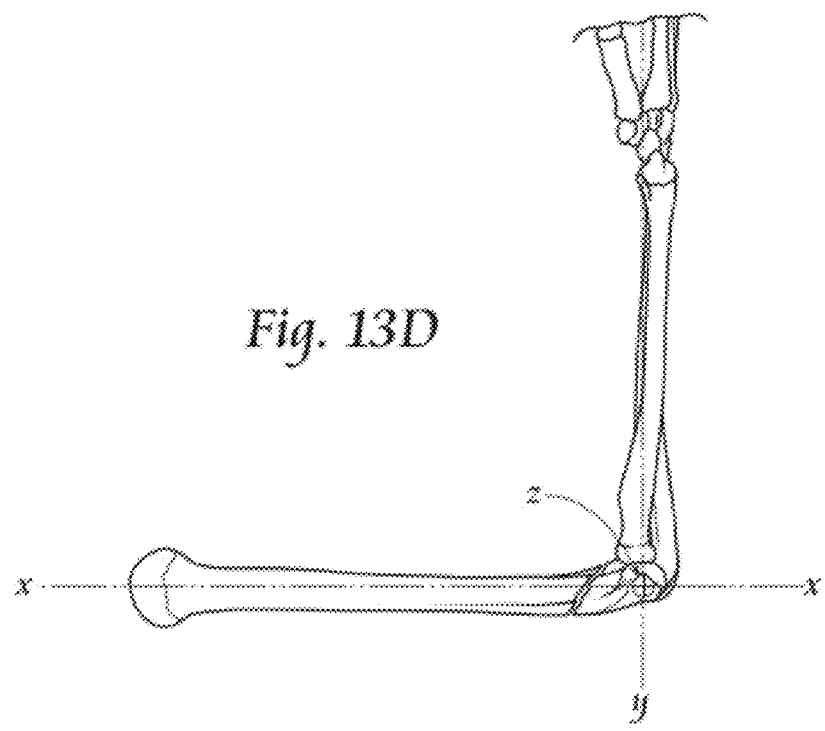

FIG. 13A illustrates a third force reduction vector called lateral traction. Lateral traction comprises a force vector applied along the z-axis. As shown in FIGS. 13B, 13C, and 13D, lateral traction along the z-axis moves the fractured end of the distal bone fragments across the fractured end of the proximal bone fragment. Lateral traction returns proximal and distal bone fragments that have been medially displaced left or right due to the fracture (as shown in FIGS. 7 and 8) back toward the native state of alignment.

D. Varus/Valgus Rotation

Figure 14A:
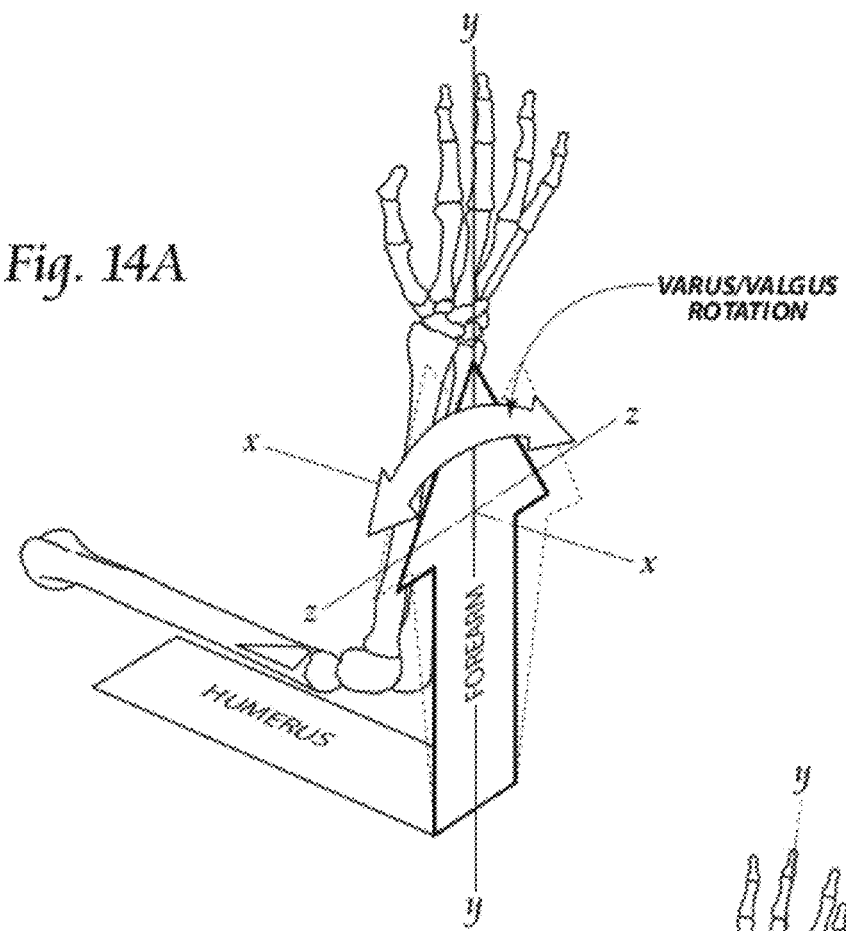
FIGS. 14A to 14D are anatomic and partially schematic views of a right human arm with a supracondylar fracture, demonstrating the application of a force reduction vector comprising varus/valgus rotation.
Figure 14B:
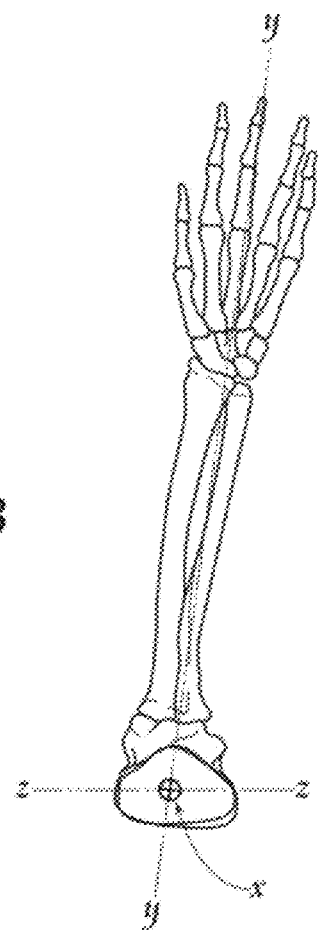
Figure 14C:
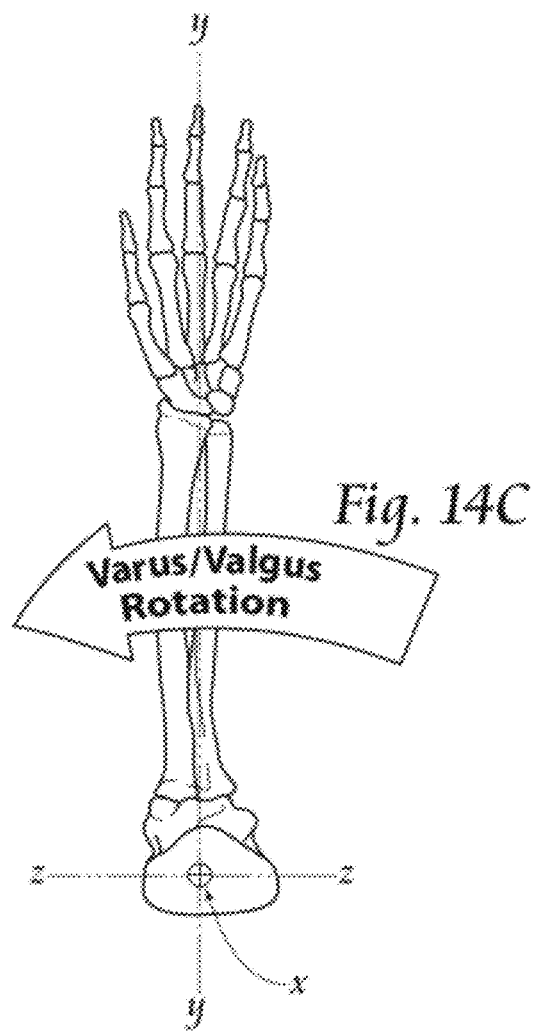
Figure 14D:
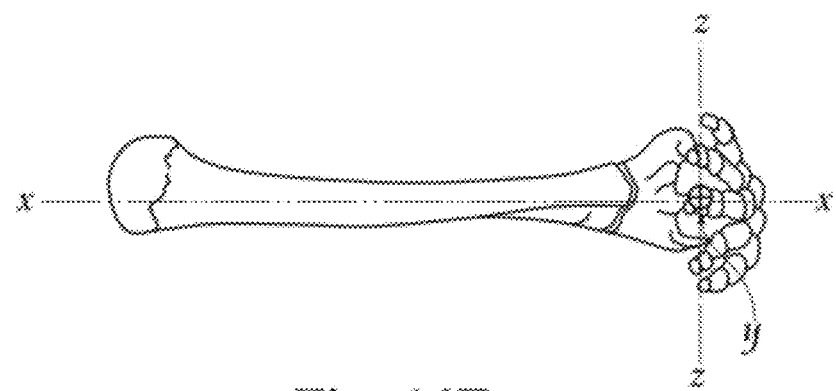

FIG. 14A illustrates a fourth force reduction vector called varus/valgus rotation. Varus/valgus rotation comprises a rotational force vector (torque) applied about the x-axis. As shown in FIGS. 14B, 14C, and 14D, varus/valgus rotation about the x-axis pivots the fractured end of the distal bone fragment about the longitudinal axis of the proximal bone fragment. Varus/valgus rotation returns proximal and distal bone fragments that have been rotationally displaced due to the fracture (as shown in FIG. 10) back toward the native state of alignment. Varus/valgus rotation serves to bring back into native alignment the posterior, anterior, and medial cortical surfaces along the fracture line.

E. Pronation/Supination Rotation

Figure 15A:
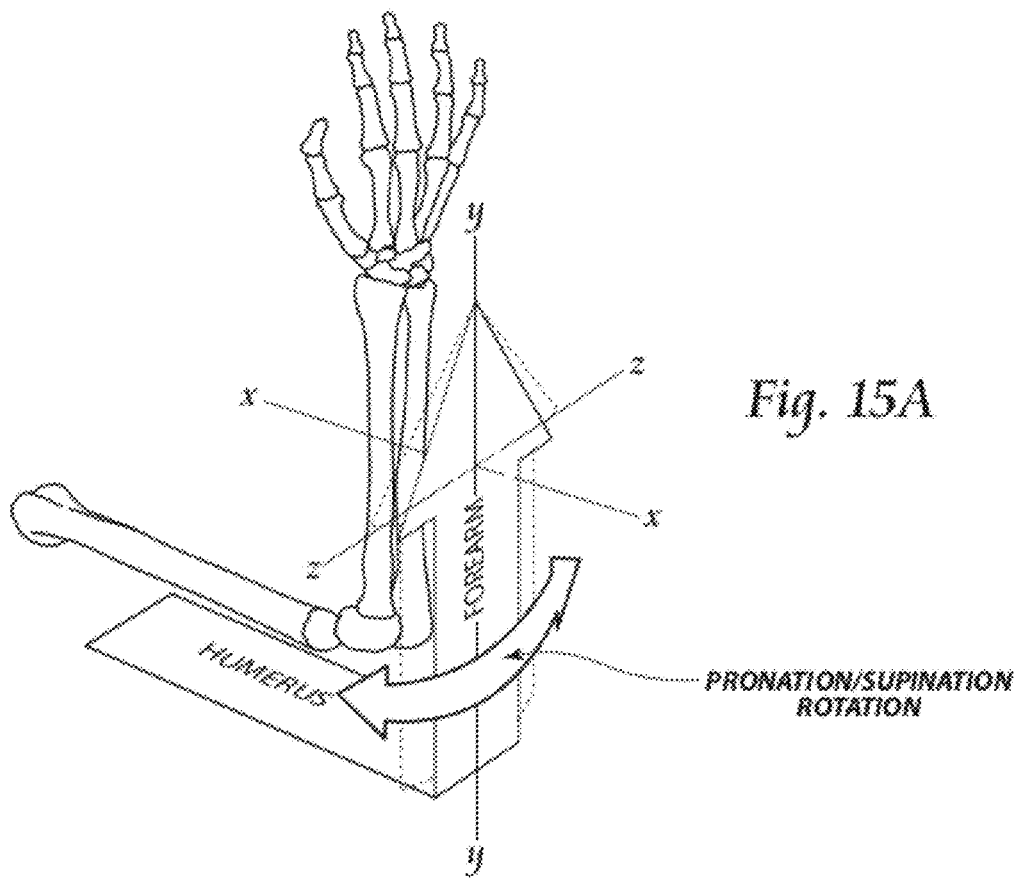
FIGS. 15A to 15D are anatomic and partially schematic views of a right human arm with a supracondylar fracture, demonstrating the application of a force reduction vector comprising pronation/supination rotation
Figure 15B:
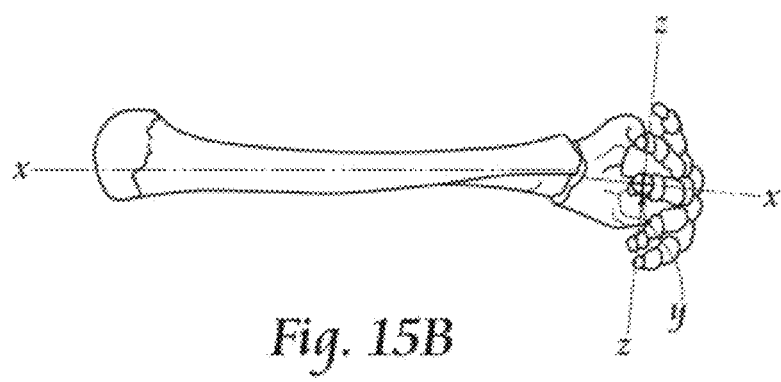
Figure 15C:
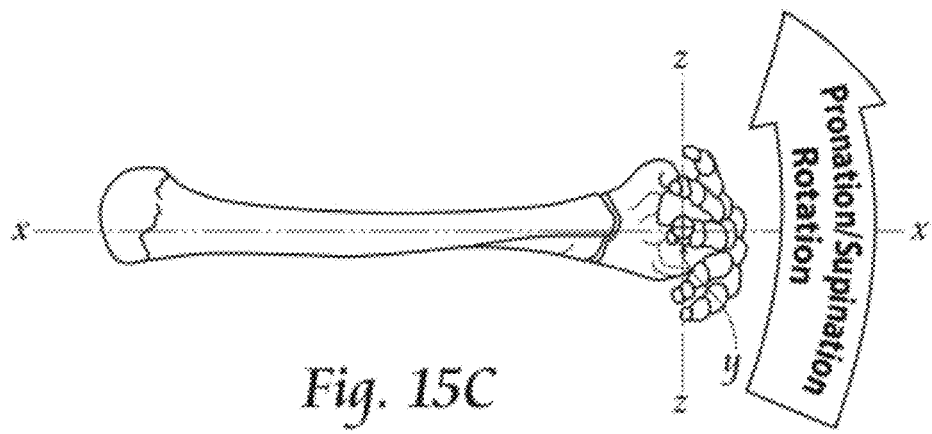
Figure 15D:
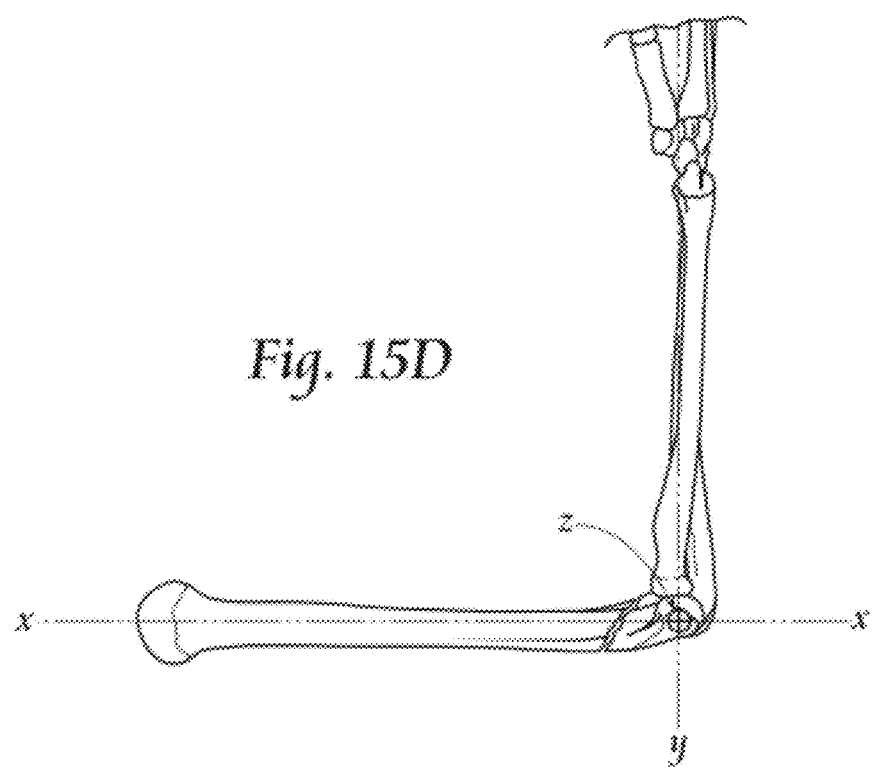

FIG. 15A illustrates a fifth force reduction vector called pronation/supination rotation. Pronation/supination rotation comprises a rotational force vector (torque) applied about the y-axis. As shown in FIGS. 15B, 15C, and 15D, pronation/supination rotation about the y-axis pivots the fractured end of the distal bone fragment about the longitudinal axis of distal bone. Like varus/valgus rotation, pronation/supination rotation returns proximal and distal bone fragments that have been rotationally displaced due to the fracture (as shown in FIG. 10) back toward the native state of alignment. Pronation/supination rotation also serves to bring back into native alignment the posterior, anterior, and medial cortical surfaces along the fracture line.

F. Flexion/Extension Rotation

Figure 16A:
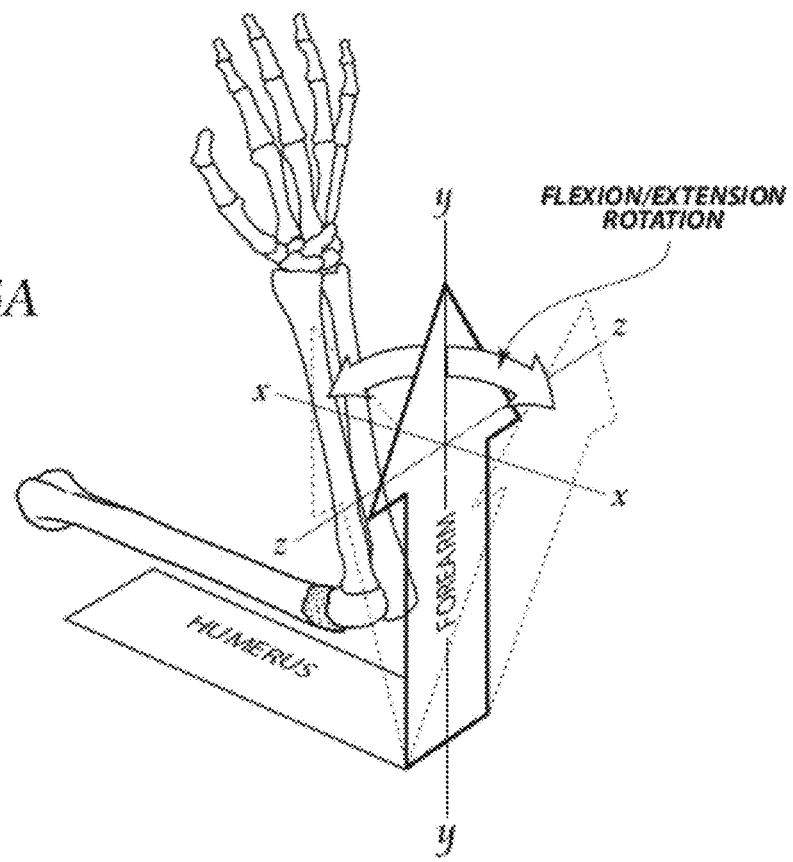
FIGS. 16A to 16D are anatomic and partially schematic views of a right human arm with a supracondylar fracture, demonstrating the application of a force reduction vector comprising flexion/extension rotation.
Figure 16B:
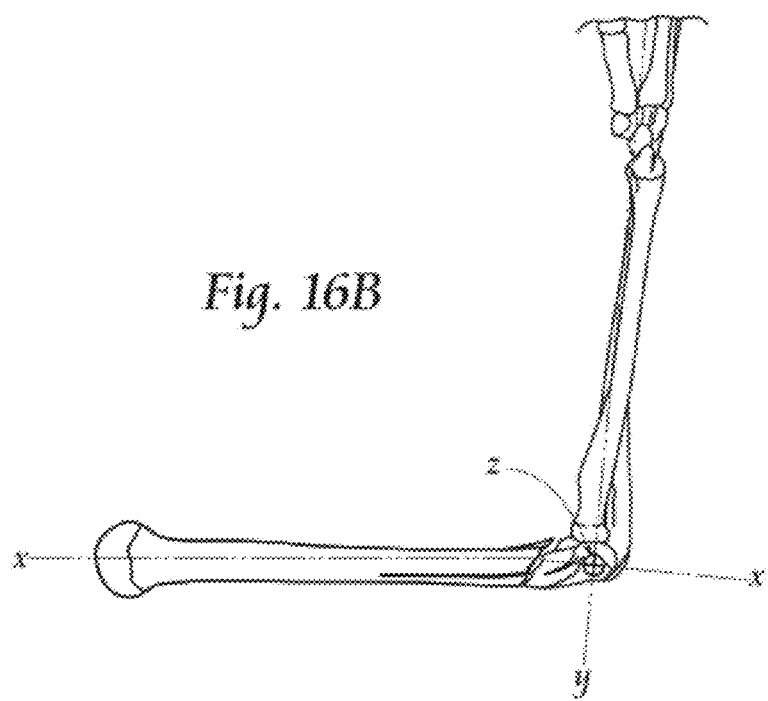
Figure 16C:
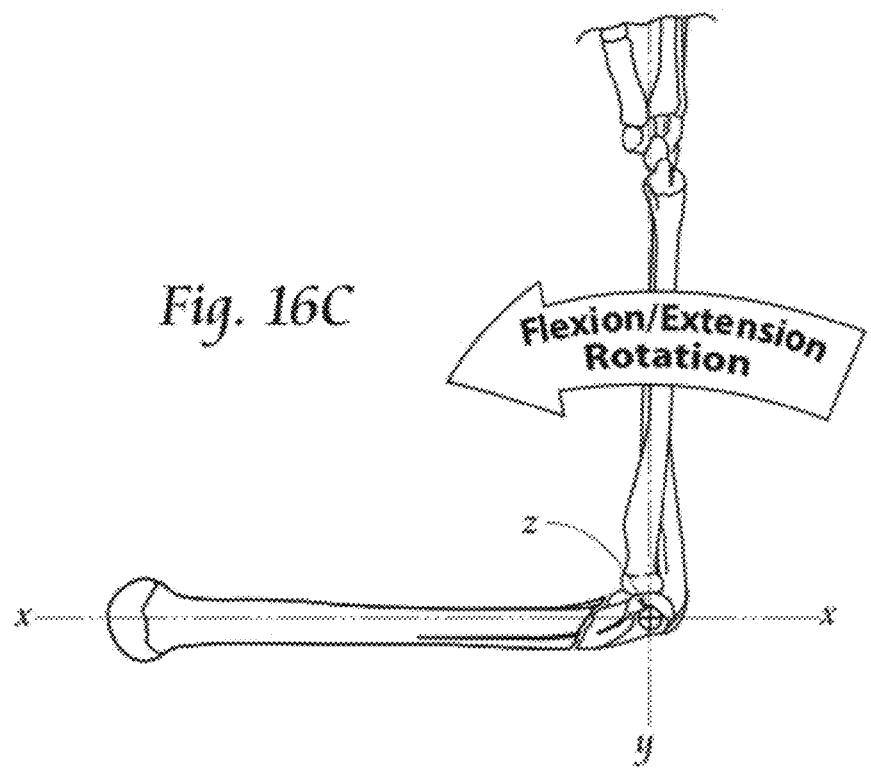
Figure 16D:
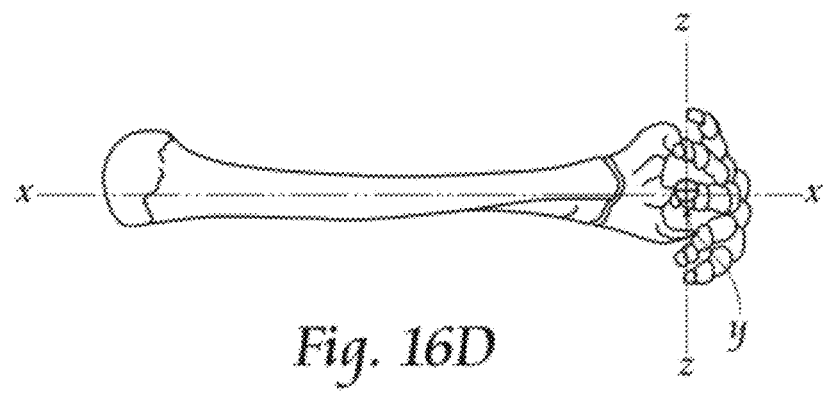

FIG. 16A illustrates a sixth force reduction vector called flexion/extension rotation. Flexion/extension rotation comprises a rotational force vector (torque) applied about the z-axis. As shown in FIGS. 16B, 16C, and 16D, flexion/extension rotation about the z-axis pivots the fractured end of the distal bone fragment toward the fractured end of the proximal bone fragment. Flexion/extension rotation returns the fractured ends of the proximal and distal bone fragments that have been separated due to the fracture back toward the native state of alignment.

IV. Systems and Devices for Mechanically Reducing a Bone Fracture

A. Overview

The rationale of systematically identifying force reduction vectors, although previously described in the context of reducing supracundular fractures, provides the context for achieving, in a systematic way, a reduction of any bone fracture. Still, in this context, systemic problems can still exist.

Force reduction vectors, once identified, are inherently different in terms of their therapeutic objectives and results. For example, in the context of reduction of a supracondylar fracture, the force reduction vectors independently operate along three different x-, y-, and z-axes. Achieving a desired therapeutic result along one axis can be lost or compromised when an attempt is made to achieve a therapeutic result along another axis. For example, the therapeutic objectives of distal traction can be lost or compromised when a different force reduction vector is next applied along another axis. The loss of distal traction can, in turn, obstruct the application of another force vector. Further, the application of superior traction can alter the therapeutic results of a previously achieved lateral traction, or vice versa, or the application of varus/valgus rotation can alter the results of a previously achieved pronation/supination rotation or flexion/extension rotation, and so on. Force reduction vectors for whatever fracture operate in a dynamic interdependent physical environment. This dynamic interdependent physical environment thwarts achievement of a complete reduction by the application of independent force reduction vectors along different axes.

B. Mechanical Force Reduction

Figure 17A:
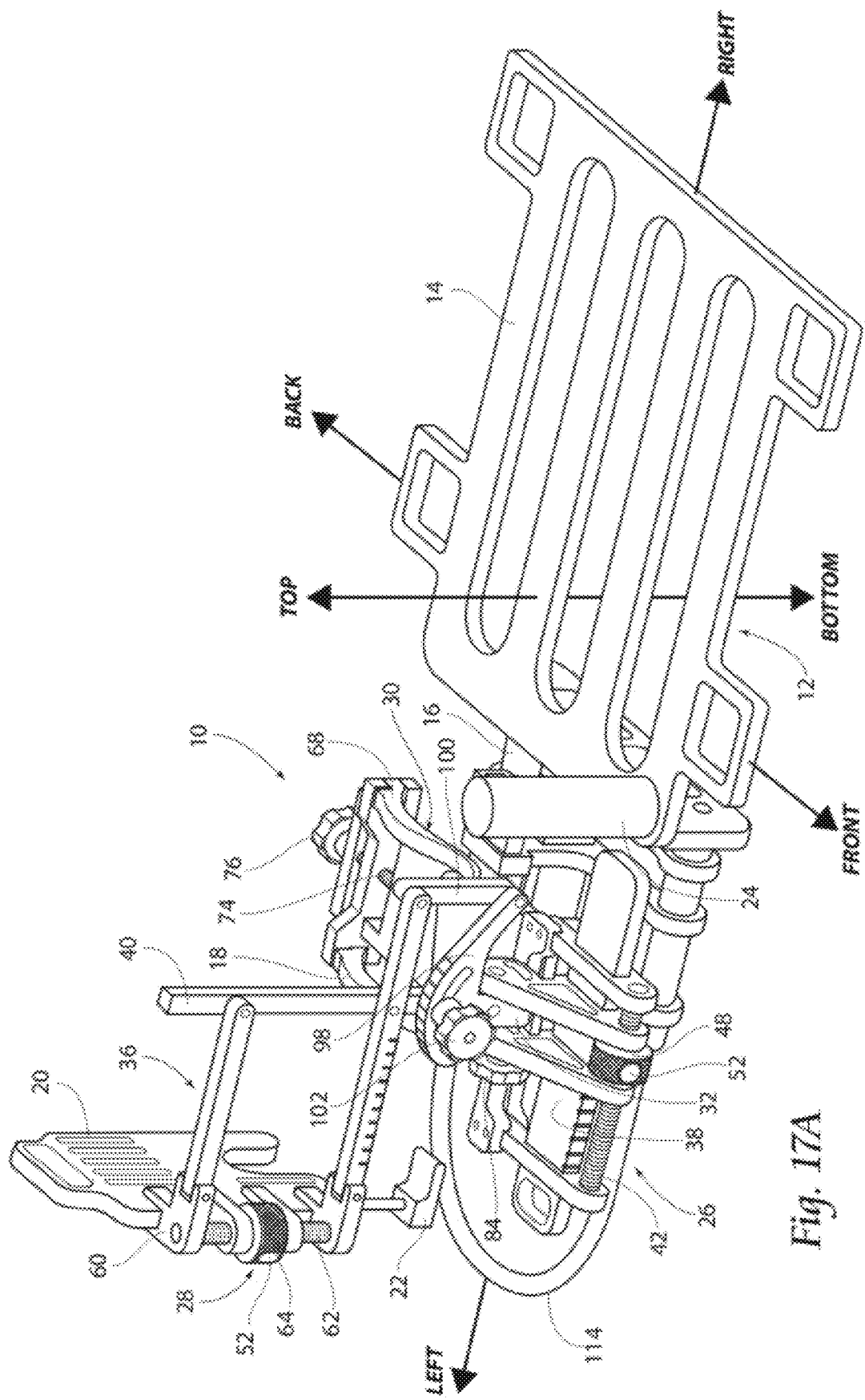
FIGS. 17A to 17F are perspective views of an exemplary system for achieving mechanical force reduction of a bone fracture by the application of force reduction vectors comprising distal traction, superior traction, lateral traction, varus/valgus rotation, pronation/suprination rotation, and flexion/extension.
Figure 17B:
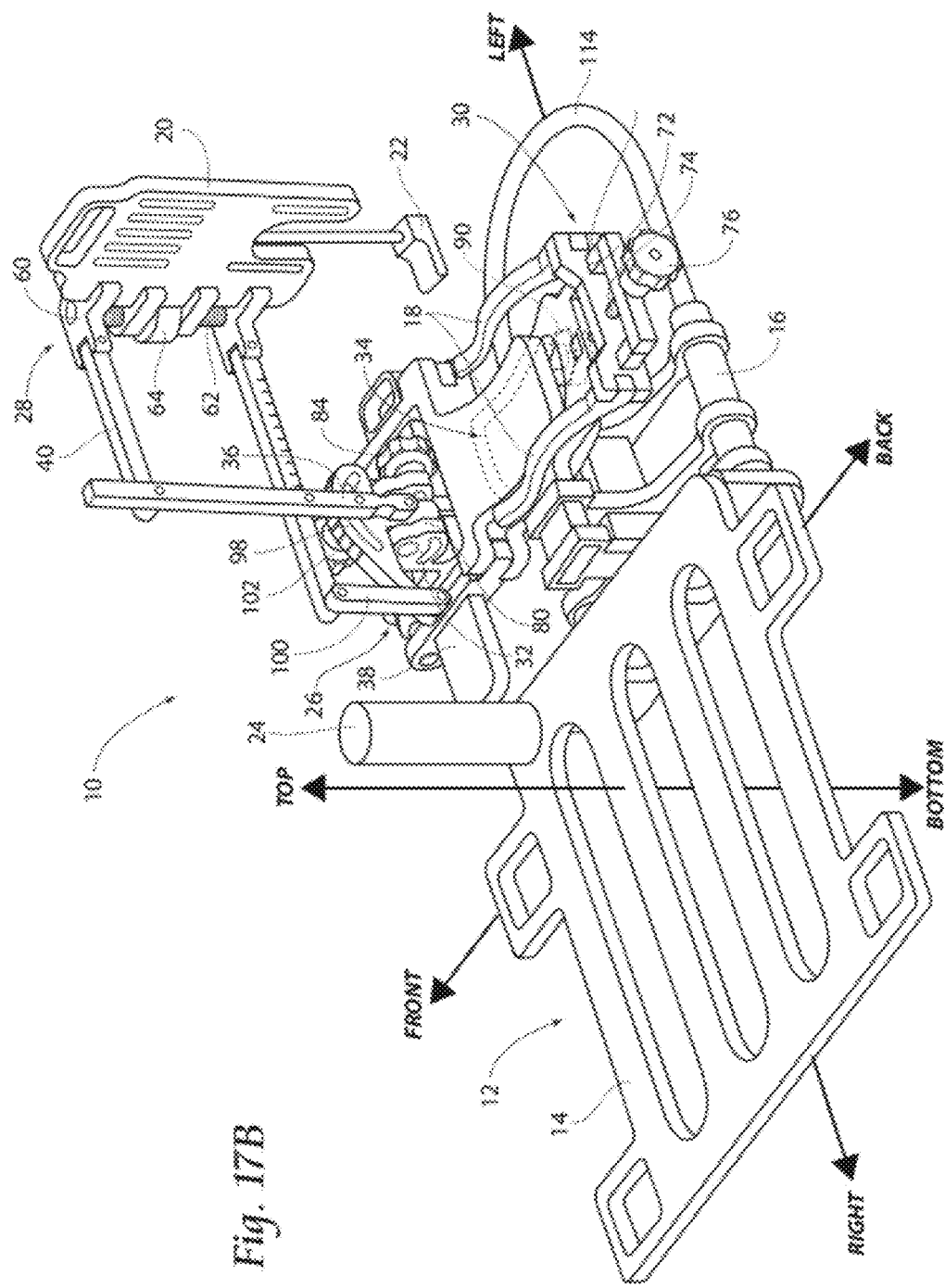

FIGS. 17A and 17B show, respectively, frontward and backward perspective views of an exemplary system 10 sized and configured for achieving a complete, composite reduction of a bone fracture. The system 10 overcomes the problems presented by the dynamic interdependent physical environment of reducing a fracture—which has before now thwarting achievement of a complete composite reduction—by independently applying and maintaining a plurality of disparate force reduction vectors concurrently along disparate axes. The technical features and benefits of the system 10 will be described in the context of reducing a supracondylar fracture, but the technical features that will be described are applicable to reducing bone fractures, simple or complex, of all bone types, in children or adults.

The system 10 achieves a mechanical force reduction of the fracture. The term "mechanical force reduction" means a reduction of a bone fracture by the application of mechanical force, which will also sometimes be called a "mechanical force vector" or a "force reduction vector."

As used herein, the terms "mechanical" and "mechanism" broadly connote the presence of one or more tools or instruments that generate and transform the direction or magnitude of a force to reduce a bone fracture by applying kinetic energy and/or electrical energy and/or pneumatic energy and/or hydraulic energy and/or chemical energy, and/or thermal energy, and/or elastic energy, and combinations thereof. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that generates/applies force to reduce a bone fracture that includes, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

Mechanical force reduction achieves, for the first time, a complete, composite reduction of a bone fracture by independently applying and maintaining force reduction vectors in a mechanical way concurrently along different axes.

As an overview, in a representative implementation, the system 10 applies at least two external, mechanically generated forces to a bone fracture. One of the external mechanically generated forces comprises a first mechanical force vector that moves a bone fracture into alignment in a first anatomic orientation. The system 10 further mechanically maintains a desired alignment in the first anatomic orientation. The system 10 applies another external, mechanically generated force, independent of the first mechanical force vector, comprising a second mechanical force vector. The second mechanical force vector moves the bone fracture into alignment in a second anatomic orientation different than the first anatomic orientation. Because the system 10 mechanically maintains a desired alignment in the first anatomic orientation while applying the second mechanical force vector, alignment in a second anatomic orientation is achieved without altering the desired alignment in the first desired orientation.

In this way, the system 10 mechanically applies a given mechanical force vector to achieve alignment in a first anatomic orientation, and while mechanically maintaining the alignment achieved in the first anatomic orientation, proceeds to apply another mechanical force vector to achieve alignment in another anatomic orientation, and then mechanically maintains that alignment, and so on, until all desired alignments in all identified anatomic orientations are made, to form a composite reduction. At that time, the system 10 can provide systematic mechanical bone fixing of the composite reduction, as will be described in greater detail later.

In the context of treating a supracondylar fracture, and as will be described in greater detail, the system 10 is capable of applying mechanical force reduction in all six possible anatomic reduction orientations. As previously described, the six mechanical force reductions for a supracondylar fracture comprise reduction by (i) distal traction (previously exemplified in FIGS. 11A to 11D); (ii) superior traction (previously exemplified in FIGS. 12A to 12D); (iii) lateral traction (previously exemplified in FIGS. 13A to 13D); (iv) varus/valgus rotation (previously exemplified in FIGS. 14A to 14D); (v) pronation/supination rotation (previously exemplified in FIGS. 15A to 15D); and (vi) flexion/extension rotation (previously exemplified in FIGS. 16A to 16D). In this way, the system 10 makes possible, for the first time, a mechanically-achieved complete composite reduction of a supracondylar fracture.

The system 10 can be variously constructed to achieve this objective. Exemplary structural embodiments will now be described.

C. First Exemplary Embodiment

1. The Reduction Frame

In the exemplary embodiment shown in FIGS. 17A and 17B, the system 10 comprises a reduction frame 12, shown respectively in frontward and backward perspective views. FIGS. 17A and 17B have been annotated to establish baseline directional points of reference for the reduction frame 12 from a structural standpoint, which will be referred to in subsequent description. FIGS. 17A and 17B establish, for the reduction frame 12, the baseline direction points of reference from a structural standpoint, called Front, Back, Left, Right, Top and Bottom, based upon the structural orientation of the reduction frame 12 as shown in FIGS. 17A and 17B. That is, the Front, Back, Left, and Right directional points of reference are relative to the structural orientation of the reduction frame 12 shown in FIGS. 17A and 17B, and not necessarily to the orientation of the reduction frame 12 when in use. The Top and Bottom points of reference do, however, reflect the orientation of the reduction frame 12, as intended, when in use.

Figure 17C:
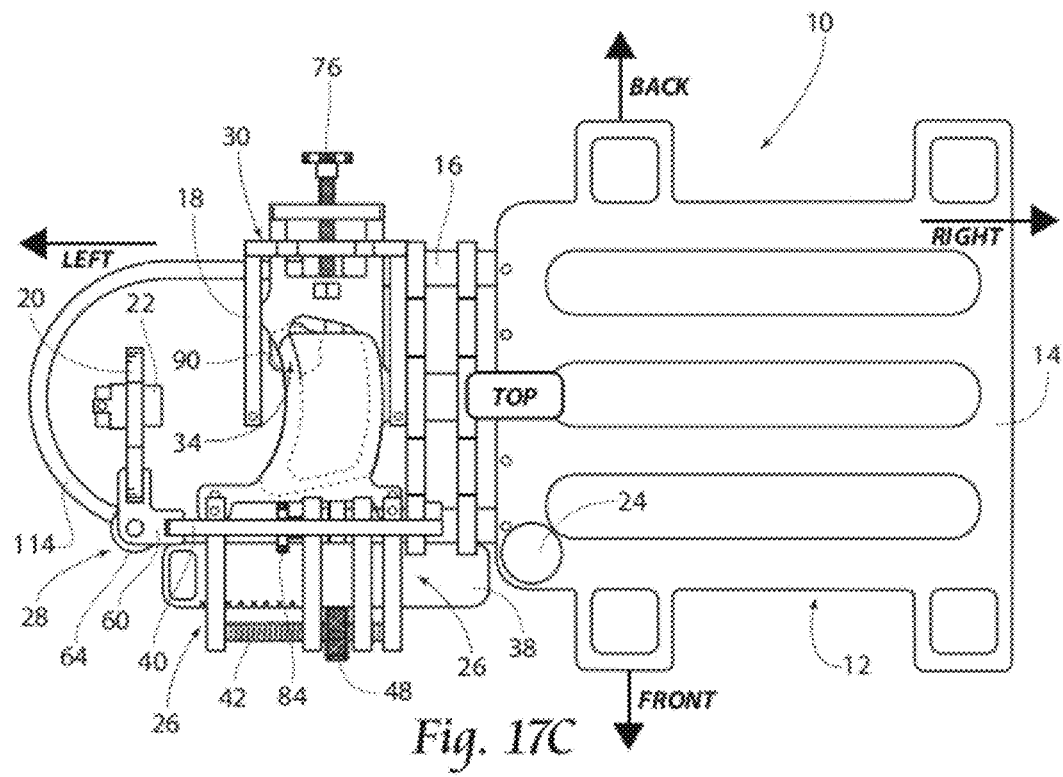
Figure 17D:
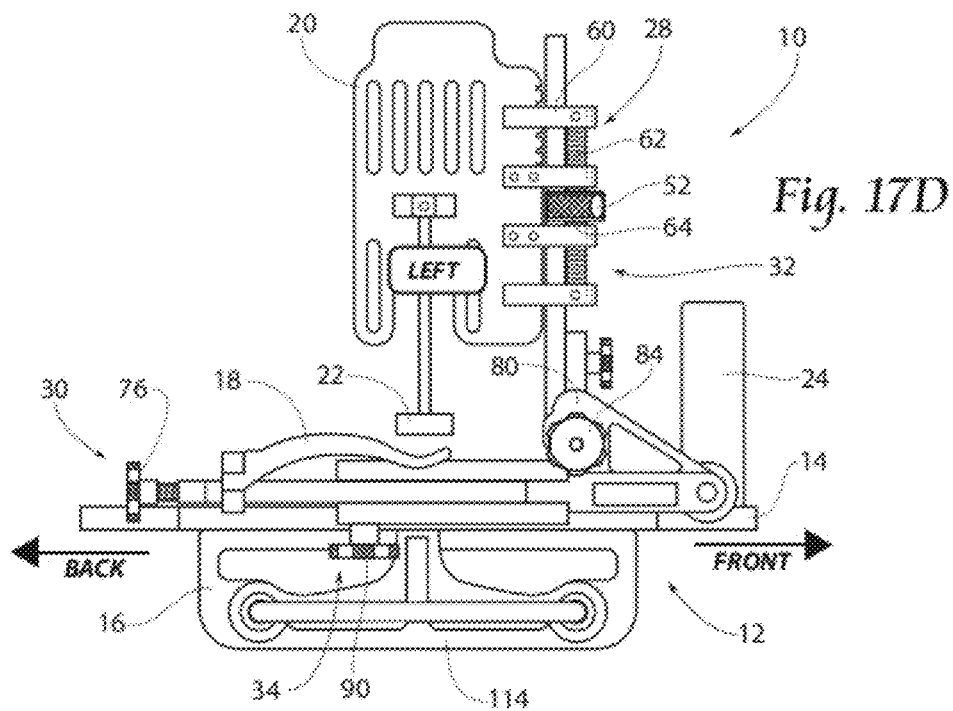
Figure 17E:
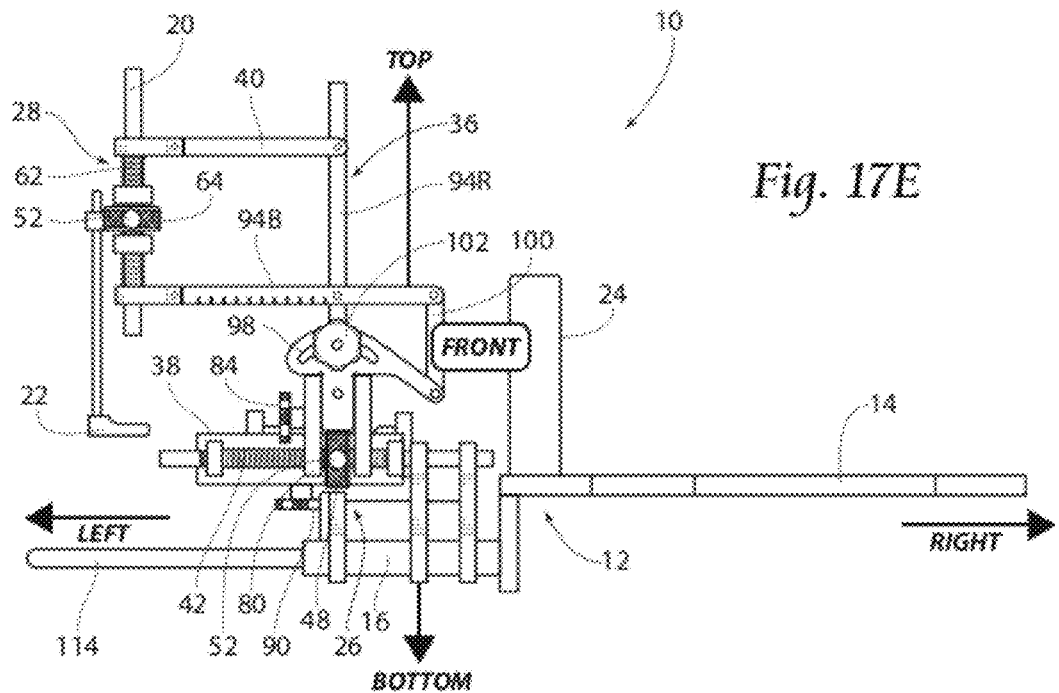

These directional points of reference established for FIGS. 17A and 17B are also carried into companion FIGS. 17C to 17F. FIG. 17C shows the reduction frame 12 in a top plane view (from the Top of FIGS. 17A and 17B); FIG. 17D shows the reduction frame 12 in a left side view, (from the Left of FIGS. 17A and 17B); FIG. 17E which shows the reduction frame 12 in a front view (from the FRONT of FIGS. 17A and 17B); and FIG. 17F, which shows the reduction frame 12 in a back view (from the Back of FIGS. 17A and 17B).

The reduction frame 12 can be fabricated from durable machined metal parts, which can be assembled in conventional fashion, e.g., by fasteners and/or welding.

The reduction frame 12 includes a torso support platform 14 and an appendage support platform 16.

The torso support platform 14 is sized and configured to comfortably support the upper torso of the individual to be treated, at rest in a supine (on the back) position. The torso support platform 14 can be sized and configured to support an adult's upper torso or a child's upper torso. In the illustrated embodiment, the torso support platform 14 is sized and configured for treatment of a child. This is also shown in later FIG. 46.

The appendage support platform 16 is sized and configured to comfortably support the appendage of the individual having the fracture that is to be reduced. In the illustrated embodiment, the appendage is an arm having a supracondylar fracture. The appendage support platform 16 can be sized and configured to support an adult's arm or a child's arm. In the illustrated embodiment, the appendage support platform 16 is sized and configured for treatment of a child. This is also shown later in FIG. 46.

In this arrangement, the appendage support platform 16 includes (on the LEFT of the reduction frame 12) a humeral support carriage 18 and a radius/ulna support carriage 20. The humeral support carriage 18 is secured to the humerus to hold the humerus in a laterally extended position from the shoulder. The radius/ulna support carriage 20 is secured to the radius/ulna to hold the radius/ulna while flexed at the elbow to point the hand in a superior direction facing the shoulder. A support ledge 22 projects from the bottom of the radius/ulna support carriage 20 to provide vertical support the lower region of the distal fracture fragment. A support ledge 22 can be made adjustable to accommodate different size anatomies.

In the illustrated embodiment, a support post 24 extends in a superior direction from the main appendage support platform 16 (on the FRONT of the reduction frame 12). When the individual's upper torso is resting on the torso support platform 14, with their arm properly oriented and resting in the humeral support carriage 18 and the radius/ulna support carriage 20, the individual's underarm rests against the support post 24. The support post 24 horizontally stabilizes the individual's upper torso at rest on the torso support platform 14, with their arm properly oriented in the humeral support carriage 18 and the radius/ulna support carriage 20 for reduction. The support post 24 can take other forms, e.g., an adjustable strap or position-adjustable pillars or columns.

Further stabilization for the individual's entire upper torso can be provided, as desired, by straps across the supine torso fitted to the main torso support platform 14.

2. Mechanical Force Reduction Assemblies

The reduction frame 12 further includes a plurality of mechanical force reduction assemblies. The mechanical force reduction assemblies are carried by the appendage support platform 16 in a prescribed mechanical association with the humeral support carriage 18 and the radius/ulna support carriage 20.

Each of the mechanical force reduction assemblies is sized and configured to independently mechanically manipulate the arm resting in the humeral support carriage 18 and the radius/ulna support carriage 20. Each mechanical force reduction assembly functions independently of the other mechanical force reduction assemblies, to independently apply and maintain one of the prescribed mechanical reduction forces to the fracture. Concurrently, the mechanical force reduction assemblies mechanically apply and maintain a plurality of independent mechanical reduction forces, to thereby mechanically reduce the fracture in the desired reduction planes.

In the context of reducing a supracondylar fracture, there are six mechanical force reduction assemblies. The six mechanical force reduction assemblies correspond to six mechanical force reductions identified for a supracondylar fracture. In this context, the mechanical force reduction assemblies carried by the main appendage support platform 16 comprise (i) a distal traction mechanical force reduction assembly 26; (ii) a superior traction mechanical force reduction assembly 28; (iii) a lateral traction mechanical force reduction assembly 30; (iv) a varus/valgus rotation mechanical force reduction assembly 32; (v) a pronation/supination rotation mechanical force reduction assembly 34; and (vi) a flexion/extension rotation mechanical force reduction assembly 36. Concurrently, the six mechanical force reduction assemblies carried by the reduction frame 12 make possible a mechanically-achieved complete composite reduction of a supracondylar fracture.

Further details of each mechanical force reduction assembly will now be described, with reference to the exemplary embodiment shown in FIGS. 17A to 17F.

i. Distal Traction Mechanical Force Reduction Assembly

The distal traction mechanical force reduction assembly 26 mechanically applies and maintains distal traction to the fracture. As before described, and as earlier shown in FIGS. 11A to 11D, distal traction comprises a force vector applied along the anatomic x-axis of the coordinate system of the supracondylar region. Distal traction along the anatomic x-axis separates the distal bone fragment and the proximal fracture fragment so that subsequent force reduction vectors can be applied to return the proximal and distal bone fragments separated and displaced by the fracture back toward the native state of alignment.

a. Mechanically Achieving Distal Traction

In the exemplary embodiment (initially, refer to FIG. 17A) the distal traction mechanical force reduction assembly 26 comprises a horizontal traction carriage 38 carried by the appendage support platform 16. The horizontal traction carriage 38 is structurally coupled to the radius/ulna support carriage 20 by a scaffold structure 40, as will be more fully described in greater detail later. The horizontal traction carriage 38 and the scaffold structure 40 that mechanically couples it to the radius/ulna support carriage 20, shown in FIG. 17A, are further shaded for identification in FIG. 18A, which (like its companion FIGS. 18B and 18C) also incorporates the directional points of reference established in FIG. 17A.

With reference still to FIGS. 17A and 18A, it can be seen that the horizontal traction carriage 38 is movable in a linear path in a horizontal plane on a horizontal rail 42 along the Front of the appendage support platform 16 in a Left direction (Left-ward) and Right direction (Right-ward). Since the radius/ulna support carriage 20 is structurally coupled by the scaffold structure 40 to the horizontal traction carriage 38, linear movement of the horizontal traction carriage 38 Left-ward and Right-ward likewise linear moves the radius/ulna support carriage 20 in the same Left-ward and Right-ward paths in the horizontal plane. Linear movement can also be considered to be "translation."

The humeral support carriage 18 is not coupled to the horizontal traction carriage 38. Thus, the humeral support carriage 18 remains stationary during Left-ward and Right-ward linear movement of the horizontal traction carriage 38. As a result, linear Left-ward and Right-ward movement of the horizontal traction carriage 38 moves the radius/ulna support carriage 20 in a linear path Left-ward and Right-ward, i.e., laterally closer to or farther from the humeral support carriage 18 (as FIGS. 18B and 18C show).

Figure 18B:
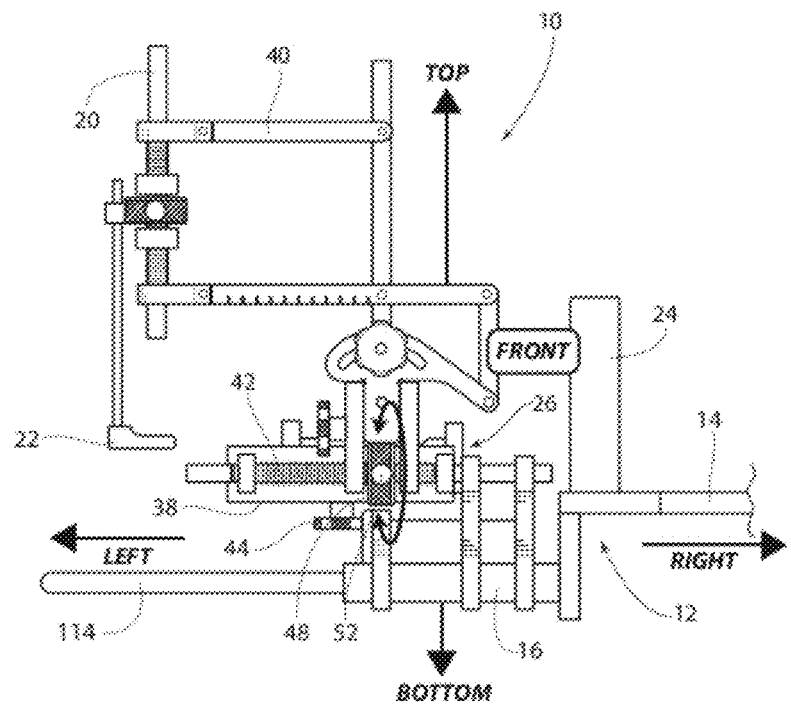
Figure 18C:
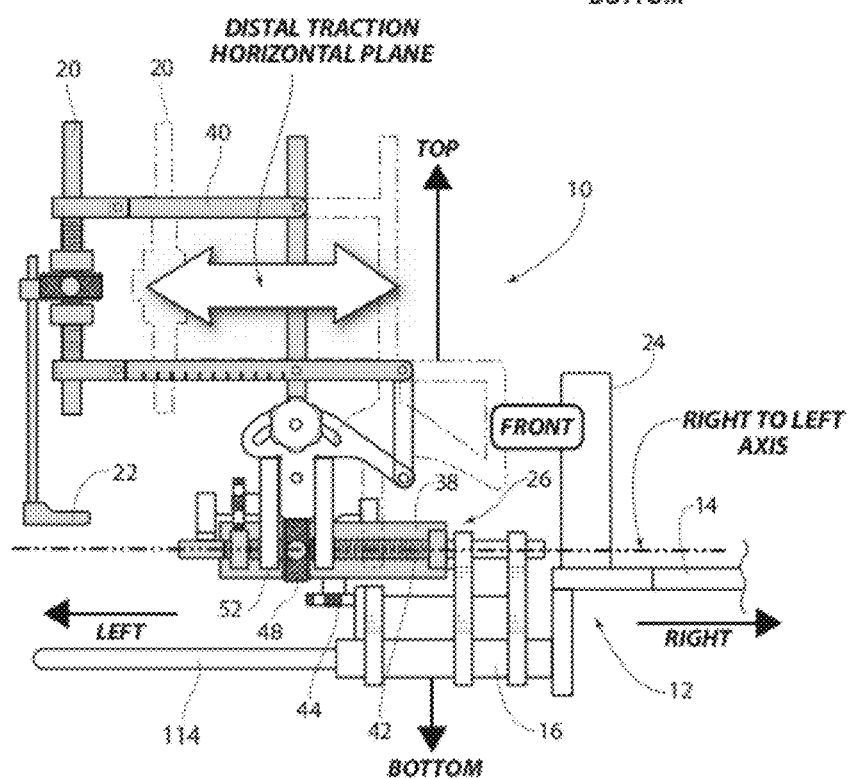

The distal traction mechanical force reduction assembly 26 mechanically achieves distal traction along the anatomic x-axis of the coordinate system of the supracondylar region, by moving the horizontal traction carriage 38 Left-ward in a horizontal plane along the horizontal rail 42 (see FIGS. 18B and 18C). This is because moving the horizontal traction carriage 38 Left-ward in a horizontal plane along the horizontal rail 42 also moves the radius/ulna support carriage 20, which holds the distal bone fragment, in a linear path Left-ward, i.e., farther away from the then-stationary humeral support carriage 18, which holds the proximal bone fragment, thereby separating the distal bone fragment and the proximal bone fragment along the anatomic x-axis (as FIG. 11C shows).

b. Mechanically Maintaining Distal Traction

The distal traction mechanical force reduction assembly 26 includes a distal traction locking mechanism 44. The distal traction locking mechanism 44 can be best seen in FIGS. 17E, 18B, and 18C. In this implementation, the distal traction locking mechanism 44 comprises a threaded locking pin 46 that is advanced by rotation in one direction into frictional engagement against the Bottom of the horizontal traction carriage 38. The frictional engagement holds the then-present position of the horizontal traction carriage 38, to maintain the then-present degree of distal reduction.

The distal traction locking pin 46 is retracted by rotation in an opposite direction out of frictional engagement against the Bottom of the horizontal traction carriage 38. The lack of frictional engagement allows linear Left-ward and/or Right-ward movement of the horizontal traction carriage 38 freely along the horizontal rail 42, to apply a distal mechanical reduction force until a desired degree of distal reduction is achieved.

c. Mechanical Macro and Micro Control of Distal Traction

In the exemplary embodiment, when frictional engagement between the distal traction locking pin 46 and the horizontal traction carriage 38 is withdrawn, the pace of lateral movement of the horizontal traction carriage 38 along the horizontal rail 42 can be selectively controlled by the caregiver, either in a macro-condition or in a micro-condition.

In the macro-condition, free linear movement along the horizontal rail 42 is allowed in response to force manually applied by a caregiver to the radius/ulna support carriage 20.

In the micro-condition, incremental linear movement Left or Right along the horizontal rail 42 occurs in response to the incremental rotation of a distal traction controller 48. The distal traction controller 48 is shown in FIGS. 17A, 18B, and 18C. The distal traction controller 48 makes possible the fine adjustment of linear Left-ward and Right-ward translation of the horizontal traction carriage 38 along the horizontal rail 42.

In the exemplary embodiment, the caregiver is able to select by manipulation of the distal traction controller 48 which condition, macro or micro, is operative.

Details of an exemplary embodiment of the distal traction controller 48 are shown in FIGS. 24 and 25A to 25C. As FIG. 17A shows, the horizontal rail 42 along which the horizontal traction carriage 38 translates includes a threaded surface. The threaded surface includes helical threads that are sized and configured to advance the horizontal traction carriage 38 in small linear increments in response to rotation of the distal traction controller 48.

The distal traction controller 48 takes the form of a cylindrical control knob (see FIG. 17A) mounted for rotation on the horizontal traction carriage 38. As is shown in FIG. 24B, the control knob 48 includes an annular aperture 50, through which the threaded surface of the horizontal rail 42 passes.

Figure 1:
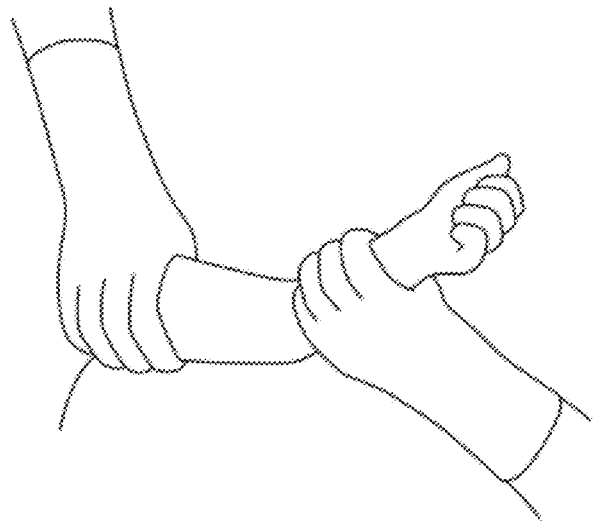
FIGS. 1 to 3 illustrate prior art manual reduction and fixation of a bone fracture.
Figure 2:
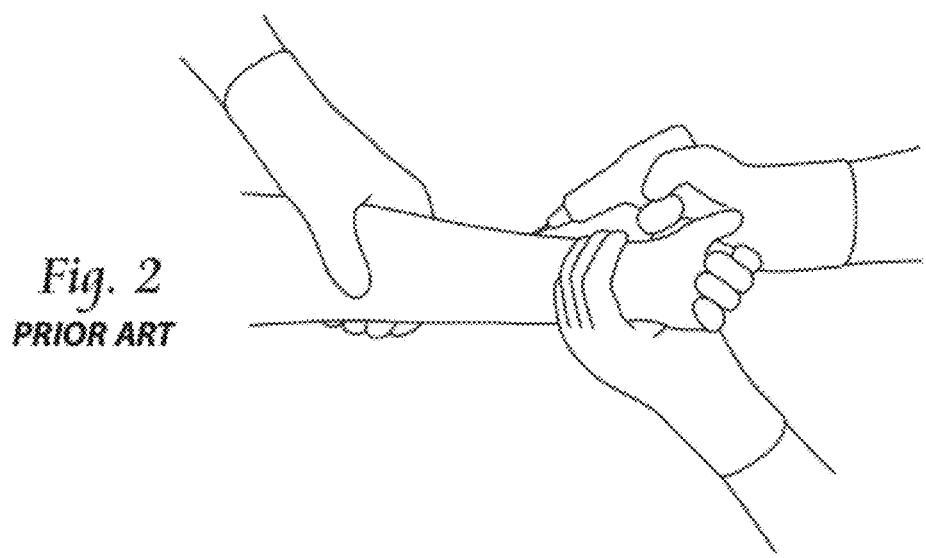
Figure 3:
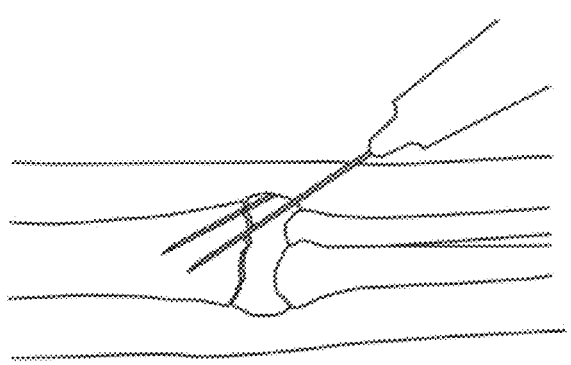
Figure 24A:
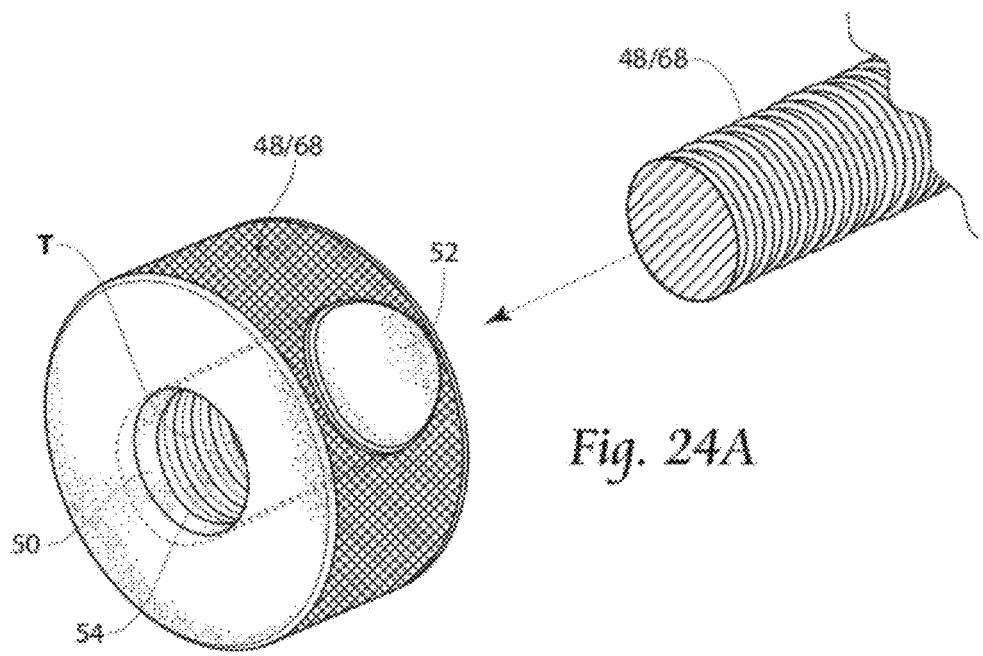
FIGS. 24A and 24B are, respectively, exploded and assembled perspective views of a control knob on the system shown in FIGS. 17A to 17F that provides both macro- and micro-control of mechanical force vectors.
Figure 24B:
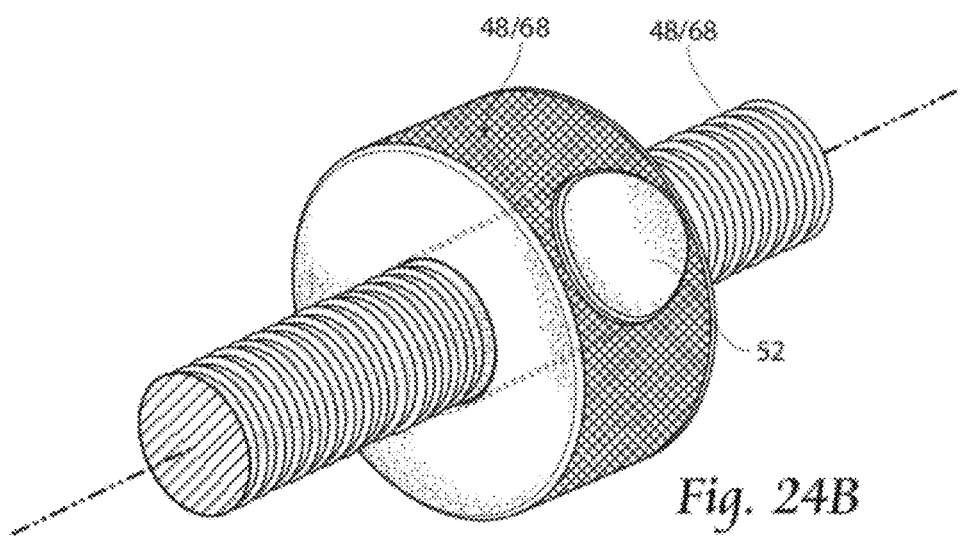

As FIGS. 24A and 24B best show, the controller 48 also includes a translation control pin 52. The translation control pin 52 occupies a radial channel 58 in the control knob 48 (see FIG. 25A). As FIG. 2A shows, the translation control pin 52 includes a bore 54. This is also shown in exploded view in FIG. 25A. In use (as FIG. 24A) shows, the bore 54 is generally axially aligned with the annular aperture 50 of the control knob 48, so that (see FIG. 24B) the threaded surface of the horizontal rail 42 passes through both the bore 54 of the control pin 52 and the annular aperture 50 of the control knob 48.

The bore 54 includes complementary internal screw threads along only a portion of its interior surface (shown in FIGS. 24A and 25A), which are sized and configured to mate with a section of the threaded surface of the horizontal rail 42. The bore 54 of the translation control pin 52 is also slightly larger in interior diameter than the exterior diameter of the threaded surface of the horizontal rail 42, so that, by moving the pin 52 axially along the radial channel 58 of the control knob 48, the threaded interior surface of bore 54 can be brought into and out of the mating contact with the external threaded surface of the horizontal rail 42.

A spring 56 carried within the channel 58 engages the far end of the translation control pin 52 (see FIG. 25A). The spring 56 biases the translation control pin 52 toward a first control position within the channel 58 (see FIG. 25C). In the first control position, the internal screw threads of the control pin 52 mate with a section of threaded surface of the horizontal rail 42. Manual pressure applied to the near end of the translation control pin 52 (see FIG. 25D) moves the translation control pin 52 against the spring force to a second control position within the channel 58. In the second control position, the internal screw threads of the control pin 52 do not engage any section of threaded surface of the horizontal rail 42. Removal of manual pressure on the control pin 52 allows the spring-biased translation control pin 52 to return to the first control position.

Figure 26:
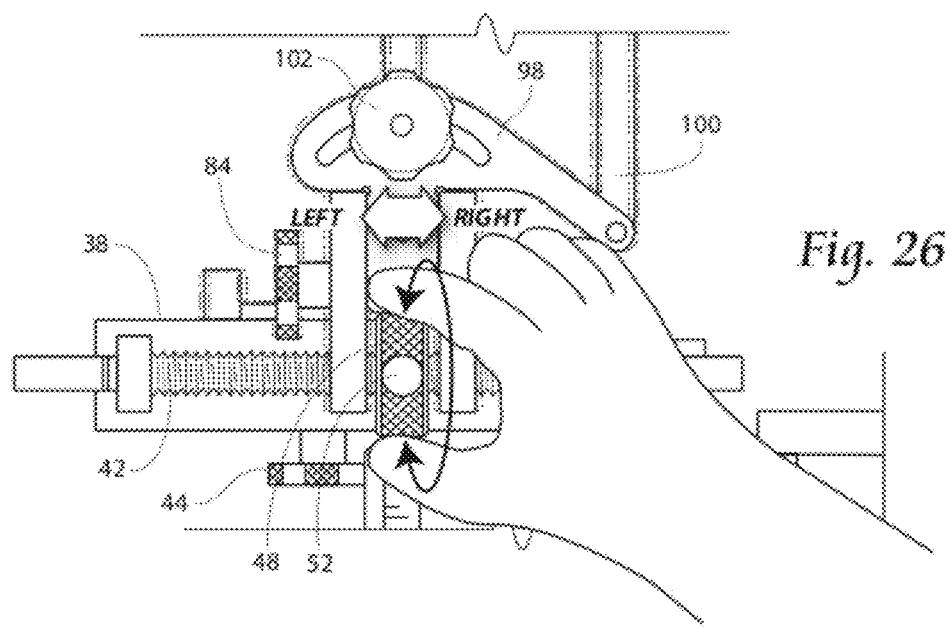
FIGS. 26 and 27 illustrate the operation of the control knob shown in FIGS. 24A and 24B to provide, respectively, micro-control and macro-control of distal traction.

The normally biased first control position of the translation control pin 52 corresponds with the micro-condition above described. As FIG. 26 shows, the normal engagement of the internal screw threads of the translation control pin 52 with the section of threaded surface of the horizontal rail 42 permits incremental fine control over the linear Left-ward and Right-ward movement of the horizontal traction carriage 38 in response to the incremental rotation of the control knob.

Figure 27:
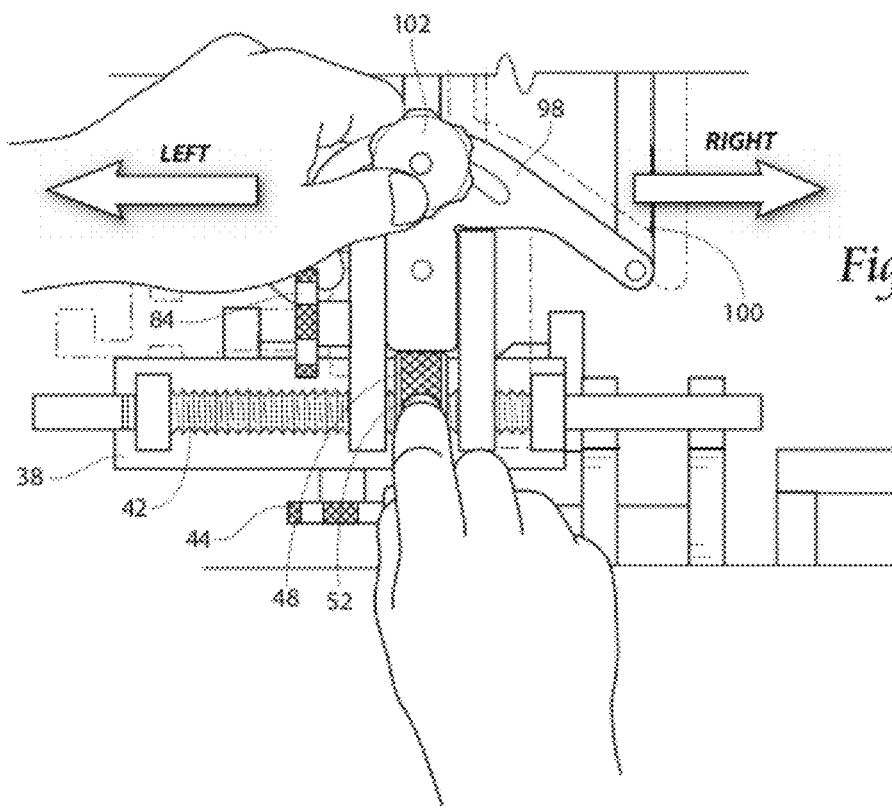

The second control position of the translation control pin 52 corresponds with the macro-condition above described. As FIG. 27 shows, the lack of any engagement of the internal screw threads of the translation control pin 52 with the threaded surface of the horizontal rail 42 frees the horizontal traction carriage 38 for unimpeded translation Left-ward or Right-ward along the horizontal rail 42 by the application by a caregiver of a manual force upon the radius/ulna support carriage 20.

As will be exemplified in greater detail later, the distal traction mechanical force reduction assembly 26 applies either fine (micro) or gross (macro) mechanical force reduction to achieve distal traction, which can be maintained (either by use of the locking pin 46 and/or when in the micro-condition) while other, different mechanical reduction forces are applied by the system 10.

ii. Superior Traction Mechanical Force Reduction Assembly

The superior traction mechanical force reduction assembly 28 mechanically applies and maintains superior traction to the fracture. As before described, and as earlier shown in FIGS. 12A to 12D, superior traction comprises a force vector applied along the anatomic y-axis of the coordinate system of the supracondylar region. Superior traction along the anatomic y-axis lifts (or, in reserve, lowers) the distal bone fragment as a unit relative to the proximal bone fragment, to return proximal and distal bone fragments that have been displaced due to the fracture forward or backwards back (as shown in FIG. 9) toward the native state of alignment.

a. Mechanically Achieving Superior Traction

In the exemplary embodiment (initially, refer to FIG. 17A), the superior traction mechanical force reduction assembly 28 comprises a vertical traction carriage 60 on the appendage support platform 16. The vertical traction carriage 60 is structurally coupled to the radius/ulna support carriage 20 by the same scaffold structure 40 that couples the horizontal traction carriage 38 to the radius/ulna support carriage 20. The vertical traction carriage 60 and the scaffold structure 40 by which it is mechanically coupled to the radius/ulna support carriage 20, shown in FIG. 17A, are further shaded for identification in FIG. 19A, which (like its companion FIGS. 19B and 19C) also incorporates the directional points of reference established in FIG. 17A.

With reference still to FIGS. 17A and 19A, it can be seen that the vertical traction carriage 60 is movable in a linear path in a vertical plane toward the Top (Top-ward) and/or toward the Bottom (Bottom-ward) of the reduction frame 12 on a vertical rail 62 that is carried by the scaffold structure 40. Since the radius/ulna support carriage 20 is structurally coupled to the vertical traction carriage 60, linear Top-ward and/or Bottom-ward movement of the vertical traction carriage 60 likewise moves the radius/ulna support carriage 20 in a linear Top-ward and Bottom-ward path in the vertical plane (see FIG. 19C).

Figure 19B:
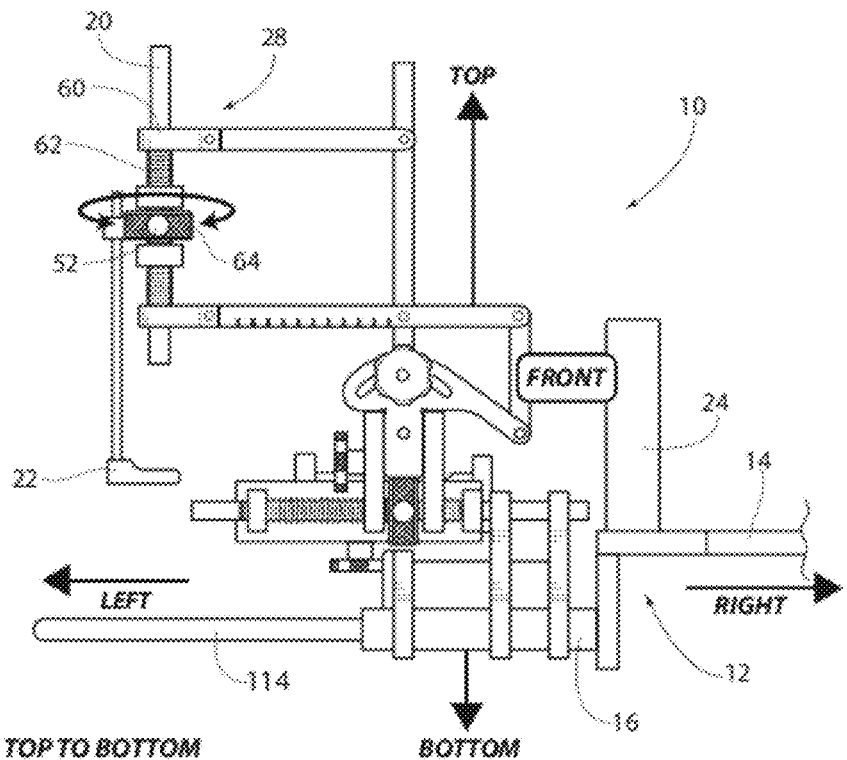
Figure 19C:
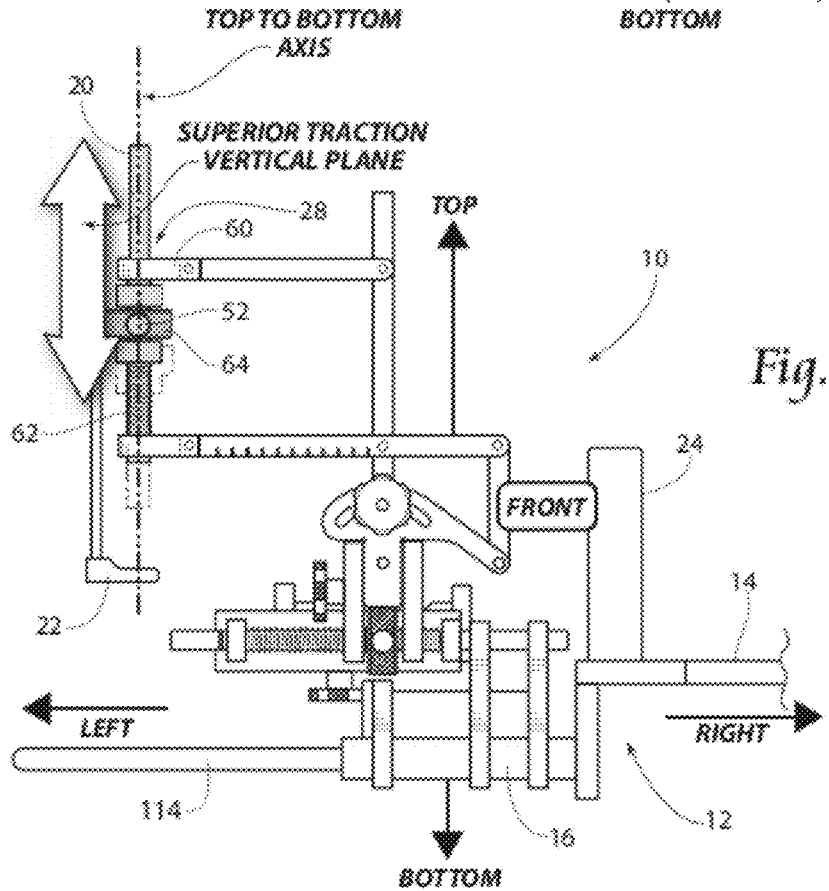

The humeral support carriage 18 is not coupled to the movable vertical traction carriage 60. The humeral support carriage 18 remains stationary during linear Top-ward and Bottom-ward movement of the vertical traction carriage 60. As a result, linear Top-ward and Bottom-ward movement of the vertical traction carriage 60 likewise moves the radius/ulna support carriage 20 in a linear Top-ward and Bottom-ward path in a vertical plane farther from or closer to the humeral support carriage 18 (as FIGS. 19B and 19C show).

The superior traction mechanical force reduction assembly 28 mechanically achieves superior traction along the anatomic y-axis by moving the vertical traction carriage 60 in a vertical plane along the vertical rail 62 in a linear direction Top-ward. This is because moving the vertical traction carriage 60 along the vertical rail 62 in a linear direction Top-ward moves the radius/ulna support carriage 20 (holding the distal bone fragment) in a Top-ward (i.e., superior) direction away from then-stationary humeral support carriage 18 (holding the proximal fracture fragment), thereby separating the distal bone fragment and the proximal fracture fragment along the anatomic y-axis (as FIG. 12C shows).

b. Mechanical Macro and Micro Control of Superior Traction

In the exemplary embodiment, the pace of Top-ward and Bottom-ward movement of the vertical traction carriage 60 along the vertical rail 62 can be selectively controlled either in a macro-condition or in a micro-condition, in the same manner as previously described with respect to the control of the pace of linear Left-ward and Right-ward movement of the horizontal traction carriage 38 of the distal traction mechanical force reduction assembly 26. The caregiver is likewise in the same fashion able to select by manipulation of a superior traction controller 64 (see FIG. 17A and FIGS. 19A to 19C) which condition, macro or micro, is operative. Details of an exemplary embodiment of the distal traction controller 48 are shown in FIGS. 24A/B and 25A/B/C/D, and the same technical features there illustrated are included in the superior traction controller 64.

As an overview, as FIG. 17A shows, the vertical rail 62 along which the vertical traction carriage 60 translates includes a threaded surface. The superior traction controller 64 takes the form of a cylindrical control knob mounted for rotation on the vertical traction carriage 60. The controller 64 also includes a translation control pin 52 movable between a normally biased first control position and a second control position, as previously described in connection with the distal traction controller 48 (and shown in FIGS. 24A and 24B and 25A to 25D.

The first control position corresponds with the micro-condition above described. In the micro-condition, incremental fine control over the superior and inferior movement of the vertical traction carriage 60 is achieved in response to the incremental rotation of the control knob 64.

The second control position of the translation control pin 52 corresponds with the macro-condition above described. In the macro-condition, unimpeded Top-ward and Bottom-ward translation of the vertical traction carriage 60 along the vertical rail 62 is achieved by the application by a caregiver of a manual force upon the radius/ulna support carriage 20.

As will be exemplified in greater detail later, the superior traction mechanical force reduction assembly 28 applies either fine (micro) or gross (macro) mechanical force reduction to achieve superior traction, which can be maintained (while in the micro-condition) while other, different mechanical reduction forces are applied by the system 10.

iii. Lateral Traction Mechanical Force Reduction Assembly

The lateral traction mechanical force reduction assembly 30 mechanically applies and maintains lateral traction to the fracture. As before described, and as earlier shown in FIGS. 13A to 13D, lateral traction comprises a force vector applied along the anatomic z-axis of the coordinate system of the supracondylar region. Lateral traction along the anatomic z-axis moves the fractured end of the distal bone fragments across the fractured end of the proximal bone fragment. Lateral traction returns proximal and distal bone fragments that have been medially displaced left or right due to the fracture (as shown in FIGS. 7 and 8) back toward the native state of alignment.

a. Mechanically Achieving Lateral Traction

In the exemplary embodiment (initially, refer to FIG. 17B), the lateral traction mechanical force reduction assembly 30 comprises a lateral traction carriage 68 on the appendage support platform 16. The lateral traction carriage 68 forms a part of the humeral support carriage 18, previously described. This assembly will therefore sometime be described in shorthand as the "lateral traction-humeral support carriage 18/68." The lateral traction-humeral support carriage 18/68, best shown in FIG. 17B, is further shaded for identification in FIG. 20A, which (like its companion FIGS. 20B and 20C) also incorporates the directional points of reference established in FIG. 17A.

Figure 20A:
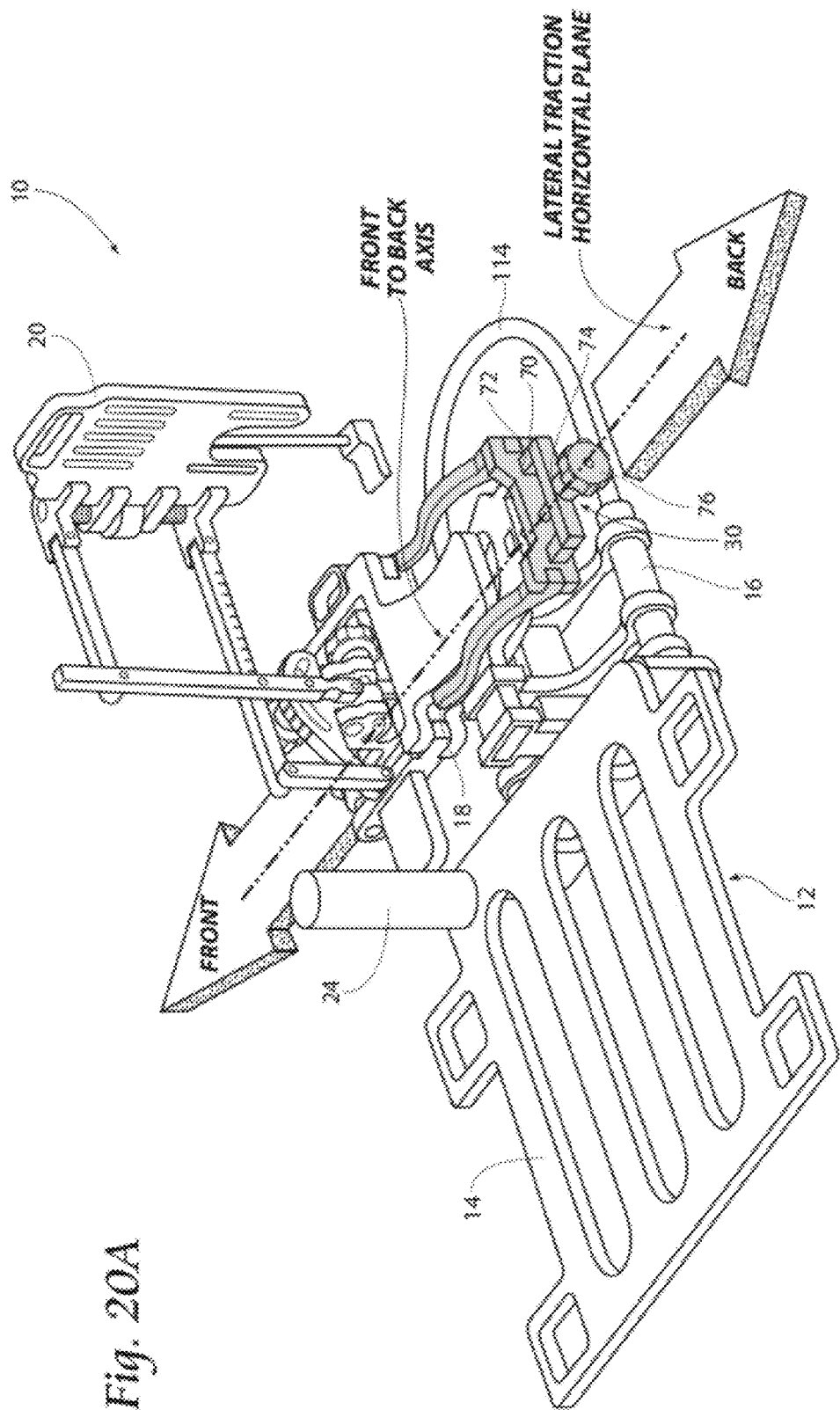
FIGS. 20A to 20C are perspective views of the components of the system shown in FIGS. 17A to 17F that function to achieve lateral traction.

With reference still to FIGS. 17B and 20A, it can be seen that the lateral traction-humeral support carriage 18/68 is carried by rails 70 formed Front to Back in the appendage support platform 16. The rails 70 move within channels 72 to move the lateral traction-humeral support carriage 18/68 in a linear path in a horizontal plane in a Front direction (Front-ward) and a Back direction (Back-ward) on appendage support platform 16.

Figure 20B:
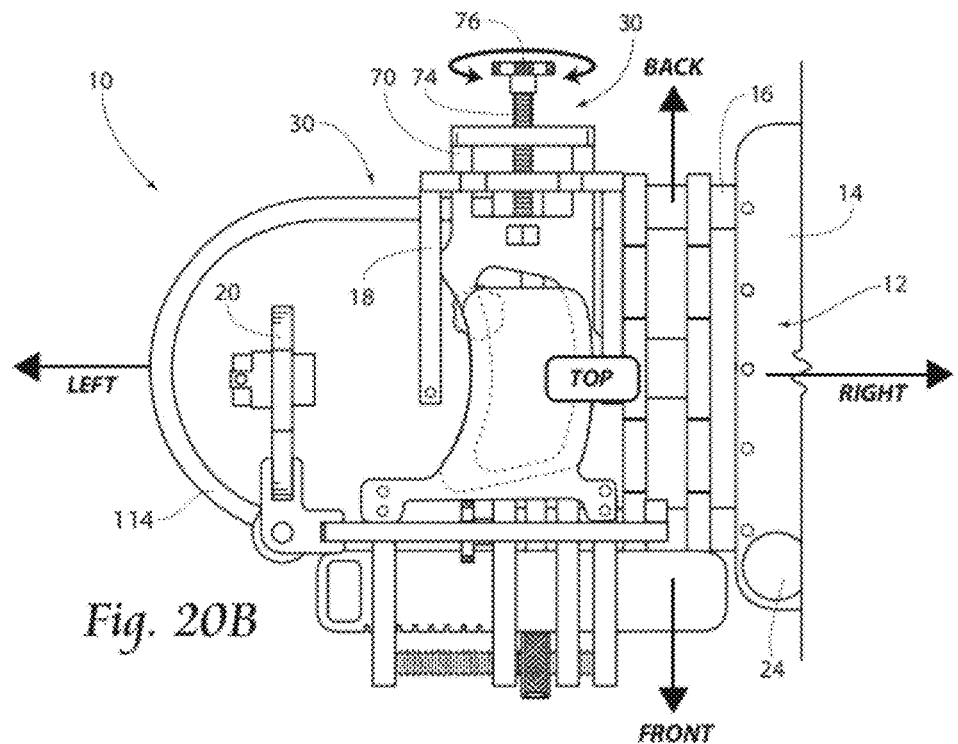

The radius/ulna support carriage 20 is not coupled to the lateral traction-humeral support carriage 18/68. The radius/ulna support carriage 20 remains stationary during linear Front-ward and Back-ward movement of the lateral traction-humeral support carriage 18/68. As a result, linear Front-ward and Back-ward movement of the lateral traction-humeral support carriage 18/68 likewise moves the lateral traction-humeral support carriage 18/68 in a linear Front-ward and Back-ward path in a horizontal plane relative to the radius/ulna support carriage 20 (as FIGS. 20B and 20C show).

Figure 20C:
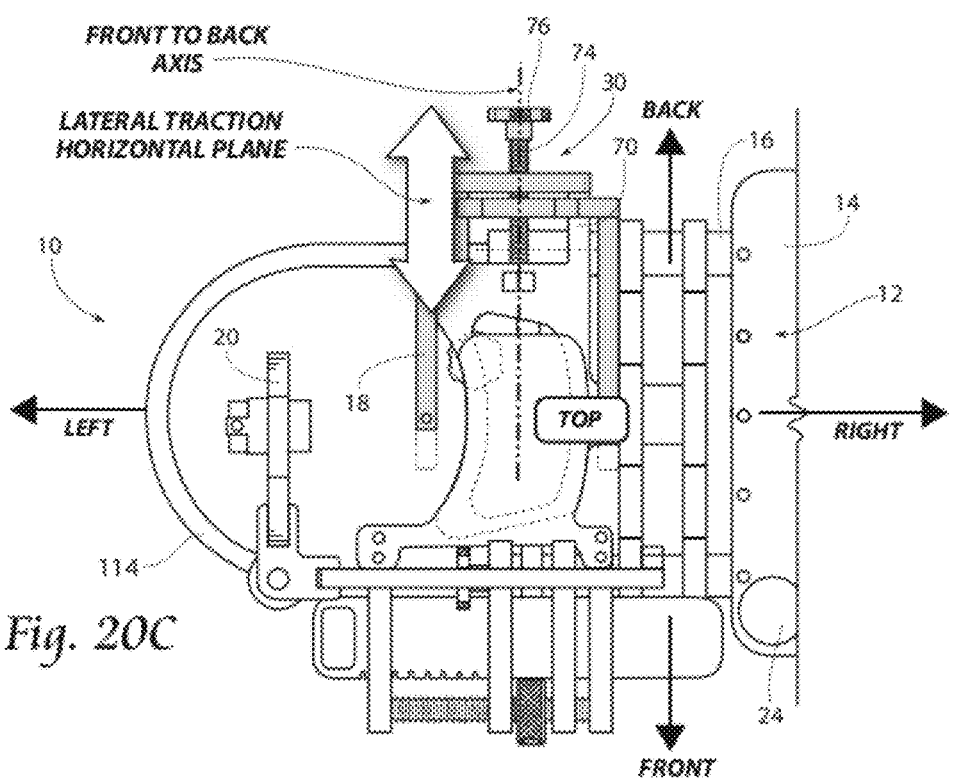

The lateral traction mechanical force reduction assembly 30 mechanically achieves lateral traction along the anatomic z-axis by moving the lateral traction-humeral support carriage 18/68 in a Front-ward and Back-ward path in a horizontal plane (as shown in FIG. 20C). This is because the proximal bone fragment, which is held by the Front-ward and Back-ward moving lateral traction-humeral support carriage 18/68, is moved, respectively, in anatomic anterior and superior directions relative to the distal fracture fragment, which is held in the then-stationary radius/ulna support carriage 20.

The lateral traction mechanical force reduction assembly 30 thereby mechanically returns proximal and distal bone fragments that have been medially displaced along the anatomic z-axis back toward the native state of alignment (as FIG. 13C shows).

b. Micro Control of Lateral Traction

In the exemplary embodiment, the pace of anterior and posterior movement of the lateral traction carriage 68 within the vertical groove is incrementally controlled in a micro-condition. In the exemplary embodiment, there is no macro-condition of lateral traction, as reducing in this plane typically requires only finely controlled, incremental alignment.

As FIGS. 20B and 20C best show, the lateral traction-humeral support carriage 18/68 is operatively coupled to a vertical screw 74 (on the Back of the reduction frame 12) that extends between and parallel to the rails. A control knob 76 is exposed to allow manual rotation of the screw 74 by the caregiver. The screw 74 includes helical threads that are sized and configured to advance the lateral traction-humeral support carriage 18/68 in small linear increments in response to rotation of the screw 74. This provides the micro-condition above described. In the micro-condition, incremental fine control over the linear Front-ward and Back-ward movement of the lateral traction-humeral support carriage 18/68 is achieved in response to the incremental rotation of the control knob 76.

As will be exemplified in greater detail later, the lateral traction mechanical force reduction assembly 30 applies fine (micro) mechanical force reduction to achieve lateral traction, which can be maintained in the micro-condition, while other, different mechanical reduction forces are applied by the system 10.

iv. Varus/Valgus Rotation Mechanical Force Reduction Assembly

The varus/valgus rotation mechanical force reduction assembly 32 mechanically applies and maintains varus/valgus rotation to the fracture. As before described, and as earlier shown in FIGS. 14A to 14D, varus/valgus rotation comprises a rotational force vector (torque) applied about the anatomic x-axis of the coordinate system of the supracondylar region. Varus/valgus rotation about the anatomic x-axis pivots the fractured end of the distal bone fragment about the longitudinal axis of the proximal bone fragment. Varus/valgus rotation returns proximal and distal bone fragments that have been rotationally displaced due to the fracture (as shown in FIG. 10) back toward the native state of alignment.

Varus/valgus rotation serves to bring back into native alignment the posterior, anterior, and medial cortical surfaces along the fracture line.

a. Mechanically Achieving Varus/Valgus Rotation

Figure 21A:
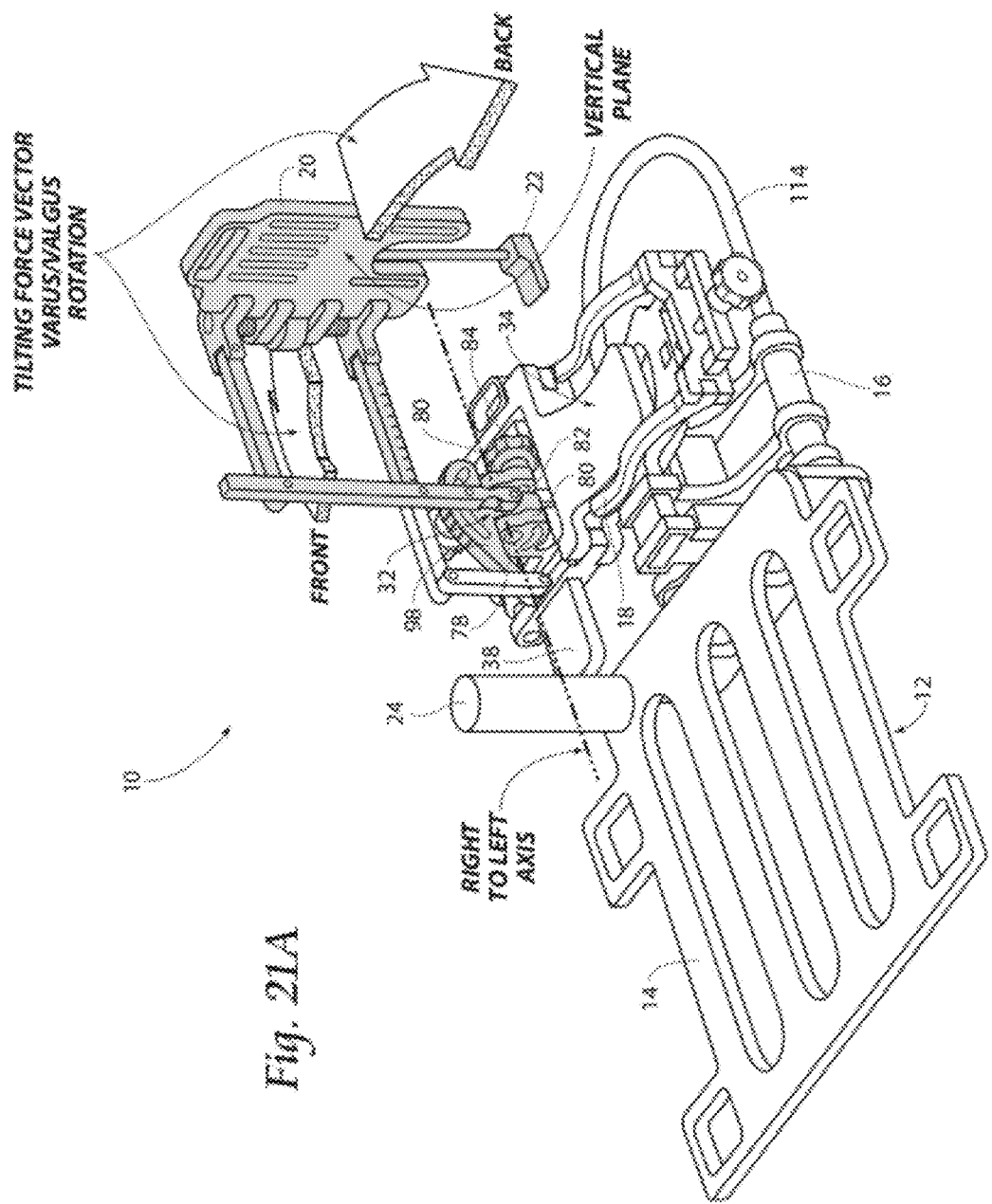
FIGS. 21A to 21C are perspective views of the components of the system shown in FIGS. 17A to 17F that function to achieve varus/valgus rotation.
Figure 21B:
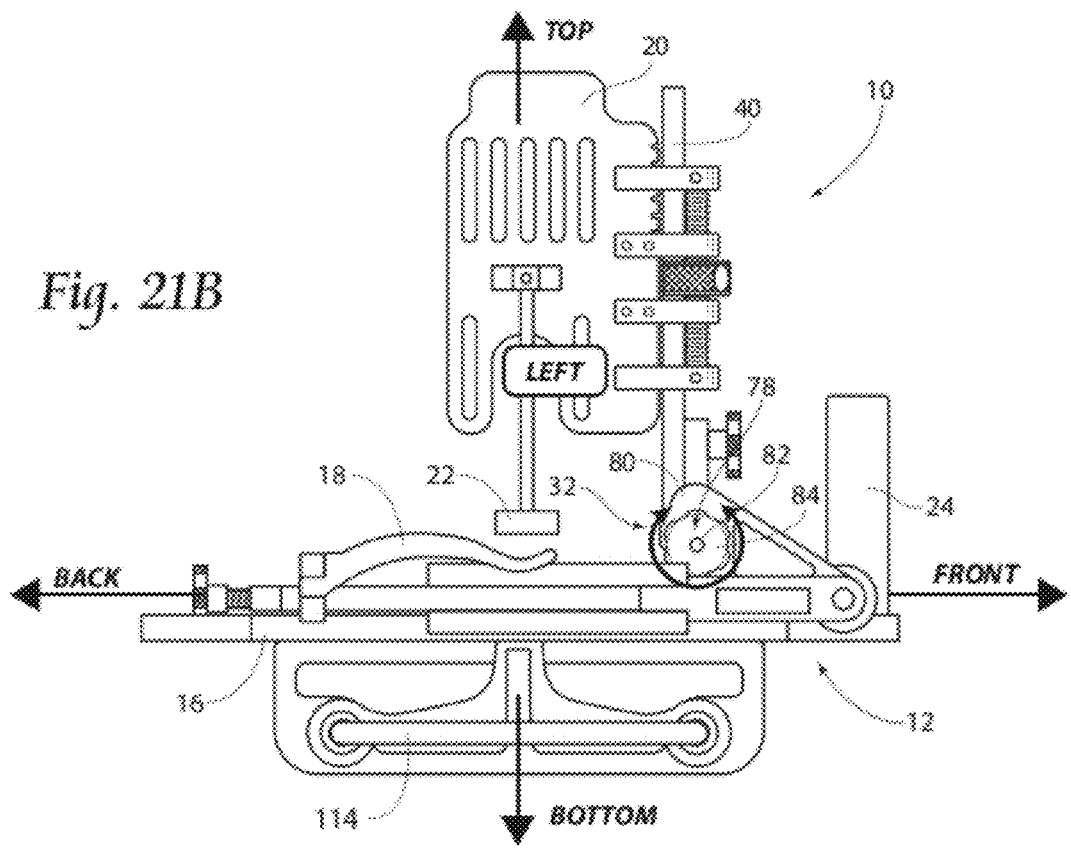

In the exemplary embodiment (initially, refer to FIGS. 17A and 17D), the varus/valgus rotation mechanical force reduction assembly 32 comprises a first pivot point connection system 78 between the horizontal traction carriage 38 and the radius/ulna support carriage 20. The first pivot point connection system 78 pivots about an axis that extends generally Left-to-Right on the reduction frame 12. The first pivot point connection system 78 between the horizontal traction carriage 38 and the radius/ulna support carriage 20, as best shown in FIG. 17D, is further shaded for identification in FIG. 21A, which (like its companion FIGS. 21B and 21C) also incorporates the directional points of reference established in FIG. 17A.

With reference first to FIGS. 17A and 17B, in the exemplary embodiment, the varus/valgus rotation mechanical force reduction assembly 32 comprises a pair of pivot brackets 80 that extend from the TOP of the horizontal traction carriage 38. The brackets 80 on the horizontal traction carriage 38 couple to a Bottom portion of the scaffold structure 40 by a pivot pin 82 (best seen in FIG. 17B). The pivot pin 82 secures the Bottom portion of the scaffold structure 40 to the brackets, thereby also structurally coupling the scaffold structure 40 to the horizontal traction carriage 38. The pivot pin 82 extends along an axis of the reduction frame 12 from Left to Right in FIG. 17A. Since the radius/ulna carriage is coupled to the scaffold structure 40, the pivot pin 82 also structurally couples the radius/ulna support carriage 20 to the horizontal traction carriage 38. The brackets 80 and pivot pin 82 coupled to the scaffold structure 40 therefore comprise the first pivot point connection system 78 between the horizontal traction carriage 38 and the radius/ulna support carriage 20.

Figure 21C:
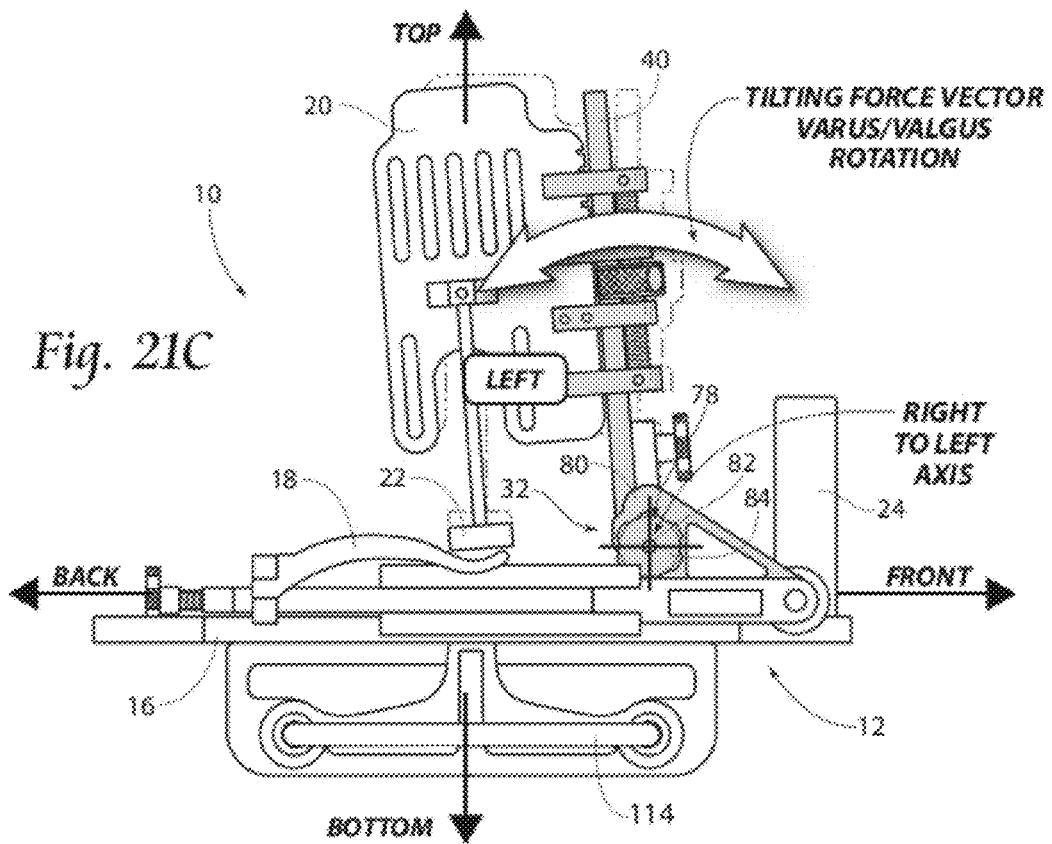

As companion FIG. 21C shows, as a result of the first pivot point connection system 78, the scaffold structure 40 tilts about the Left-to-Right pivot pin axis along an arcuate path in a Back direction (Back-ward) and Front direction (Front-ward) in a vertical plane. Since the radius/ulna support carriage 20 is coupled to the scaffold structure 40, tilting the scaffold structure 40 along this path likewise tilts the radius/ulna support carriage 20 Back-ward and Front-ward about the Left-to-Right pivot pin axis of the reduction frame 12 in vertical plane (see FIG. 21C).

The humeral support carriage 18 is not coupled to the horizontal traction carriage 38 or the scaffold structure 40. The humeral support carriage 18 remains stationary as the radius/ulna support carriage 20 tilts Back-ward and Front-ward about the Left-to-Right pivot pin axis in its arcuate path in the vertical plane. As a result, the radius/ulna support carriage 20 tilts in the vertical plane Front-ward and Back-ward relative to the stationary humeral support carriage 18 (as FIG. 21C shows).

The varus/valgus rotation mechanical force reduction assembly 32 mechanically achieves varus/valgus rotation about the anatomic x-axis by tilting the radius/ulna support carriage 20 in an arcuate path in a vertical plane Front-ward and Back-ward about the Left-to_Right pivot point axis relative to the stationary humeral support carriage 18. As the radius/ulna support carriage 20 tilts Front-ward and Back-ward in the vertical plane relative to stationary humeral support carriage 18, a rotational force vector (torque) is applied about the anatomic x-axis to the fractured end of the distal bone fragment (held in the radius/ulna support carriage 20). The varus/valgus rotation force, mechanically applied by the varus/valgus rotation mechanical force reduction assembly 32, pivots the fractured end of the distal bone fragment about the longitudinal axis of the proximal bone fragment, to return the proximal and distal bone fragments, which have been rotationally displaced due to the fracture (as shown in FIG. 10), back toward the native state of alignment.

c. Mechanically Locking Varus/Valgus Rotation

In the exemplary embodiment, the varus/valgus rotation mechanical force reduction assembly 32 includes a varus/valgus rotation locking mechanism 84. The varus/valgus rotation locking mechanism 84 can be best seen in FIGS. 17A, 17D, 21B, and 21C. In this implementation, the varus/valgus rotation locking mechanism 84 comprises a threaded locking pin that is advanced by rotation in one direction to provide frictional interference with the pivot point connection system 78. Frictional interference maintains the then-present tilted, torque-applying position of the radius/ulna support carriage 20, to maintain the then-present degree of varus/valgus rotation.

The varus/valgus rotation locking mechanism 84 is retracted by rotation in an opposite direction out of frictional interference with the pivot point connection system 78. The lack of frictional interference allows tilting movement of the radius/ulna support carriage 20 Back-ward and Front-ward freely about the first pivot point connection system 78. This corresponds to the previously described macro-condition, which allows the caregiver unimpeded tilting translation of the radius/ulna support carrier Back-ward and Front-ward by the application a manual tilting force upon the radius/ulna support carriage 20. When the desired degree of varus/valgus rotation is achieved, the caregiver operates the varus/valgus rotation locking mechanism 84 to maintain the position.

In the exemplary embodiment, the pace of varus/valgus rotation is incrementally controlled in a macro-condition. In the exemplary embodiment, there is no micro-condition of varus/valgus rotation, as reducing in this plane typically does not require micro-incremental alignment.

As will be exemplified in greater detail later, the varus/valgus rotation mechanical force reduction assembly 32 applies mechanical force reduction to achieve varus/valgus rotational alignment, which can be maintained by the varus/valgus rotation locking mechanism, while other, different mechanical reduction forces are applied by the system 10.

v. Pronation/Supination Rotation Mechanical Force Reduction Assembly

The pronation/supination rotation mechanical force reduction assembly 34 mechanically applies and maintains pronation/supination rotation to the fracture. As before described, and as earlier shown in FIGS. 15A to 15D, pronation/supination rotation comprises a rotational force vector (torque) applied about the anatomic y-axis of the coordinate system of the supracondylar region. Pronation/supination rotation about the anatomic y-axis pivots the fractured end of the distal bone fragment about the longitudinal axis of distal bone fragment. Like varus/valgus rotation, pronation/supination rotation returns proximal and distal bone fragments that have been rotationally displaced due to the fracture (as shown in FIG. 10) back toward the native state of alignment. Pronation/supination rotation also serves to bring back into native alignment the posterior, anterior, and medial cortical surfaces along the fracture line.

a. Mechanically Achieving Pronation/Supination Rotation

In the exemplary embodiment (initially, refer to FIGS. 17B and 17C), the pronation/supination rotation mechanical force reduction assembly 34 comprises a second pivot point connection system 86 between the horizontal traction carriage 38 and the appendage support platform 16. The second pivot point connection system 86 of the pronation/supination rotation mechanical force reduction assembly 34 pivots about an axis that is different than the axis of the first pivot point connection system 78 of the varus/valgus rotation mechanical force reduction assembly 32, which pivotally connects the horizontal traction carriage 38 to the radius/ulna support carriage 20. Whereas the first pivot point connection system 78 pivots about a Left-to-Right axis on the reduction frame 12, the second pivot point connection system 86 establishes a virtual center of rotation for the radius/ulna support carriage 20 (see FIG. 22C) that extends generally Top-to-Bottom on the reduction frame 12. The result is the application of rotational force vectors (torques) that substantially differ. The first pivot point connection system 78 (Left-to-Right axis) generates a tilting force vector in a vertical plane. The second pivot point connection system 86 (Top-to-Bottom axis) generates a swinging force vector in a horizontal plane.

Figure 17F:
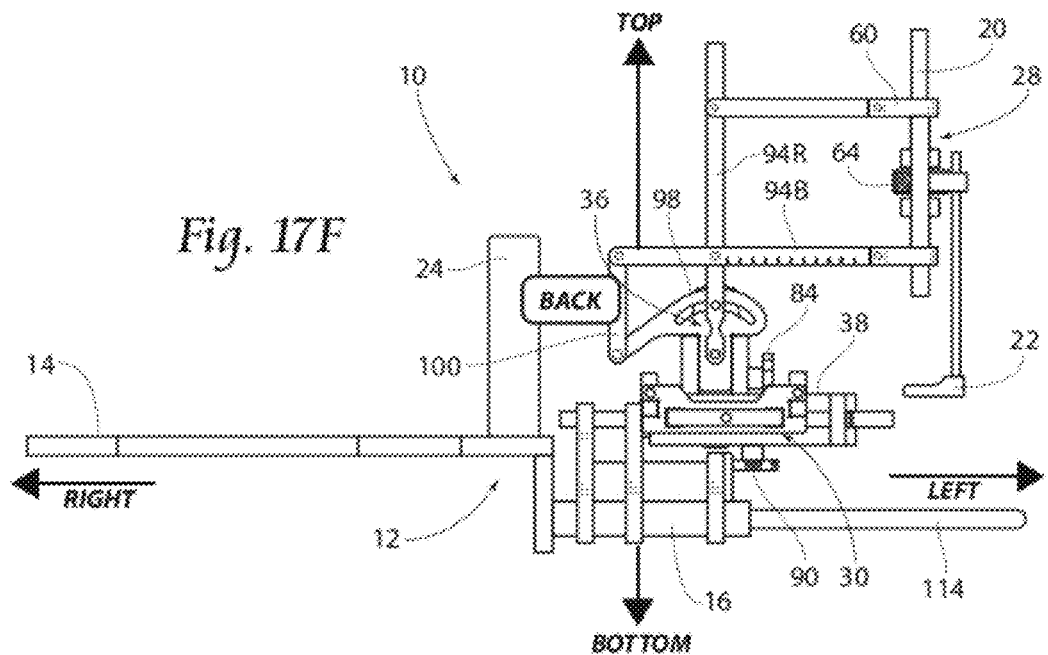
Figure 22B:
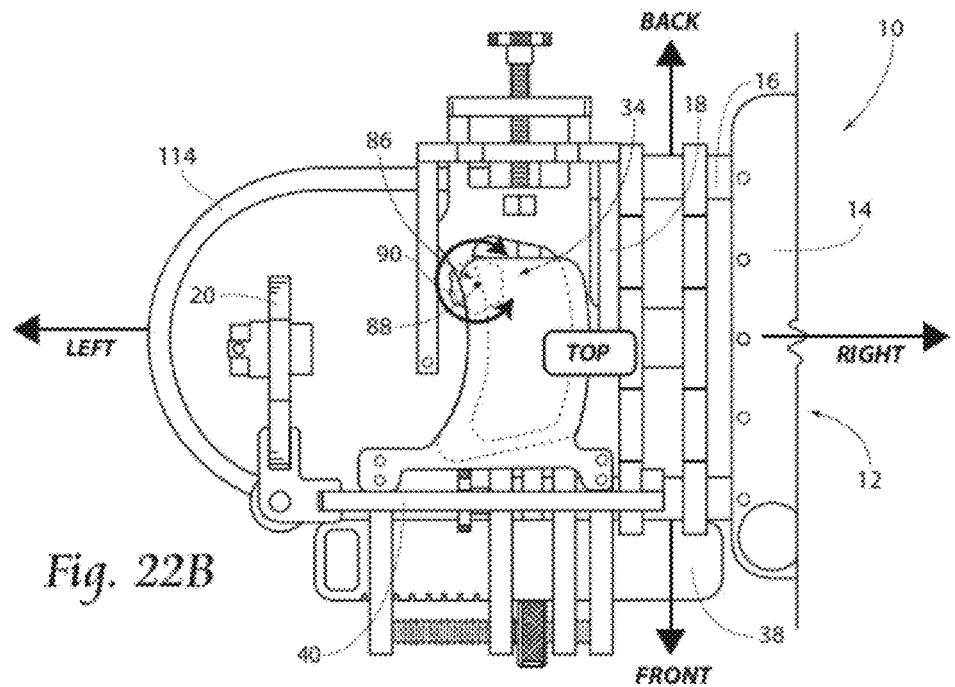

The second pivot point connection system 86 between the horizontal traction carriage 38 and appendage support platform 16, as best shown in FIGS. 17E and 17F, is further shaded for identification in FIG. 22A, which (like its companion FIGS. 22B and 22C) also incorporates the directional points of reference established in FIG. 17A.

With reference first to FIGS. 17E and 17F, in the exemplary embodiment, the second pivot point connection system 86 comprises a pivot pin 88 that pivotally secures the Bottom of the horizontal traction carriage 38 to the appendage support platform 16. The pivot pin 88 extends along an axis of the reduction frame 12 from Top to Bottom in FIGS. 17E and 17F.

Figure 22C:
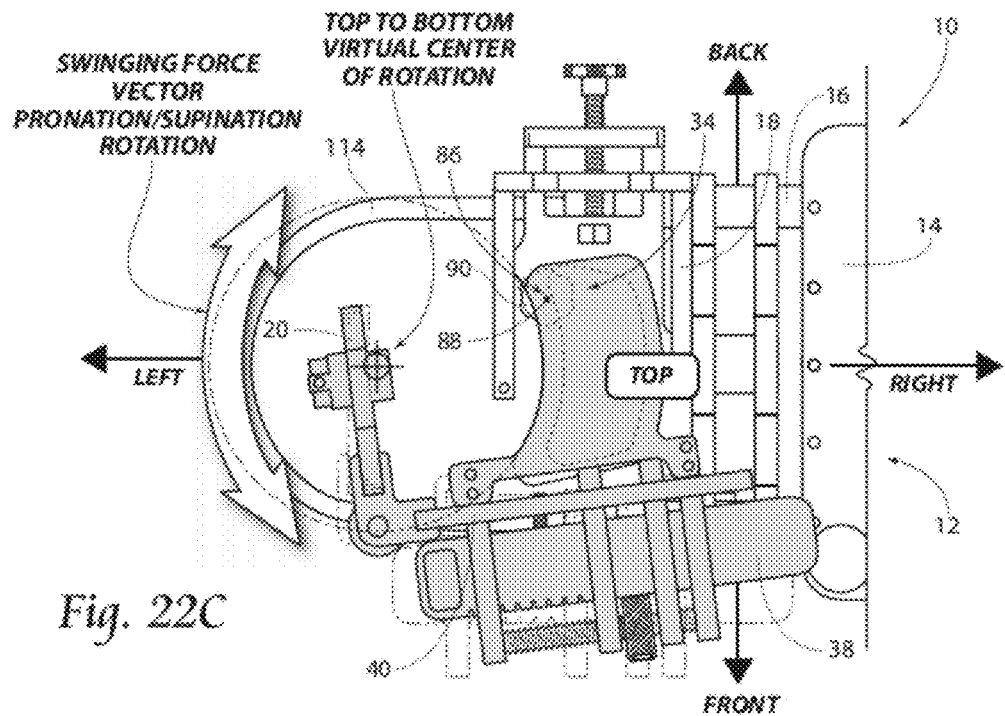

As companion FIG. 22C shows, as a result of the second pivot point connection system 86, the horizontal traction carriage 38 (and thus the scaffold structure 40 coupled to it) swings in a horizontal plane about the Top-to-Bottom virtual center of rotation in an arcuate path in a Back direction (Back-ward) and Front direction (Front-ward). Since the radius/ulna support carriage 20 is coupled to the scaffold structure 40, swinging the scaffold structure 40 along this path likewise swings the radius/ulna carriage in a horizontal plane Back-ward and Front-ward about the Top-to-Bottom virtual center of rotation (see FIG. 22C).

The humeral support carriage 18 is not coupled to the horizontal traction carriage 38 or the scaffold structure 40. The humeral support carriage 18 remains stationary as the radius/ulna support carriage 20 swings in the horizontal plane Back-ward and Front-ward in its arcuate path about the Top-to-Bottom virtual center of rotation axis. As a result, the radius/ulna carriage swings Back-ward and Front-ward relative to the stationary humeral support carriage 18 (as FIG. 22C shows).

The pronation/supination rotation mechanical force reduction assembly 34 mechanically achieves pronation/supination rotation about the anatomic y-axis by swinging the radius/ulna support carriage 20 in an arcuate path in a horizontal plane Front-ward and Back-ward about the Top-to-Bottom virtual center of rotation axis relative to the stationary humeral support carriage 18. As the radius/ulna support carriage 20 swings Front-ward and Back-ward in the horizontal plane about the Top-to-Bottom virtual center of rotation axis relative to stationary humeral support carriage 18, a rotational force vector (torque) is applied about the anatomic y-axis to the fractured end of the distal bone fragment (held in the radius/ulna support carriage 20). The pronation/supination rotation force, mechanically applied by the pronation/supination rotation mechanical force reduction assembly 34, pivots the fractured end of the distal bone fragment about the longitudinal axis of distal bone fragment.

b. Mechanically Locking Pronation/Supination Rotation

In the exemplary embodiment, the pronation/supination rotation mechanical force reduction assembly 34 includes a pronation/supination rotation locking mechanism 90. The pronation/supination rotation locking mechanism 90 can be best seen in FIGS. 17E, 17F, 22B, and 22C. In this implementation, the pronation/supination rotation locking mechanism 90 comprises a threaded locking pin that is advanced by rotation in one direction to provide frictional interference with the second pivot point connection system 86. Frictional interference maintains the then-present torque-applying position of the radius/ulna support carriage 20 in the horizontal plane, to maintain the then-present degree of pronation/supination rotation.

The pronation/supination rotation locking mechanism 90 is retracted by rotation in an opposite direction out of frictional interference with the second pivot point connection system 86. The lack of frictional interference allows swing movement of the radius/ulna support carriage 20 Back-ward and Front-ward in the horizontal plane freely about a virtual center of rotation (extending TOP to BOTTOM and shown in FIG. 22C) established the second pivot point connection system 86. This corresponds to the previously described macrocondition, which allows the caregiver unimpeded swinging translation of the radius/ulna support carrier Back-ward and Front-ward in a horizontal plane by the application a manual swinging force upon the radius/ulna support carriage 20. When the desired degree of pronation/supination rotation is achieved, the caregiver operates the pronation/supination rotation locking mechanism to maintain the position.

In the exemplary embodiment, the pace of pronation/supination rotation is incrementally controlled in a macro-condition. In the exemplary embodiment, there is no micro-condition of pronation/supination rotation, as reducing in this plane typically does not require micro-incremental alignment.

As will be exemplified in greater detail later, the pronation/supination rotation mechanical force reduction assembly 34 applies mechanical force reduction to achieve pronation/supination rotational alignment, which can be maintained by the pronation/supination rotation locking mechanism, while other, different mechanical reduction forces are applied by the system 10.

vi. Flexion/Extension Rotation Mechanical Force Reduction Assembly

The flexion/extension rotation mechanical force reduction assembly 36 mechanically applies and maintains flexion/extension rotation to the fracture. As before described, and as earlier shown in FIGS. 16A to 16D, flexion/extension rotation comprises a rotational force vector (torque) applied about the z-axis. Flexion/extension rotation about the z-axis pivots the fractured end of the distal bone fragment toward the fractured end of the proximal bone fragment. Flexion/extension rotation returns the fractures ends of the proximal and distal bone fragments that have been separated due to the fracture back toward the native state of alignment.

a. Mechanically Achieving Flexion/Extension Rotation

In the exemplary embodiment (initially, refer to FIGS. 17A, 17B, 17E, and 17F), the flexion/extension rotation mechanical force reduction assembly 36 comprises a third pivot point connection system 92 between the horizontal traction carriage 38 and the radius/ulna support carriage 20. The third pivot point connection system 92 pivots about an axis that extends generally Front-to-Back on the reduction frame 12. The third pivot point connection system 92 of the flexion/extension rotation mechanical force reduction assembly 36 pivots about an axis that is different than the axes of both the first pivot point connection system 78 of the varus/valgus rotation mechanical force reduction assembly 32 and the second pivot point connection system 86 of the pronation/supination rotation mechanical force reduction assembly 34. Whereas the first pivot point connection system 78 pivots about a Left-to-Right axis on the reduction frame 12, and the second pivot point connection system 86 pivots about an axis that extends generally Top-to-Bottom on the reduction frame 12, the third pivot point connection system 92 pivots about an axis that extends generally Front-to-Back on the reduction frame 12. The result is the application of rotational force vectors (torques) that substantially differ. The first pivot point connection system 78 (Left-to-Right axis) generates a Front-ward and Back-ward tilting force vector in a vertical plane. The second pivot point connection system 86 (Top-to-Bottom axis) generates a Front-ward and Back-ward swinging force vector in a horizontal plane.

The third pivot point connection system 92 (Front-to-Back axis) generates a Left-ward and Right-ward tilting force vector in a vertical plane.

Figure 23B:
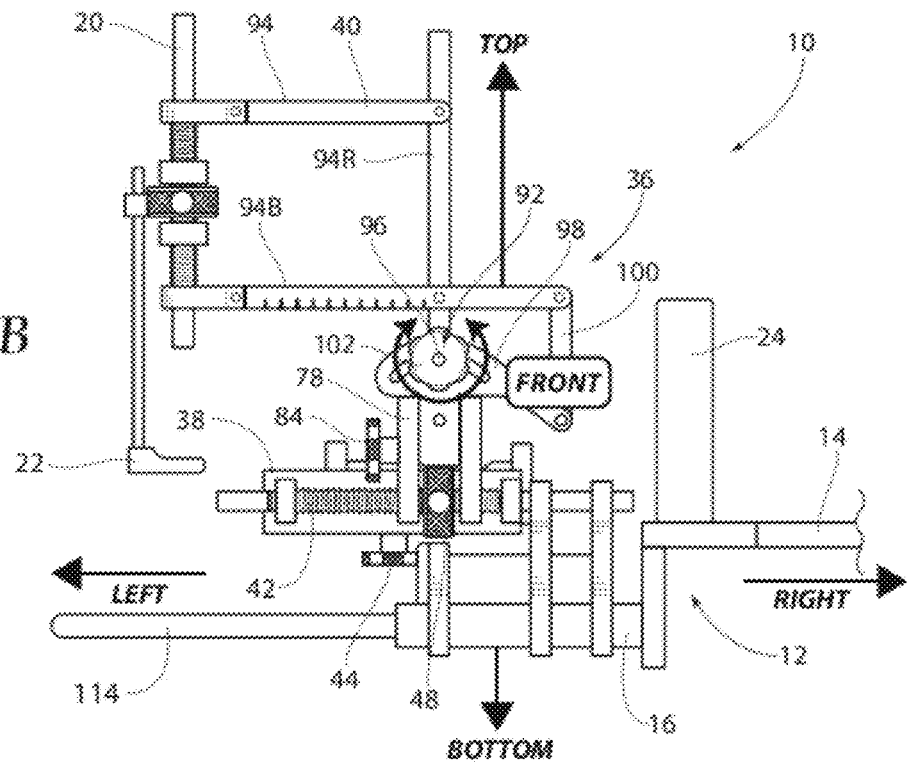

The third pivot point connection system 92 between the horizontal traction carriage 38 and the radius/ulna carriage, as best shown in FIGS. 17A, 17B, 17E, and 17F), is further shaded for identification in FIG. 23A, which (like its companion FIGS. 23B and 23C) also incorporates the directional points of reference established in FIG. 17A.

With reference first to FIGS. 17A and 17B, in the exemplary embodiment, the third pivot point connection system 92 comprises the scaffold structure 40 hereto described as structurally linking the radius/ulna support carriage 20 to the horizontal traction carriage 38. The scaffold structure 40 includes articulating link bars 94 that are pivotally coupled along axes that extend generally Front-to-Back on the reduction frame 12, forming an articulating parallelogram. The most Left-ward side of the parallelogram comprises the vertical traction carriage 60 of the superior traction mechanical force reduction system, to which the radius/ulna support carriage 20 is coupled. The link bar 94R forming the most Right-ward side of the parallelogram extends Bottom-ward below the parallelogram, where it is pivotally coupled by a flexion pin 96 to a flexion arm 98. The link bar 94B forming the most Bottom-ward side of the parallelogram extends Right-ward beyond the parallelogram, where it is coupled by a link 100 to a lateral extension of the flexion arm 98, which projects Right-ward from the pin 96. The flexion arm 98 is itself coupled to the horizontal traction carriage 38 by the first pivot point connection system 78.

As previously described (see FIG. 21C), due to the connection of the flexion arm 98 to the first pivot point connection system 78 (extending along a Left-to-Right axis), the radius/ulna support carriage 20 coupled to the articulated parallelogram-shaped scaffold structure 40 can be tilted Back-ward and Front-ward in a vertical plane, to achieve varus/valgus rotation reduction.

Further, due to the pivotal connection of the articulated parallelogram-shaped scaffold structure 40 to the flexion arm 98 along the Front-to-Back axis, the entire articulated parallelogram-shaped scaffold structure 40 can, from a normal, upright position (FIG. 23B), be tilted in a vertical plane about the Front-to-Back axis in a Left direction (Left-ward) (FIG. 23C) and returned back in a Right direction (Right-ward). The Left-ward tilting of the articulated parallelogram scaffold structure 40 about the Front-to-Back axis likewise tilts the radius/ulna support carriage 20 Left-ward (see FIG. 23C).

Figure 23C:
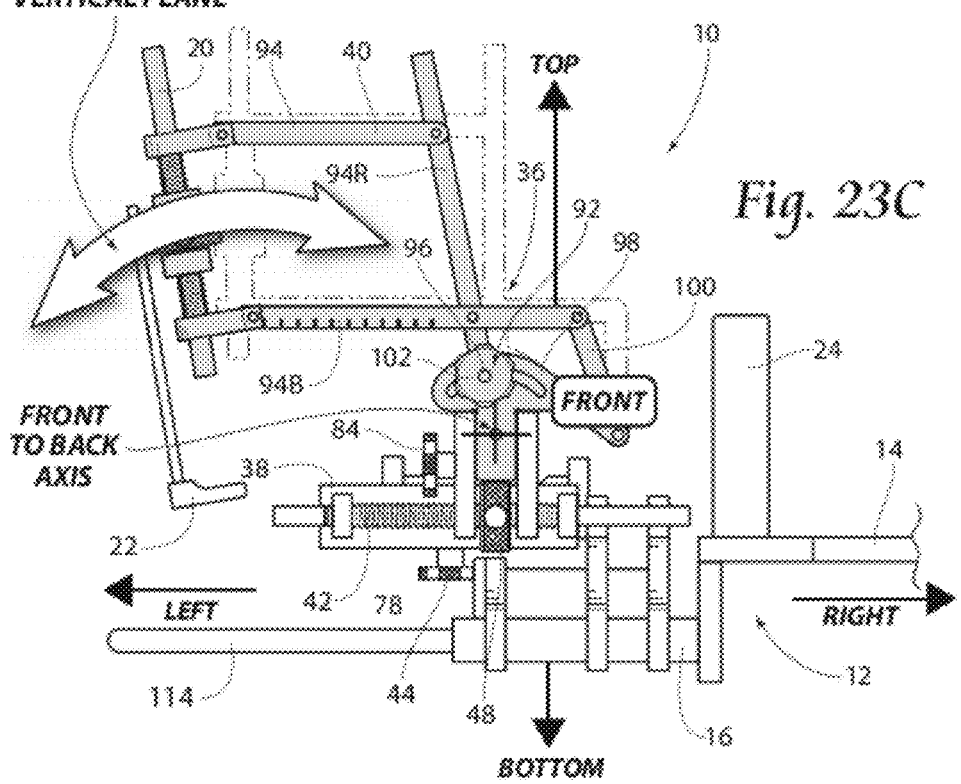

The humeral support carriage 18 is not coupled to the horizontal traction carriage 38 or the scaffold structure 40. The humeral support carriage 18 remains stationary as the radius/ulna support carriage 20 tilts Left-ward in a vertical plane about the Front-to-Back axis. As a result, the radius/ulna support carriage 20 tilts in the vertical plane Left-ward relative to the stationary humeral support carriage 18 (as FIG. 23C shows).

The flexion/extension rotation mechanical force reduction assembly 36 mechanically achieves flexion/extension rotation about the anatomic z-axis by tilting the radius/ulna support carriage 20 in an arcuate path in a vertical plane Left-ward about the Front-to-Back axis relative to the stationary humeral support carriage 18. As the radius/ulna support carriage 20 tilts Left-ward in the vertical plane relative to stationary humeral support carriage 18, a rotational force vector (torque) is applied about the anatomic z-axis to the fractured end of the distal bone fragment (held in the radius/ulna support carriage 20). The flexion/extension rotation force, mechanically applied by the flexion/extension rotation mechanical force reduction assembly 36, pivots the fractured end of the distal bone fragment about the longitudinal axis of the proximal bone fragment, to return the proximal and distal bone fragments, which have been rotationally displaced due to the fracture (as shown in FIG. 10), back toward the native state of alignment.

b. Mechanically Locking Flexion/Extension Rotation

In the exemplary embodiment, the flexion/extension rotation mechanical force reduction assembly 36 includes a flexion/extension rotation locking mechanism 102. The flexion/extension rotation locking mechanism 102 can be best seen in FIGS. 17A, 17E, 23B, and 23C. In this implementation, the flexion/extension rotation locking mechanism 102 comprises a threaded locking pin that is advanced by rotation in one direction to achieve frictional interference with the Left-ward tilting movement about the Front-to-Back axis. Frictional interference maintains the then-present tilted, torque-applying position of the radius/ulna support carriage 20, to maintain the then-present degree of flexion/extension rotation.

The flexion/extension rotation locking mechanism 102 is retracted by rotation in an opposite direction out of frictional interference with the pivot point connection. The lack of frictional interference allows tilting movement of the radius/ulna support carriage 20 Left-ward about the Front-to-Back axis to be freely achieved by the caregiver by the application a manual Left-ward tilting force upon the radius/ulna support carriage 20. When the desired degree of flexion/extension rotation is achieved, the caregiver operates the flexion/extension rotation locking mechanism to maintain the position.

In the exemplary embodiment, the pace of flexion/extension rotation is incrementally controlled in a macro-condition. In the exemplary embodiment, there is no micro-condition of flexion/extension rotation, as reducing in this plane typically does not require micro-incremental alignment.

As will be exemplified in greater detail later, the flexion/extension rotation mechanical force reduction assembly 36 applies mechanical force reduction to achieve flexion/extension rotational alignment, which can be maintained by the flexion/extension rotation locking mechanism, while other, different mechanical reduction forces are applied by the system 10.

D. Other Exemplary Embodiments

The components and mechanisms as just described are only exemplary of one embodiment of a mechanical system 10 that can be sized and configured for achieving complete composite reduction of a bone fracture by the application of mechanical force vectors. The components and mechanisms can be constructed and mutually arranged in different ways to achieve this objective.

1. FIGS. 28A to 28D

Figure 28B:
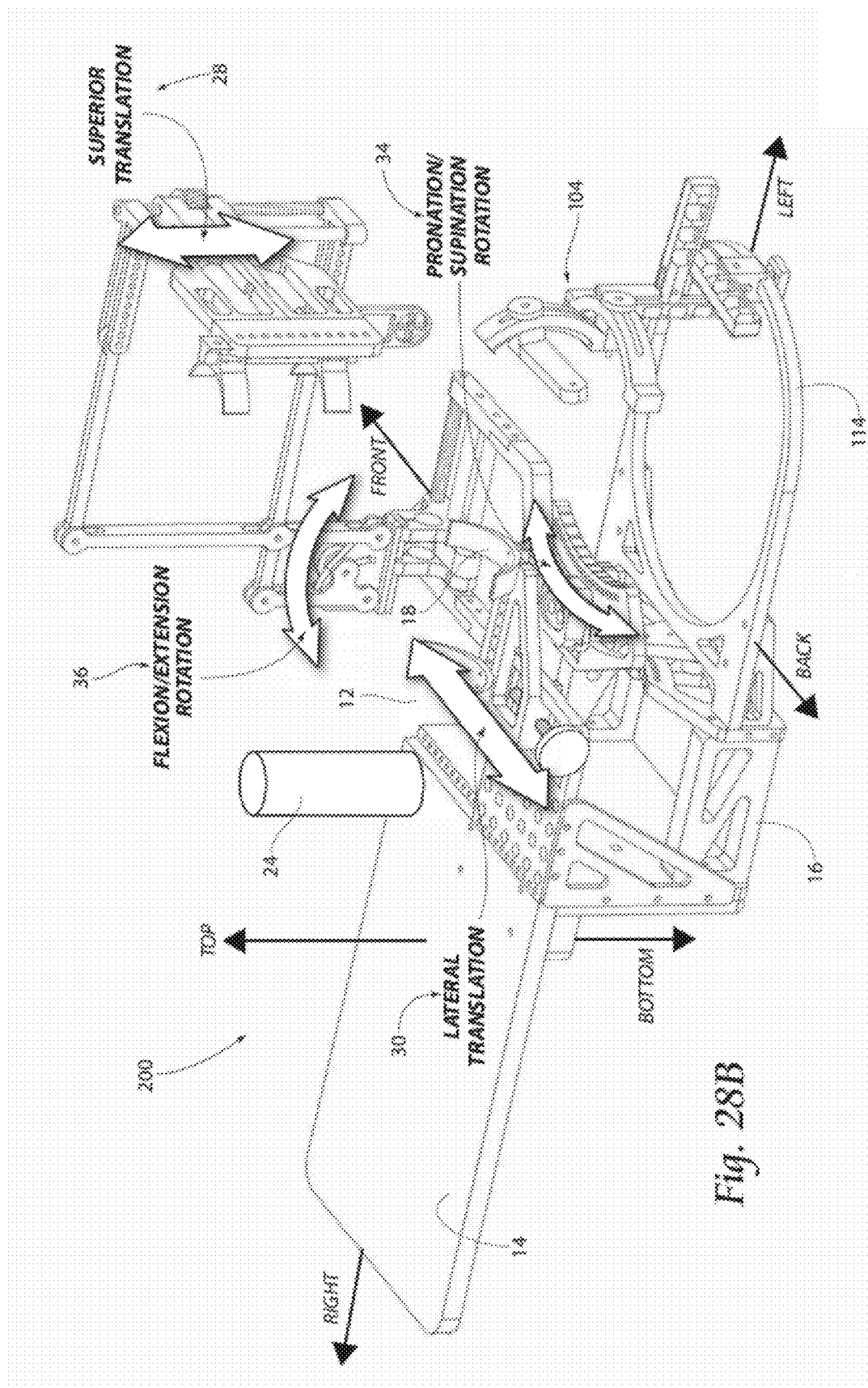
Figure 28C:
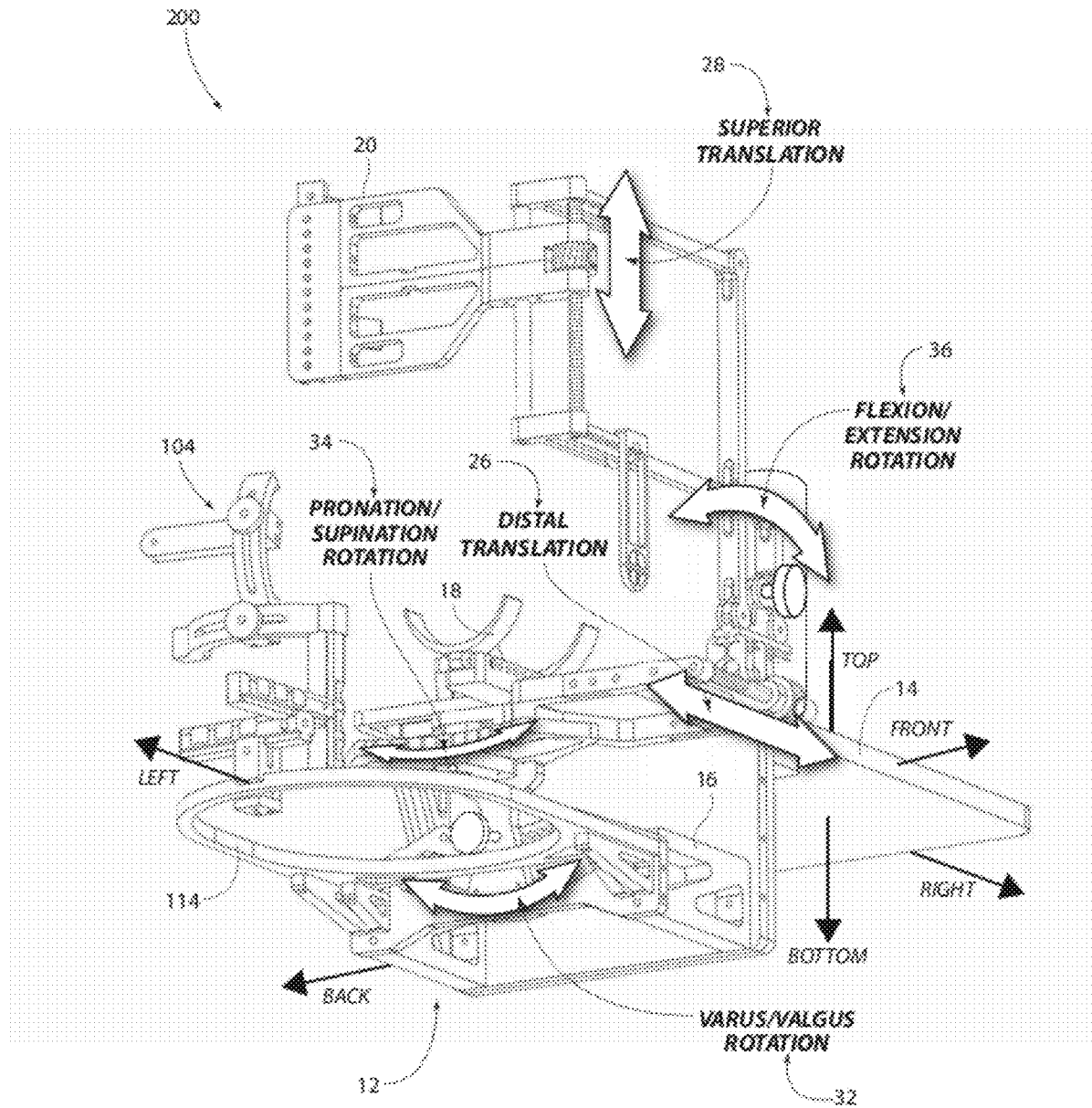

By way of example, FIGS. 28A, 28B, and 28C show, respectively, frontward, backward, and rightward looking perspective views of another exemplary system 200 sized and configured for achieving a complete, composite reduction of a bone fracture. There are many features in common with the system 10 shown in FIGS. 17A and 17B, both in terms of structure and of function. As previously described in the context of the system 10 shown in FIGS. 17A and 17B, the system 200 independently applies and maintains a plurality of disparate force reduction vectors concurrently along disparate axes. The technical features and benefits of the system 200 shown in FIGS. 28A to 28C will be described for the purpose of illustration in the context of reducing a supracondylar fracture, but the technical features that will be described are applicable to reducing bone fractures, simple or complex, of all bone types, in children or adults.

Like the system 10 shown in FIGS. 17A and 17B, the system 200 shown in FIGS. 28A, 28B, and 28C comprises a reduction frame 12. The reduction frame 12 and companion components can be fabricated from durable machined metal parts, which can be assembled in conventional fashion, e.g., by fasteners and/or welding. As in FIGS. 17A and 17B and companion figures, FIGS. 28A, 28B, and 28C have been annotated to establish baseline directional points of reference for the reduction frame 12 from a structural standpoint, which will be referred to in subsequent description; namely, Front, Back, Left, Right, Top and Bottom. The baseline directional points of reference are based upon the orientation of the reduction frame 12 as shown in FIG. 28A, and (except for the TOP and BOTTOM points of reference) are not necessarily the orientation of the reduction frame 12 when in use.

The reduction frame 12 shown in FIGS. 28A to 28C includes a similar torso support platform 14 and an appendage support platform 16. While there may be differences in appearance and certain structural details, they share common fit and function with the torso support platform 14 and an appendage support platform 16 shown in FIGS. 17A and 17B.

The torso support platform 14 shown in FIGS. 28A to 28C is sized and configured to comfortably support the upper torso of an individual to be treated, at rest in a supine (on the back) position. In FIGS. 28A and 28D, the torso support platform 14 is sized and configured for treatment of a child, but it could be sized and configured larger for treatment of an adult.

The appendage support platform 16 is likewise sized and configured to comfortably support the appendage of a child having the fracture that is to be reduced. In the illustrated embodiment, the appendage is an arm having a supracondylar fracture.

In this arrangement, the appendage support platform 16 includes (on the LEFT of the reduction frame 12) a humeral support carriage 18 and a radius/ulna support carriage 20. The humeral support carriage 18 is sized and configured to be secured to the humerus, to hold the humerus in a laterally extended position from the shoulder. The radius/ulna support carriage 20 is sized and configured to be secured to the radius/ulna to hold the radius/ulna while flexed at the elbow to point the hand in a superior direction facing the shoulder.

Likewise, a support post 24 extends in a superior direction from the main appendage support platform 16 (on the FRONT of the reduction frame 12, to engage the individual's underarm to horizontally stabilize the individual's upper torso with their arm properly oriented in the humeral support carriage 18 and the radius/ulna support carriage 20 for reduction. As before mentioned, the support post 24 can take other forms, e.g., an adjustable strap or position-adjustable pillars or columns.

In FIGS. 28A to 28C, the reduction frame 12 further includes a plurality of mechanical force reduction assemblies carried by the appendage support platform 16 in a prescribed mechanical association with the humeral support carriage 18 and the radius/ulna support carriage 20. While there may be differences in appearance and certain structural details, there are six mechanical force reduction assemblies in the system 200 shown in FIGS. 28A to 28C, which share common fit and function with the six mechanical force reduction assemblies shown in FIGS. 17A to 17F and their companion Figure Sets 18 to 23. FIGS. 28A to 28C have been annotated to reflect the inclusion of the six corresponding six mechanical force reduction assemblies, which correspond to the six mechanical force reductions identified for a supracondylar fracture. In FIGS. 28A to 28C (as in FIGS. 17A to 17F and their companion Figure Sets 18 to 23), the mechanical force reduction assemblies carried by the main appendage support platform 16 comprise (i) a distal traction mechanical force reduction assembly 26; (ii) a superior traction mechanical force reduction assembly 28; (iii) a lateral traction mechanical force reduction assembly 30; (iv) a varus/valgus rotation mechanical force reduction assembly 32; (v) a pronation/supination rotation mechanical force reduction assembly 34; and (vi) a flexion/extension rotation mechanical force reduction assembly 36. As in the system 10 described in FIGS. 17A to 17F and their companion Figure Sets 18 to 23, the six mechanical force reduction assemblies carried by the reduction frame 12 in FIGS. 28A to 28C make possible a mechanically-achieved complete composite reduction of a supracondylar fracture.

2. FIG. 29

As another example, FIG. 29 shows a backward-looking perspective view of another exemplary system 300 sized and configured for achieving a complete, composite reduction of a bone fracture. There are many features in common with the system 10 shown in FIGS. 17A and 17B, both in terms of structure and of function. As previously described in the context of the system 10 shown in FIGS. 17A and 17B, the system 300 independently applies and maintains a plurality of disparate force reduction vectors concurrently along disparate axes. The technical features and benefits of the system 300 shown in FIG. 29 will be described for the purpose of illustration in the context of reducing a supracondylar fracture, but the technical features that will be described are applicable to reducing bone fractures, simple or complex, of all bone types, in children or adults.

Like the system shown in FIGS. 17A and 17B, the system 300 shown in FIG. 29 comprises a reduction frame 12, with baseline directional points of reference from a structural standpoint; namely, Front, Back, Left, Right, Top and Bottom. The baseline directional points of reference are based upon the orientation of the reduction frame 12 as shown in FIG. 29 and (except for the TOP and BOTTOM points of reference), and are not necessarily the orientation of the reduction frame 12 when in use.

The reduction frame 12 shown in FIG. 29 includes a similar an appendage support platform 16 (in FIG. 29, there is no integral torso support platform 14, as the frame 12 is intended to rest adjacent a separate torso support table in the OR). Concerning the appendage support platform 16, while there may be differences in appearance and certain structural details, they share common fit and function with the appendage support platform 16 shown in FIGS. 17A and 17B. The appendage support platform 16 includes the humeral support carriage 18 and the radius/ulna support carriage 20. These components and their function have already been described.

In FIG. 29, the reduction frame 12 further includes a plurality of mechanical force reduction assemblies carried by the appendage support platform 16 in a prescribed mechanical association with the humeral support carriage 18 and the radius/ulna support carriage 20. While there may be differences in appearance and certain structural details, there are six mechanical force reduction assemblies in the system shown in FIG. 29, which share common fit and function with the six mechanical force reduction assemblies shown in FIGS. 17A to 17F and their companion Figure Sets 18 to 23. FIG. 29 has been annotated to reflect the inclusion of the six corresponding six mechanical force reduction assemblies, which correspond to the six mechanical force reductions identified for a supracondylar fracture. In FIG. 29 (as in FIGS. 17A to 17F and their companion Figure Sets 18 to 23), the mechanical force reduction assemblies carried by the main appendage support platform 16 comprise (i) a distal traction mechanical force reduction assembly 26; (ii) a superior traction mechanical force reduction assembly 28; (iii) a lateral traction mechanical force reduction assembly 30; (iv) a varus/valgus rotation mechanical force reduction assembly 32; (v) a pronation/supination rotation mechanical force reduction assembly 34; and (vi) a flexion/extension rotation mechanical force reduction assembly 36. As in the system described in FIGS. 17A to 17F and their companion Figure Sets 18 to 23, the six mechanical force reduction assemblies carried by the reduction frame 12 in FIG. 29 make possible a mechanically-achieved complete composite reduction of a supracondylar fracture.

3. FIG. 30

Figure 30:
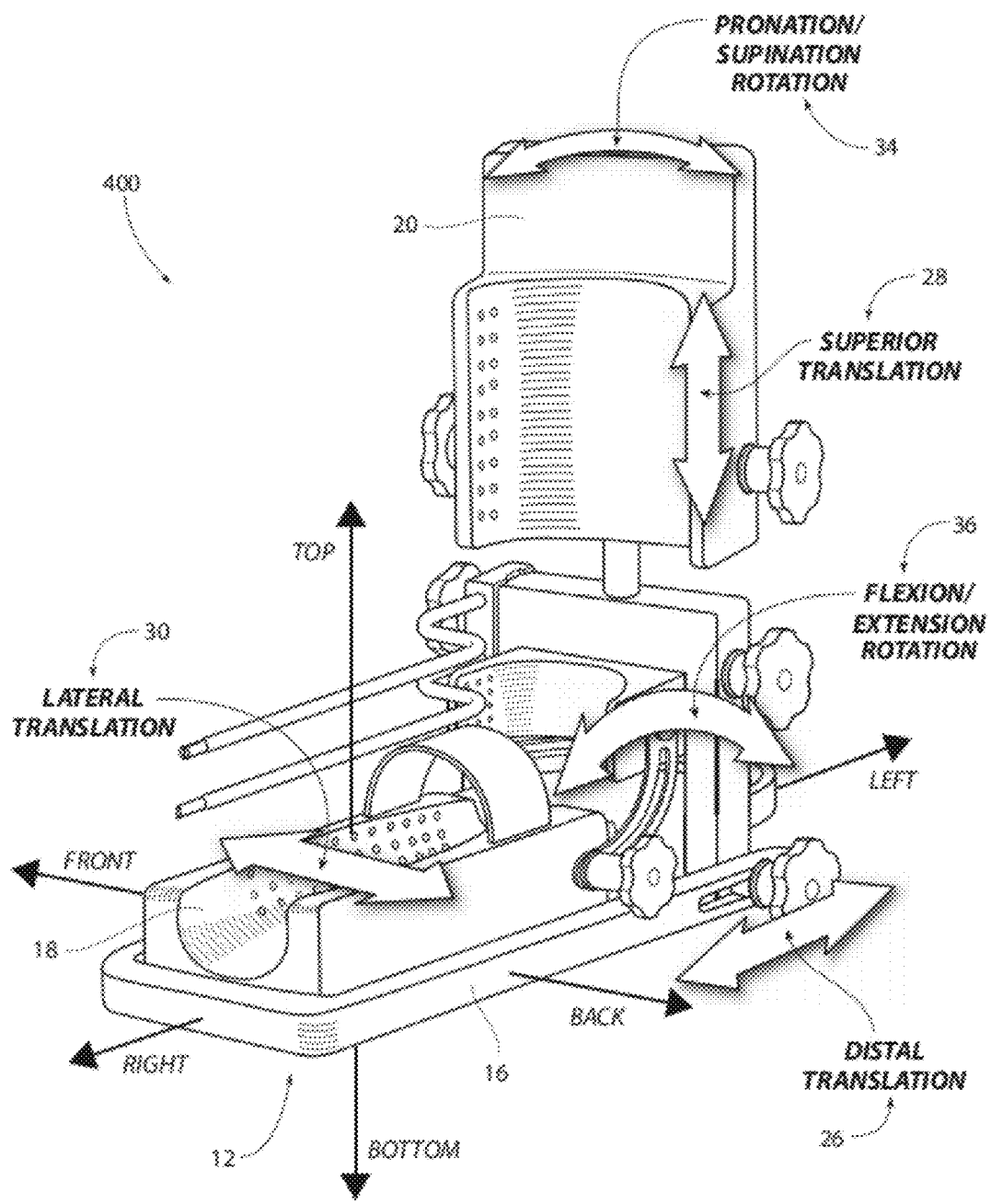
FIG. 30 is a perspective view of yet another exemplary system for achieving mechanical force reduction of a bone fracture by the application of force reduction vectors comprising distal traction, superior traction, lateral traction, pronation/suprination rotation, and flexion/extension.

As yet another example, FIG. 30 shows a backward-looking perspective view of another exemplary system 400 sized and configured for achieving a reduction of a bone fracture. There are many features in common with the system 10 shown in FIGS. 17A and 17B, both in terms of structure and of function. As previously described in the context of the system 10 shown in FIGS. 17A and 17B, the system independently applies and maintains a plurality of disparate force reduction vectors concurrently along disparate axes. The technical features and benefits of the system 400 shown in FIG. 30 will be described for the purpose of illustration in the context of reducing a supracondylar fracture, but the technical features that will be described are applicable to reducing bone fractures, simple or complex, of all bone types, in children or adults.

Like the system 10 shown in FIGS. 17A and 17B, the system 400 shown in FIG. 30 comprises a reduction frame 12, with baseline directional points of reference; namely, Front, Back, Left, Right, Top and Bottom. The baseline directional points of reference are based upon the orientation of the reduction frame 12 as shown in FIG. 30 and (except for the TOP and BOTTOM points of reference), and are not necessarily the orientation of the reduction frame 12 when in use.

The reduction frame 12 shown in FIG. 30 includes an appendage support platform 16, intended, in use, to be placed near an individual lying supine on an adjacent table (as in FIG. 29). The appendage support platform 16 includes the humeral support carriage 18 and the radius/ulna support carriage 20. These components and their function have already been described.

In FIG. 30, the reduction frame 12 also includes a plurality of mechanical force reduction assemblies carried by the appendage support platform 16 in a prescribed mechanical association with the humeral support carriage 18 and the radius/ulna support carriage 20. In FIG. 30, there are five mechanical force reduction assemblies shown, to correspond to five mechanical force reductions identified for a supracondylar fracture. In FIG. 30, the five mechanical force reduction assemblies carried by the main appendage support platform 16 comprise (i) a distal traction mechanical force reduction assembly 26; (ii) a superior traction mechanical force reduction assembly 28; (iii) a lateral traction mechanical force reduction assembly 30; (iv) a pronation/supination rotation mechanical force reduction assembly 34; and (v) a flexion/extension rotation mechanical force reduction assembly 36. The system 400 shown in FIG. 30 does not include a mechanical force reduction assembly to achieve varus/valgus rotation, to illustrate that significant benefits can be achieved by the inclusion of at least two mechanical force reduction assemblies. The at least two mechanical force reduction assemblies carried by the reduction frame 12 in FIG. 30 make possible a mechanically-achieved reduction of a supracondylar fracture having technical features lacking in the present standard of care.

V. Systems and Devices for Mechanically Fixing a Bone Fracture Following Reduction A. Overview Illustrative devices and systems for achieving a mechanical force reduction of a fracture have been described, for the purpose of illustration, in the context of reducing a supracondylar fracture. The devices and systems mechanically reduce the fracture by the application of one or more mechanical force vectors to return bone fragments separated and displaced by the fracture back toward a native state of alignment, i.e., that which existed prior to the fracture.

Next to be described are illustrative devices and systems for mechanically "fixing" the fracture following its reduction. As used herein, the terms "mechanical" and "mechanism" broadly connote the presence of one or more tools or instruments that guide the insertion of a bone fixing device. In this respect, the terms "mechanical" and "mechanism" as used herein apply not only to the use of "machines" in the traditional sense (e.g., with components such as axles, bearings, gears, linkages, springs, wheels, pulleys, motors, engines, compressors, pumps, pistons, and the like, interacting alone or in combination to generate and apply kinetic force), but also to any tool or instrument that guides the insertion of a bone fixing device using, e.g., electrical and/or electro-mechanical components, and/or pneumatic components, and/or hydraulic components, and/or electronic components, and/or mechatronic components, and/or nanotechnology components, and can also incorporate, e.g., robotics, automation, and/or computer control.

The reduction is mechanically "fixed" by providing one or more bone fixing instruments or tools 104 into the region of the reduced bone fracture. The bone fixing instruments or tools 104 provide systematic mechanical guidance for the placement of bone fixing devices such as pins or rods (see, e.g., FIG. 33), which secure the bone fragments together in the desired anatomic orientations achieved by reduction. The bone fixing devices stabilize the anatomic orientations of the reduction, thereby preventing the reduced bone fragments from moving out of reduction alignment as healing occurs.

The mechanical instruments or tools 104 and systems and methods incorporating them for fixing a fracture reduction that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained, the technical features of the instruments, tools, systems, and methods can be well exemplified and highlighted with respect to the fixing of supracondylar fractures of the elbow. For this reason, the instruments, tools, systems, and methods will be described in this context. Nevertheless, it is to be appreciated that the instruments, tools, systems, and methods that embody features of the invention are not restricted to supracondylar applications. It is to be appreciated that the disclosed instruments, devices, systems, and methods are readily applicable for use in treating all types of bone fractures, simple or complex, of any bone type, in children or adults, anywhere in the body.

Figure 34:
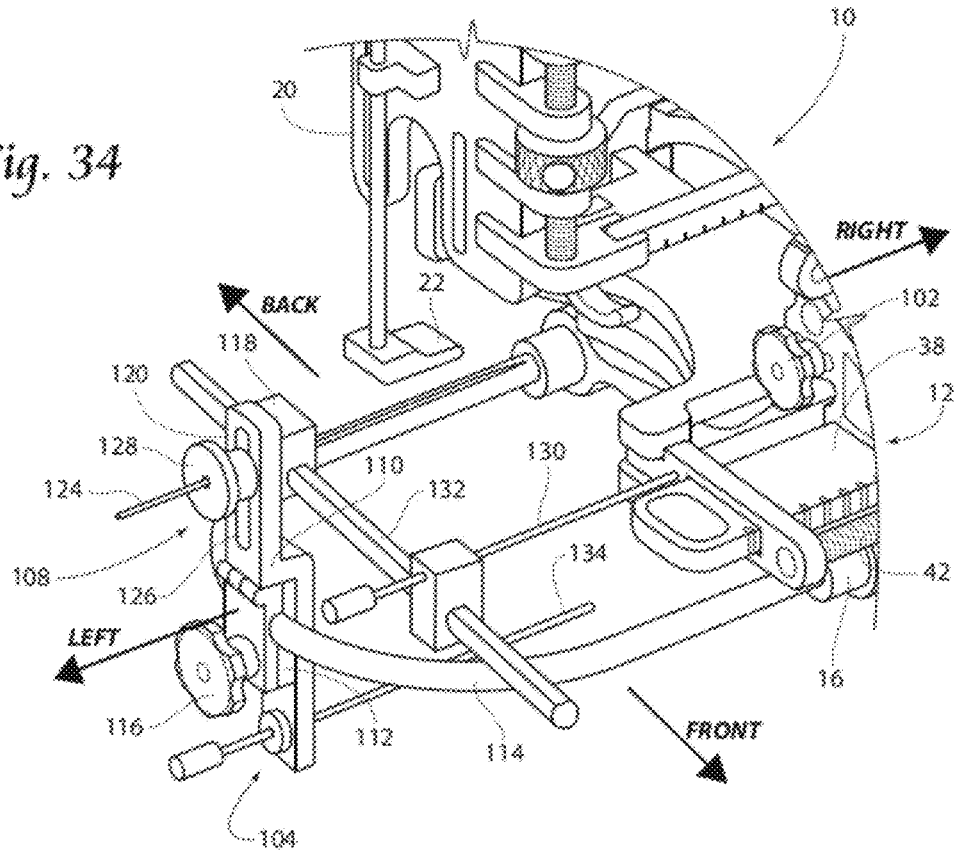
Figure 35A:
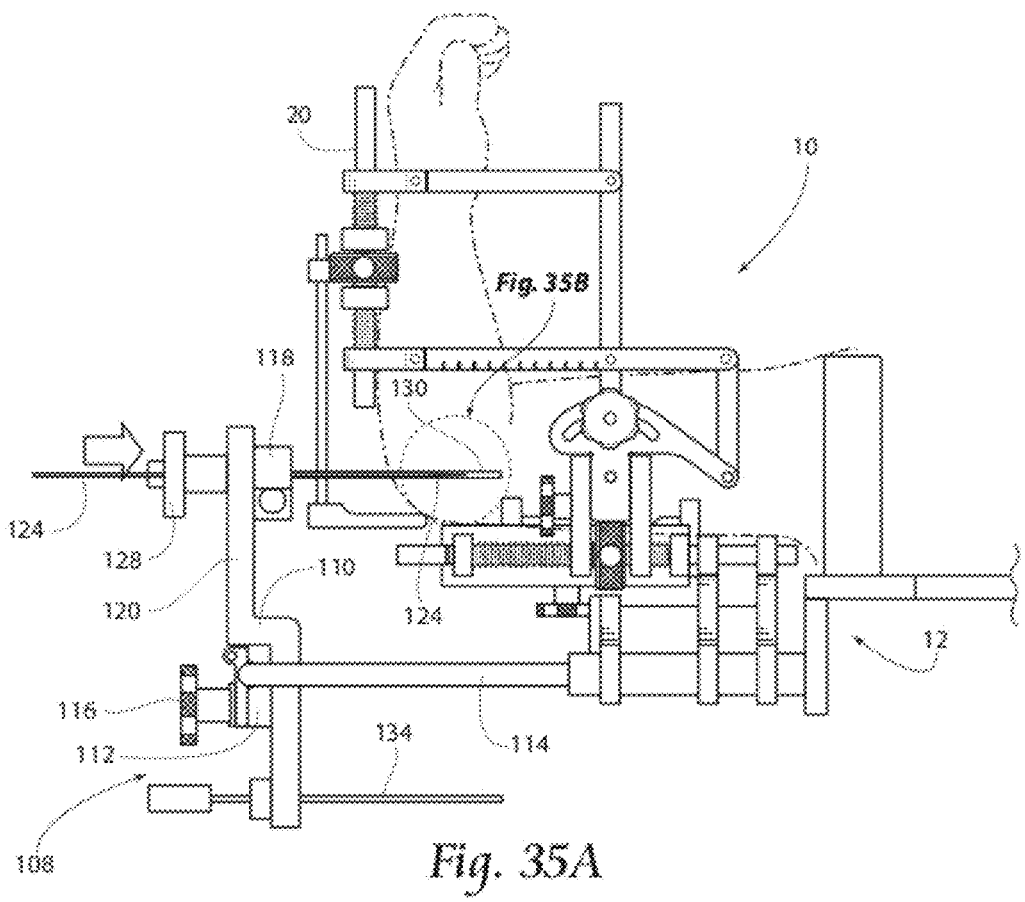
FIGS. 35A and 35B show a lateral view of the exemplary mechanism shown FIGS. 33 and 34 in use providing mechanical guidance for the placement of one or more bone fixing devices to fix a reduced bone fracture.

In the illustrative embodiments, the instruments, tools, and systems for mechanically fixing the reduced bone fracture are shown in association with the devices and systems for mechanically reducing the bone fracture in the first instance. For example, FIGS. 28A, 28B, and 28C show a bone fixing instrument or tool 104 associated with the mechanical fracture reduction system 200. FIG. 29 likewise shows a bone fixing instrument or tool 104 associated with the mechanical fracture reduction system 300. FIGS. 34 and 35A likewise shows a bone fixing instrument or tool 104 associated with the mechanical fracture reduction system 10.

The integration of devices and systems for mechanically reducing and fixing a bone fracture is desirable, but not essential. The systems and devices for mechanically reducing a bone fracture in the first instance, and then fixing the reduced bone fracture in the second instance can comprise separate, free-standing units, or, as will be shown, integrated into assemblies having complementing, dual functionality.

Figure 31A:
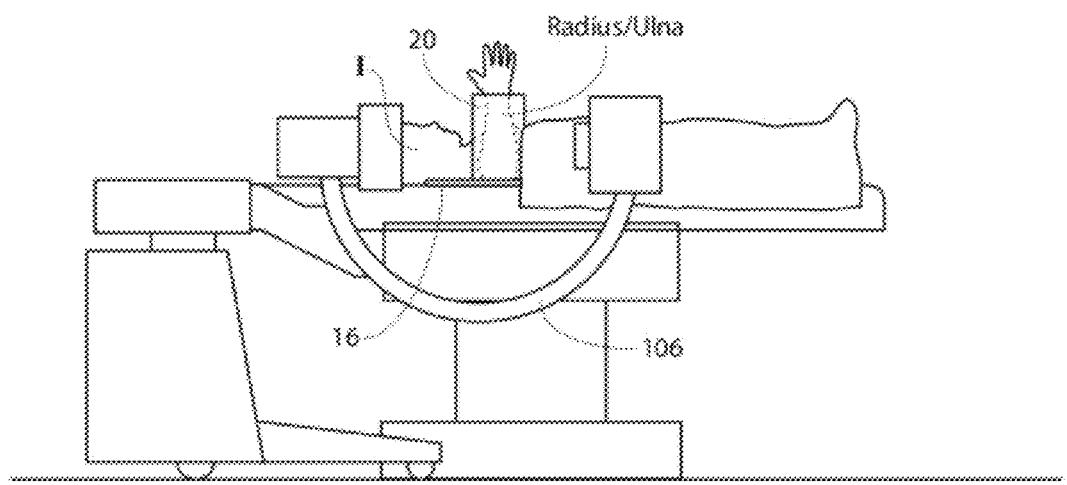
FIG. 31A is a side view of a system for achieving mechanical force reduction of a bone fracture in use on an operating table and aided by lateral radiographic imaging.

In use, both bone reduction and bone reduction fixing are desirably performed using conventional radiation imaging techniques. This is illustrated in FIGS. 31A/B and FIGS. 32A/B. FIG. 31A shows an individual I having a supracondylar fracture lying in a supine position for treatment. For treatment, the humerus of the individual is laterally extended from the shoulder and the radius/ulna is flexed at the elbow to point the hand in a superior direction facing the shoulder. The orientation of the individual's humerus and radius/ulna can be maintained, e.g., by the humeral support carriage 18 and the radius/ulna support carriage 20 of the appendage support platform 16 of a mechanical reduction system, as has been and will be described in greater detail later.

Figure 31B:
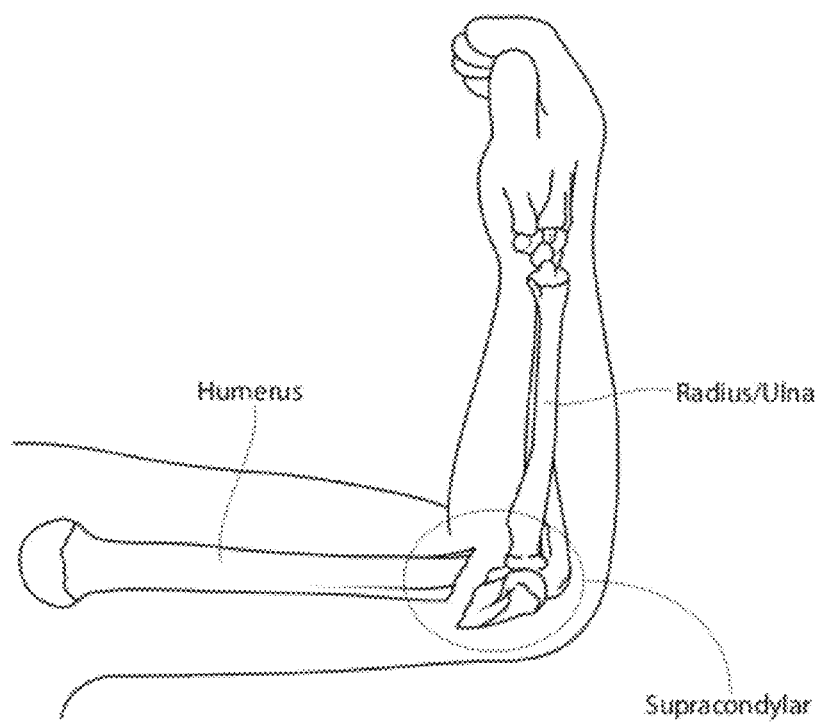
FIG. 31B is a lateral radiographic image of a supracondylar fracture that the system shown in FIG. 31A, during use, can reduce.
Figure 32A:
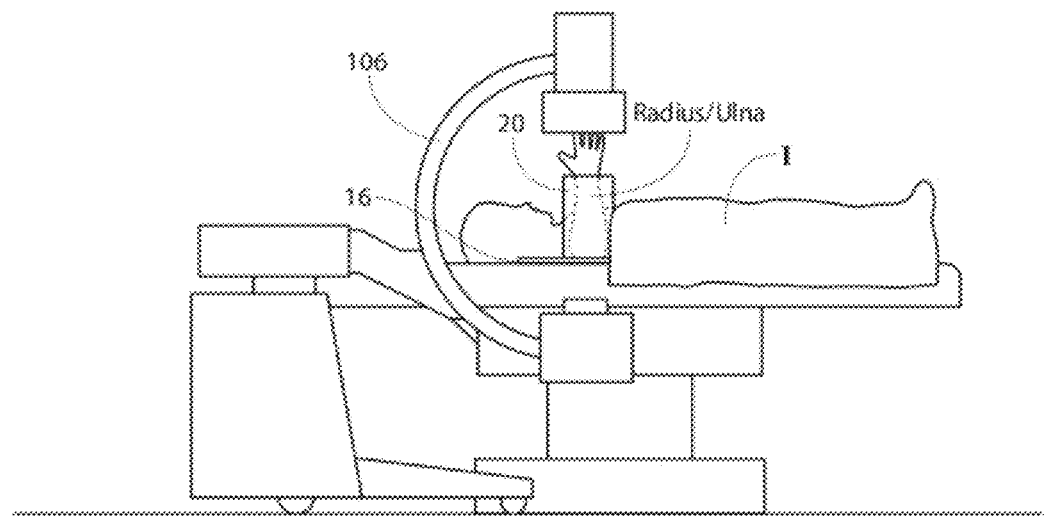
FIG. 32A is a side view of a system for achieving mechanical force reduction of a bone fracture in use on an operating table and aided by a-p radiographic imaging.
Figure 32B:
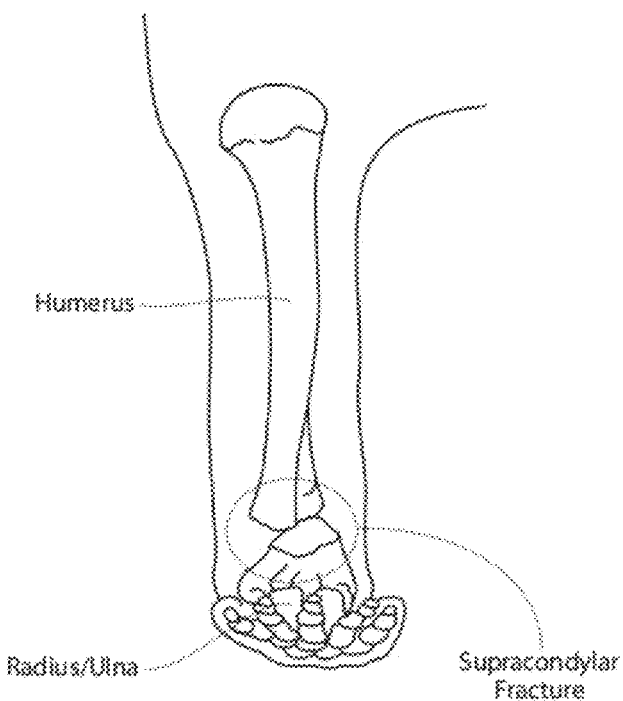
FIG. 32B is an a-p radiographic image of a supracondylar fracture that the system shown in FIGS. 31A and 32A, during use, can reduce.

Conventional radiation imaging techniques include a c-arm 106 that applies radiation through the fracture region to create a viewable radiographic image of the orientation of the bone structures. The c-arm 106 can be oriented relative to the fracture region in a horizontal plane (as shown in FIG. 31A), to provide a lateral view of the fracture region, which is shown in FIG. 31B. The c-arm 106 can also be swung into a generally vertical plane with respect to the fracture region (as shown in FIG. 32A) to provide an anterior-to-posterior (a-p) view of the fracture region, which is shown in FIG. 32B. The use of the radiographic lateral and a-p views during mechanical force reduction will be further described in greater detail later. First, there will be a description of the structural form and function of representative devices and systems for mechanically "fixing" the fracture following its reduction, which also relies upon use of the radiographic lateral and a-p views just described.

B. Exemplary Embodiment

Figure 33:
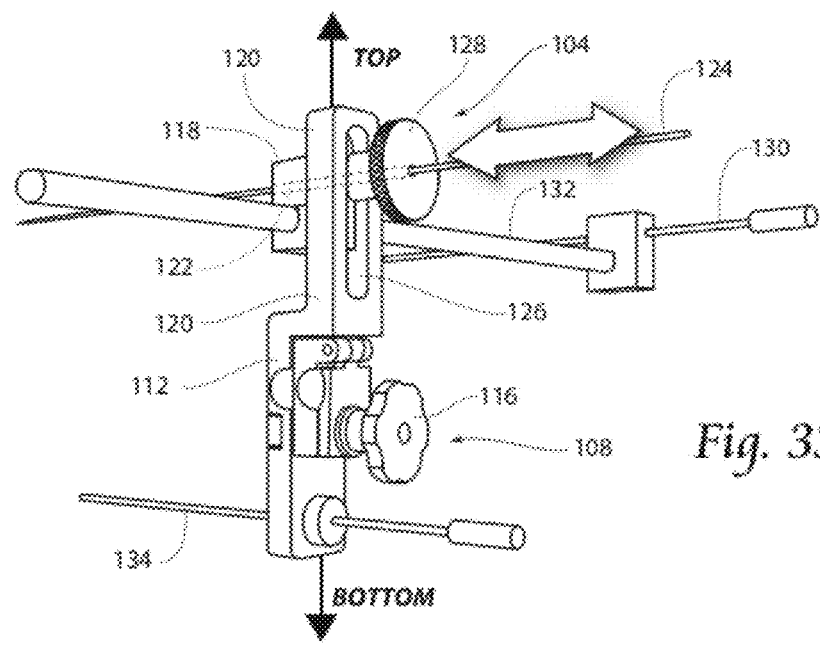
FIGS. 33 and 34 are perspective views of an exemplary mechanism for providing mechanical guidance for the placement of one or more bone fixing devices to fix a reduced bone fracture.

FIG. 33 is an exemplary embodiment of a bone fixing instrument or tool 104 comprising a system 108 for mechanically "fixing" a fracture following its reduction. The system 108 includes a shuttle body 110. The shuttle body 110 is sized and configured to be adjustably located relative to a bone region having a fracture that has been reduced. In the exemplary embodiment shown in FIG. 33, the shuttle body 110 includes a first mount 112 that is sized and configured to slide along a fixing alignment rail 114 that projects along a horizontal axis from the LEFT side of the appendage support platform 16 of the reduction frame 12 shown in FIG. 17A (see also FIG. 34). The fixing alignment rail 114 is also shown in FIGS. 17A to 17F and their companion Figure Sets 18 to 23. The presence of an integral fixing alignment rail 114 is also shown in the system 200 shown in FIGS. 28A to 28C and in the system 300 shown in FIG. 30.

In FIG. 33 (and in the other systems 200 and 300), the fixing alignment rail 114 extends within the horizontal axis in a curvilinear path from the LEFT side of the appendage support platform 16 (the directional points of reference in FIG. 33 coincide with the directional points of reference in FIGS. 17A and 17B). The fixing alignment rail 114 defines an arcuate path from FRONT to BACK of the reduction frame 12, traversing the region of the reduction frame 12 where the humeral support carriage 18 and radius/ulna support carriage 20 maintain the proximal and distal bone fragments (in alignment after reduction) bent at the elbow. The first mount 112 of the shuttle body 110 permits the shuttle body 110 to be manually positioned at an infinite number of positions with the horizontal axis along the fixing alignment rail 114.

A shuttle locking screw 116 can be tightened by rotation in one direction to establish frictional interference between the first mount 112 and fixing alignment rail 114, thereby preventing travel along the fixing alignment rail 114 and preserving the then-established position of the shuttle body 110. The shuttle locking screw 116 can be loosened by rotation in an opposite direction to remove frictional interference between the mount and the fixing alignment rail 114, thereby allowing free travel of the shuttle body 110 along the fixing alignment rail 114 for repositioning.

The shuttle body 110 carries a guide 118 within a second mount 120 vertically above the first mount 112 (i.e., vertically Top-ward of the mount). The guide 118 includes an interior channel 122 (see FIG. 33). The interior channel 122 extends along a horizontal axis, which defines a linear path along which a conventional bone fixing device 124 can be manually advanced (through the channel) by a caregiver. In the illustrated embodiment (see FIG. 33), the bone fixing device 124 comprises a thin rod (or pin) having a sharpened leading tip for penetrating skin and bone during advancement.

The bone fixing device 124 includes a radio-opaque material, so that the orientation of the bone fixation device 124 relative to the reduced bone structures can be concurrently viewed by radiation imaging.

As FIG. 33 shows, the vertical distance between the guide and the first mount 112 (and the fixing alignment rail 114 itself) can be manually adjusted by a caregiver by sliding the guide 118 within a vertically elongated (TOP to BOTTOM) slot 126 formed in the second mount 120. The vertical axis of the slot 126 extends generally perpendicular to the horizontal axis of the mount 112 and, therefore, perpendicular to the fixing alignment rail 114 itself. The slot 126 permits the guide 118 to be manually positioned above the mount 112, within the vertical confines of the slot 126, at an infinite number of positions within a vertical axis perpendicular to the fixing alignment rail 114.

A guide locking screw 128 can be tightened by rotation in one direction to establish frictional interference between the slot 126 and the guide 118, thereby preventing travel within the slot 126 and preserving the then-established vertical separation between the guide 118 and the mount 112. The guide locking screw 128 can be loosened by rotation in an opposite direction to remove frictional interference between the guide 118 and the slot 126, thereby allowing travel of the guide 118 within the slot 126 for adjusting the vertical separation between the guide 118 and the mount 112.

The guide 118 further carries a lateral guide pin 130 (see FIG. 33). The lateral guide pin 130 includes a radio-opaque material, so that the orientation of the lateral guide pin 130 can be visualized by radiographic imaging. The lateral guide pin 130 is carried in a stationary position outside the body region during use by an arm 132 that projects laterally from the guide 118. The axis of the lateral guide pin 130 is parallel to and axially aligned with (i.e., in the same horizontal plane as) the path along which the bone fixing device 124 is manually advanced by a caregiver. The arm 132 on which the lateral guide pin 130 is carried moves in tandem with the guide 118 within the slot 126, so the axial alignment of the lateral guide pin 130 and the path of advancement of the bone fixing device 124 is maintained while the vertical separation between the guide 118 and the mount 112 is adjusted.

Figure 35B:
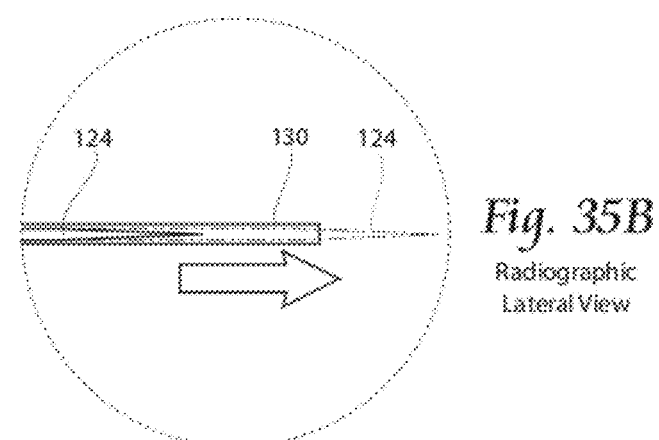

Due to this purposeful alignment, when the c-arm 106 is oriented in a horizontal plane (shown in FIG. 31B), the radiographic lateral view (see FIG. 35A) will include the image of the lateral guide pin 130. As the caregiver manually advances the bone fixing device 124 into the view through the guide 118 (see FIG. 35B), the lateral image of the bone fixing device 124 will coincide with the lateral image of the lateral guide pin 130. Adjustment of the vertical separation of the guide 118 from the first mount 112 from BOTTOM to TOP also moves the lateral guide pin 130 in tandem, to establish within the vertical plane a height for insertion of the bone fixing device 124. The height for placement of the bone fixing device 124 within the vertical plane can therefore previewed by lateral monitoring of the lateral guide pin 13, prior to actual insertion of the bone fixing device 124.

As FIGS. 33 and 34 show, the shuttle body 110 also includes an a-p guide pin 134 positioned in a stationary position vertically below the first mount 112 (i.e., vertically Bottom-ward of the first mount 112). The a-p guide pin 134 includes a radio-opaque material, so that the orientation of the a-p guide pin can be visualized by radiographic imaging. The a-p guide pin 134 extends outside the body region along a horizontal axis that is parallel to and axially aligned with (i.e., in the same vertical plane as) the axis of the path along which the bone fixing device 124 is manually advanced by a caregiver.

Figure 37:
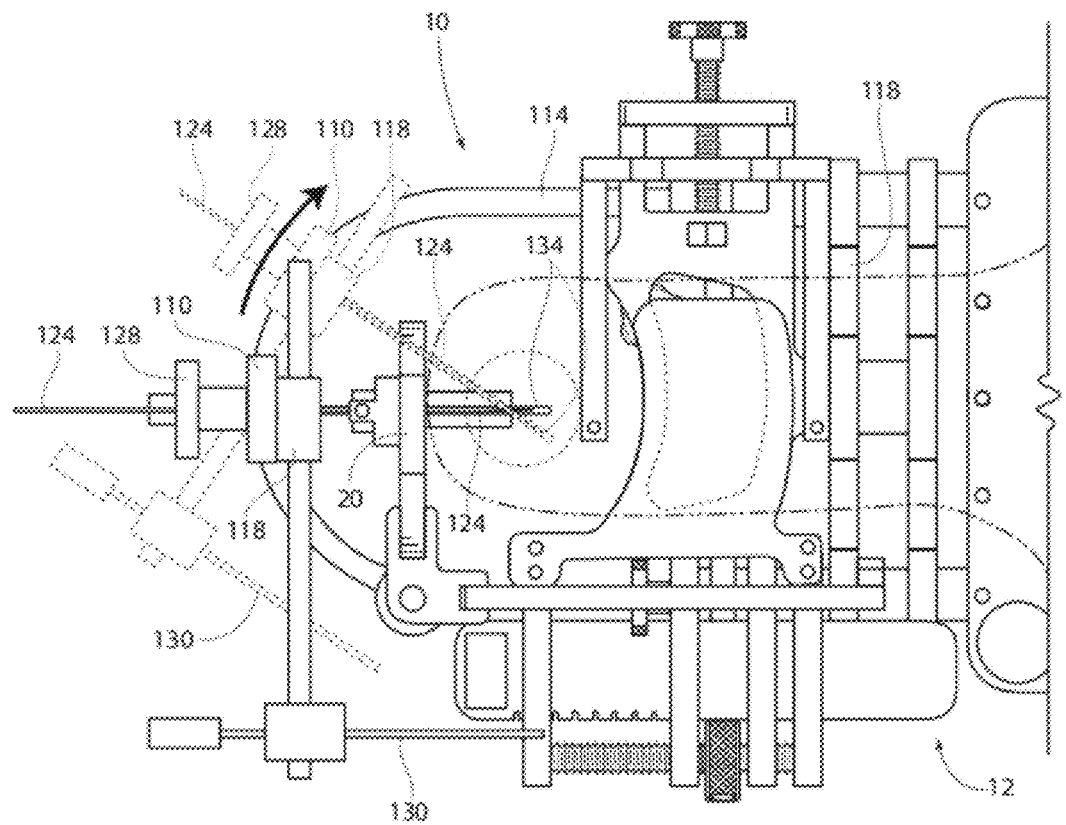
FIG. 37 further shows an a-p view of the exemplary mechanism shown FIGS. 33 and 34 in use providing mechanical guidance for the placement of one or more bone fixing devices to fix a reduced bone fracture.

Due to this purposeful alignment, when the c-arm 106 is oriented in a vertical plane (shown in FIG. 32A), the radiographic a-p view (see FIGS. 36A and 37) will include the image of the a-p guide pin 134. As the bone fixing device 124 is manually advanced by a caregiver into the view (see FIG. 36B), the a-p image of the bone fixing device 124 will coincide with the a-p image of the a-p guide pin 134. Adjustment of position of the guide 118 from TOP to BACK along the fixing alignment rail 114 (see FIG. 37) also moves the a-p guide pin 134 in tandem, to establish within the horizontal plane an angle for insertion of the bone fixing device 124. The angle of placement of the bone fixing device 124 within the horizontal plane can therefore previewed by a-p monitoring of the a-p guide pin 134, prior to actual insertion of the bone fixing device 124.

The system 108 for mechanically "fixing" a fracture as just described makes it possible to guide placement of a bone fixing device 124 in a one plane (e.g., a vertical plane), by adjusting the TOP-ward separation between the first mount 112 and the guide 118, as well as a second plane, different than the first plane (e.g., a horizontal plane), by adjusting the FRONT-ward or BACK-ward position of the shuttle body 110 along the fixing alignment rail 114. By monitoring the positions of the lateral guide pin 130 (by viewing the lateral radiographic image) and the a-p guide pin 134 (by viewing the a-p radiographic image), a caregiver is able to independently locate and maintain orientation of one or more bone fixing devices 124 relative to a reduced fracture in two different planes (e.g., horizontal and vertical planes), before actual insertion of the bone fixing device 124 through the reduced fracture. Upon insertion of one or more bone fixing devices 124 through the reduced fracture, the presence of the bone fixing devices 124 across the reduction stabilizes the orientation of a reduced bone fracture (see FIG. 38, which is an a-p, cross sectional view of a reduced supracondylar fracture of a left arm, after insertion of two bone fixing devices 124).

Figure 38:
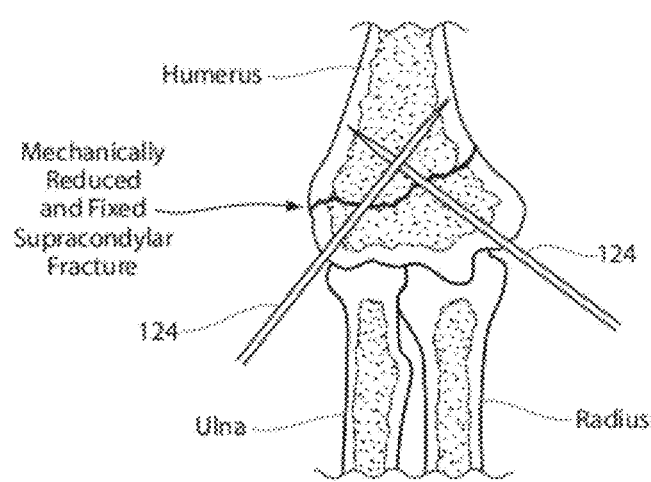
FIG. 38 shows a bone reduction after fixing.

If desired, the bone fixing devices 124 as shown in FIG. 38 can serve as pin guides for the placement of bone fixing screws across the reduction. In this arrangement, following insertion of the bone fixing devices 124 using the system 108 for mechanically "fixing" a fracture, the caregiver can pass cannulated bone fixing screws over the bone fixing devices 124 and operate a cannuated driver to screw the bone fixing screws into bone. Following this, the caregiver can withdraw the bone fixing devices 124. The presence of the screws across the reduction further stabilizes the orientation of a reduced bone fracture, particularly in adults.

C. Another Exemplary Embodiment

The tools and instruments as just described are exemplary a mechanical system that can be sized and configured for mechanically fixing a fracture following its reduction. The tools and instruments can be constructed and mutually arranged in different ways to achieve this objective.

Figure 39:
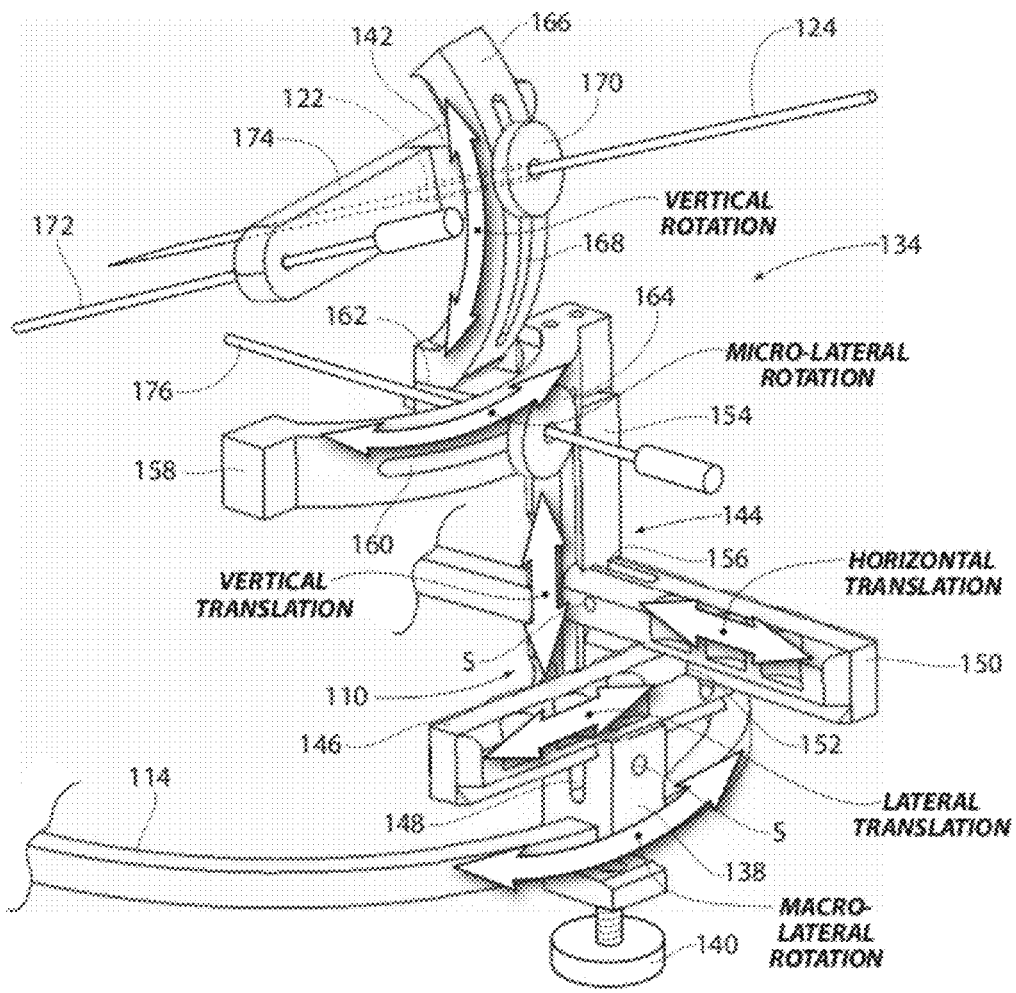
FIGS. 39 and 40 are perspective views of another exemplary mechanism for providing mechanical guidance for the placement of one or more bone fixing devices to fix a reduced bone fracture.

By way of example, FIG. 39 is another exemplary embodiment of bone fixing instrument or tool 104 comprising a system 136 for mechanically fixing a fracture following its reduction. There are many features in common with the system 108 shown in FIGS. 33 to 37, both in terms of structure and of function. As previously described in the context of the system 108 shown in FIGS. 33 to 37, the system 136 establishes and maintains, by mechanical means, a desired path for advancement of a bone fixing device 124—independently in different planes—prior to advancement of the bone fixing device 124 into a reduced bone fracture. The technical features and benefits of the system 136 shown in FIGS. 39 to 42 will be described for the purpose of illustration in the context of reducing a supracondylar fracture, but the technical features that will be described are applicable to reducing bone fractures, simple or complex, of all bone types, in children or adults.

Like the system 108 shown in FIGS. 33 to 37, the system 136 shown in FIGS. 39 to 42 includes a shuttle body 110. The shuttle body 110 is sized and configured to be adjustably located relative to a bone region having a fracture that has been reduced. In the exemplary embodiment shown in FIGS. 39 and 40, the shuttle body 110 includes a first mount 138 that is sized and configured to slide along a fixing alignment rail 114 that projects in a horizontal axis from the LEFT side of the appendage support platform 16 of the exemplary embodiment of the reduction frame 12 shown in FIGS. 28A to 28C (which are also incorporated into FIG. 40). The fixing alignment rail 114 extends in a curvilinear path from the LEFT side of the appendage support platform 16 (the directional points of reference in FIG. 40 coincide with the directional points of reference in FIG. 28A). The fixing alignment rail 114 defines an arcuate path from FRONT to BACK of the reduction frame 12, traversing the region of the reduction frame 12 where the humeral support carriage 18 and radius/ulna support carriage 20 maintain the proximal and distal bone fragments (in alignment after reduction) bent at the elbow. The first mount 138 of the shuttle body 110 permits the shuttle body 110 to be manually positioned at an infinite number of positions within a horizontal axis along the fixing alignment rail 114.

A shuttle locking screw 140 can be tightened by rotation in one direction to establish frictional interference between the first mount 138 and fixing alignment rail 114, thereby preventing travel along the fixing alignment rail 114 and preserving the then-established position of the shuttle body 110. The shuttle locking screw 140 can be loosened by rotation in an opposite direction to remove frictional interference between the mount and the fixing alignment rail 114, thereby allowing free travel of the shuttle body 110 along the fixing alignment rail 114 for repositioning.

The shuttle body 110 carries a guide 142 positioned vertically above the first mount 138 (i.e., vertically Top-ward of the first mount 138). Like the guide 118 shown in FIGS. 33 and 34, the guide 142 shown in FIGS. 39 and 40 includes an interior channel 122 (see FIG. 40). The interior channel 122 extends along a horizontal axis, which defines a linear path along which a conventional bone fixing device 124 can be manually advanced by a caregiver. In the illustrated embodiment (see FIGS. 39 and 40), and as before described, the bone fixing device 124 comprises a thin rod (or pin) having a sharpened leading tip for penetrating skin and bone during advancement.

Also as before described, the bone fixing device 124 includes a radio-opaque material, so that the orientation of the bone fixation device relative to the reduced bone structures can be concurrently viewed by radiation imaging.

Figure 40:
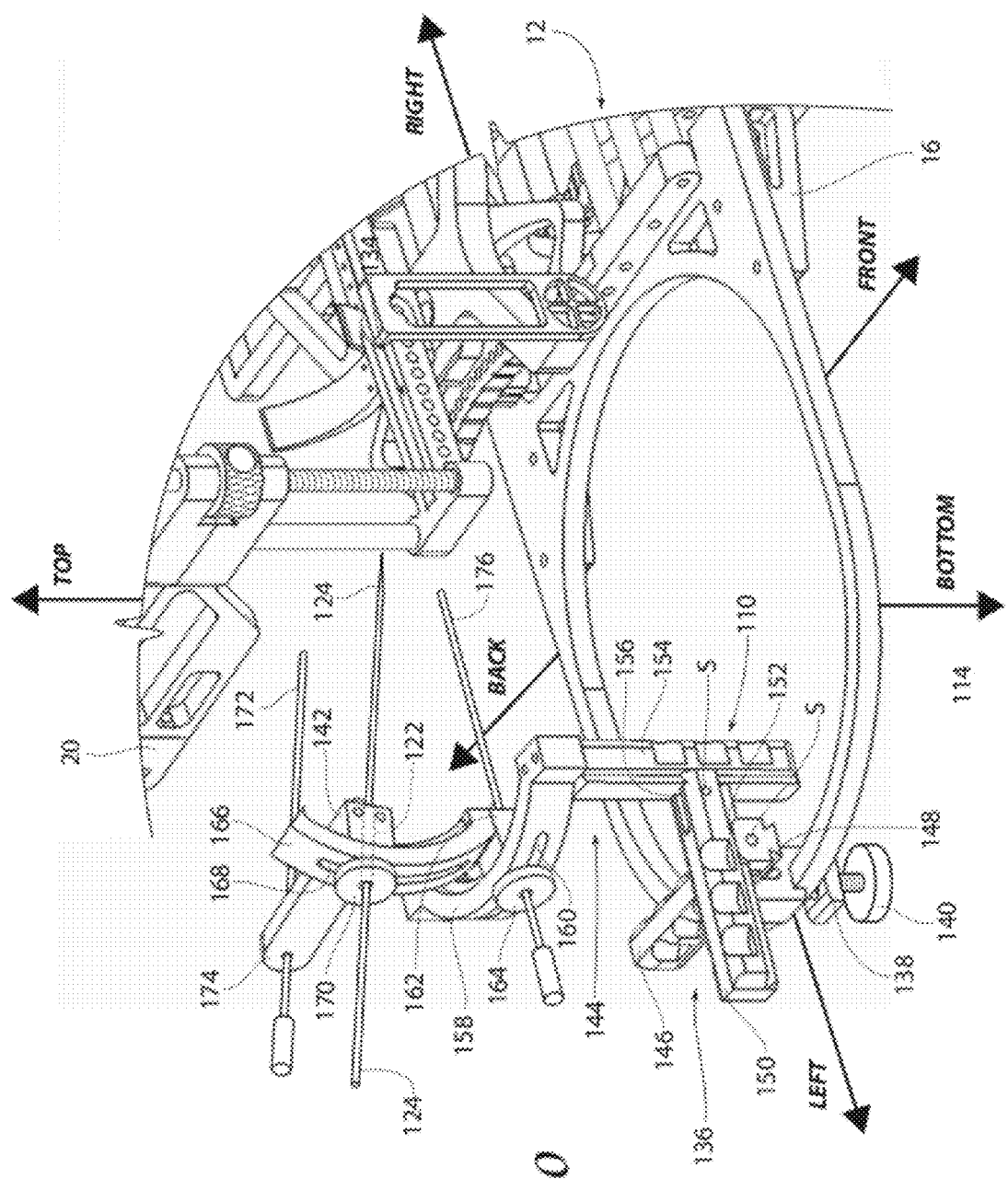
Figure 41:
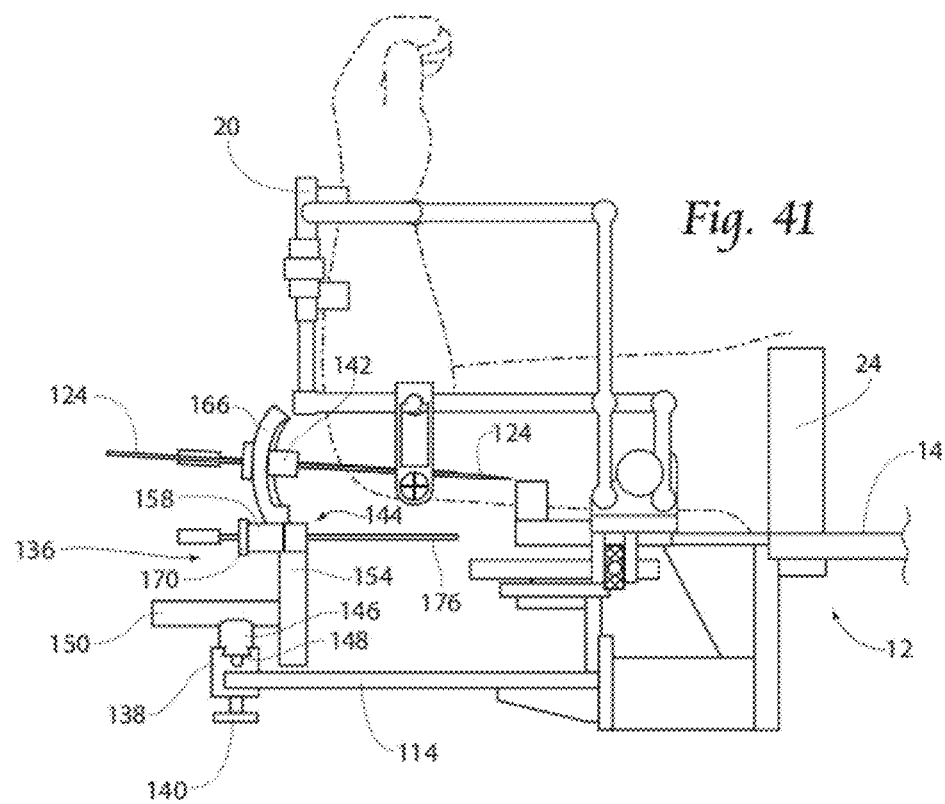
FIG. 41 is a lateral view of the exemplary mechanism shown FIGS. 39 and 40 in use providing mechanical guidance for the placement of one or more bone fixing devices to fix a reduced bone fracture.
Figure 42:
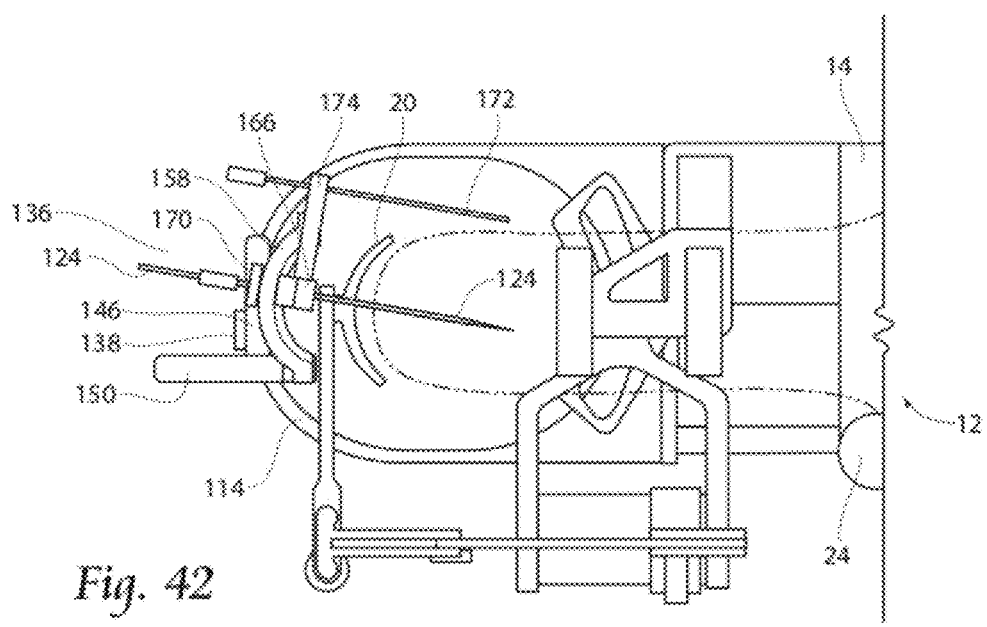
FIG. 42 is an a-p view of the exemplary mechanism shown FIGS. 39 and 40 in use providing mechanical guidance for the placement of one or more bone fixing devices to fix a reduced bone fracture.

In the exemplary embodiment shown in FIGS. 39 and 40, the mount 138 is coupled to the guide 142 by a stacked array of additional mounts comprising a linkage system 144, which allows independent orientation of the guide relative to the reduced fracture in six independent tracks. The linkage system 144 makes possible the independent orientation of the guide 142 in different planes, including a horizontal plane, a vertical plane, and one or more planes that intersect a horizontal or vertical plane at an angle (which can also be called an "angular plane"). Within each plane, the linkage system allows the caregiver to hold stationary a desired orientation in one plane, and to proceed with orientation in another plane without altering any preceding orientation.

The linkage system 144 comprises a first link bar 146 or mount that is coupled to the first mount 138 within a first channel 148 that extends parallel to the fixing alignment rail 114 in a Front-ward and Back-ward direction in the orientation shown in FIG. 40. The first channel 148 guides linear movement (i.e., translation) of the first link bar 146 relative to the mount in a Front-ward and Back-ward direction within a horizontal plane. The linkage system transmits this track of linear movement to the guide. With respect to the anatomic x-, y-, and z-axis coordinates previously discussed for the native anatomic structures in the supracondylar region held in a reduced position by the humeral support carriage 18 and radius/ulna support carriage 20 (see, e.g., FIG. 11A), the translation Front-ward to Back-ward corresponds with translation of the guide along the anatomic z-axis. The first channel 148 permits the first link bar 146 to be manually positioned at an infinite number of positions along the first channel 148. Frictional engagement between the first channel 148 and first link bar 146 can be established (e.g., by a set screw S) that holds stationary the then-established position of the first link bar 146 within the first channel 148. Release of the frictional engagement allows repositioning by the further application of a translational force by the caregiver.

The linkage system 144 further comprises a second link bar 150 or mount that is coupled to the first mount 138 within a second channel 152 in the first link bar 146 that extends perpendicular to the first channel 148 in a Left-ward and Right-ward direction in the orientation shown in FIG. 40. The second channel 152 guides linear movement (i.e., translation) of the second link bar 150 relative to the mount in a Left-ward and Right-ward direction within a horizontal plane. The linkage system 144 transmits this track of linear movement to the guide 142. With respect to the anatomic x-, y-, and z-axis coordinates previously discussed for the native anatomic structures in the supracondylar region held in a reduced position by the humeral support carriage 18 and radius/ulna support carriage 20 (see, e.g., FIG. 11A), the translation Left-ward to Right-ward corresponds with translation of the guide 142 along the anatomic x-axis. The second channel 152 permits the second link bar 150 to be manually positioned at an infinite number of positions along the second channel 152. Frictional engagement between the second channel 152 and second link bar 150 can be established (e.g., by a set screw S)

that holds stationary the then-established position of the second link bar 150 within the second channel 152. Release of the frictional engagement allows repositioning by the further application of a translational force by the caregiver.

The linkage system 144 further comprises a third link bar 154 or mount that is coupled to the first mount 138 within a third channel 156 in the second link bar 150 that extends perpendicular to the second channel 152 in a Top-ward and Bottom-ward direction in the orientation shown in FIG. 40. The third channel 156 guides linear movement (i.e., translation) of the third link bar 154 relative to the mount in a Top-ward and Bottom-ward direction with a vertical plane. The linkage system transmits this track of linear movement to the guide 142. With respect to the anatomic x-, y-, and z-axis coordinates previously discussed for the native anatomic structures in the supracondylar region held in a reduced position by the humeral support carriage 18 and radius/ulna support carriage 20 (see, e.g., FIG. 11A), the translation Top-ward to Bottom-ward corresponds with translation of the guide along the anatomic y-axis. The third channel 156 permits the third link bar 154 to be manually positioned at an infinite number of positions along the third channel 156. Frictional engagement between the third channel 156 and third link bar 154 can be established (e.g., by a set screw S) that holds stationary the then-established position of the third link bar 154 within the third channel 156. Release of the frictional engagement allows repositioning by the further application of a translational force by the caregiver.

The linkage system 144 further comprises a fourth link bar 158 or mount, which is rigidly coupled to the Top of the third link bar 154. The fourth link bar 158 is perpendicularly buttressed from the Top of the third link bar 154 in a Front-ward and Back-ward orientation, in the orientation shown in FIG. 40. The fourth link bar 158 is curvilinear, having a curvature from Front to Back, in the orientation shown in FIG. 40, which generally coincides with the curvature of the fixing alignment rail 114. The curvilinear axis of the fourth link bar 158 also extends parallel to the linear axis of the first link bar 146. The fourth link bar 158 includes an elongated horizontal slot 160 on its Left-ward side, which extends in a curvilinear Front-ward and Back-ward direction in the orientation shown in FIG. 40. A shuttle 162 rides in the slot 160 in a curvilinear Front-ward and Back-ward direction in the orientation shown in FIG. 40. The slot 160 guides curvilinear movement (i.e., rotational) of the shuttle 162 relative to the mount in a Front-ward and Back-ward trajectory within a horizontal plane. The linkage system 144 transmits this track of rotational movement to the guide 142. With respect to the anatomic x-, y-, and z-axis coordinates previously discussed for the native anatomic structures in the supracondylar region held in a reduced position by the humeral support carriage 18 and radius/ulna support carriage 20 (see, e.g., FIG. 11A), the rotational movement of the shuttle 162 in its Front-ward and Back-ward trajectory corresponds with a trajectory along the anatomic y-axis. The slot 160 permits the shuttle 162 to be manually positioned, within the horizontal confines of the slot 160, at an infinite number of positions along this trajectory along the z-axis. A shuttle locking screw 164 can be tightened by rotation in one direction to establish frictional interference between the slot 160 and the shuttle 162, thereby preventing travel along the slot 160 and preserving the then-established position of the shuttle 162. The shuttle locking screw 164 can be loosened by rotation in an opposite direction to remove frictional interference between the slot 160 and the shuttle 162, thereby allowing free travel of the shuttle 162 along the z-axis trajectory for repositioning the guide 142.

The linkage system 144 further comprises a fifth link bar 166 or mount, which is rigidly coupled to the Top of the shuttle 162. The fourth link bar 158 is perpendicularly buttressed from the Top of the shuttle in a Top-ward orientation, in the orientation shown in FIG. 40. The fifth link bar 166 is curvilinear, having a curvature from Bottom to Top which generally matches the curvature of the fourth link bar 158 from Front to Back. The fifth link bar 166 includes an elongated vertical slot 168 on its Left-ward side, which extends in a curvilinear Top-ward direction in the orientation shown in FIG. 40. The guide 142 rides in the slot 168 in a curvilinear Top-ward direction in the orientation shown in FIG. 40. The slot 168 guides curvilinear movement (i.e., rotational) of the guide 142 relative to the mount 138 in a Top-ward trajectory within a vertical plane. The Top-ward trajectory orients the interior channel 122 of the guide 142 along planes that intersect a horizontal or vertical plane at an angle (i.e., angular planes). The Top-ward trajectory (beginning that the Bottom of the slot 168 and moving to the Top of the slot 168) will orient the interior channel 122 of the guide 142 along angular planes that direct the bone fixing device 124 Top-ward, then horizontal, and then Bottom-ward. With respect to the anatomic x-, y-, and z-axis coordinates previously discussed for the native anatomic structures in the supracondylar region held in a reduced position by the humeral support carriage 18 and radius/ulna support carriage 20 (see, e.g., FIG. 11A), the rotational movement of the guide 142 in its Top-ward trajectory corresponds with a trajectory along the anatomic z-axis. The slot 168 permits the guide 142 to be manually positioned, within the vertical confines of the slot 168, at an infinite number of positions along this trajectory along the y-axis. A shuttle locking screw 170 can be tightened by rotation in one direction to establish frictional interference between the slot 168 and the guide 142, thereby preventing travel along the slot 168 and preserving the then-established position of the guide 142. The shuttle locking screw 170 can be loosened by rotation in an opposite direction to remove frictional interference between the slot 168 and the guide 142, thereby allowing free travel of the guide 142 along the y-axis trajectory for repositioning the guide 142.

As FIG. 39 shows, the vertical distance (Top-ward and Bottom-ward) between the guide 142 and the mount 138 (and the fixing alignment rail 114 itself) can be manually adjusted in both vertical translational and vertical rotational tracks. By moving the third link bar 154 Top-ward and Bottom-Ward, vertical translation along the anatomic y-axis can be achieved and maintained. By moving the guide 142 along the slot 168 within the fifth link bar 166 in a Top-ward direction, a vertical rotation (trajectory) along the anatomic z-axis can be achieved and maintained.

As FIG. 39 also shows, the horizontal distance (Left-ward and Right-ward) between the guide 142 and the mount 138 (and the fixing alignment rail 114 itself) can be manually adjusted in a horizontal translational track. By moving the second link bar 150 Left-ward and Right-Ward, horizontal translation along the anatomic x-axis can be achieved and maintained.

As FIG. 39 also shows, the horizontal offset (lateral) distance (Front-ward and Back-ward) between the guide 142 and the mount 138 (and the fixing alignment rail 114 itself) can be manually adjusted in both lateral translational and lateral rotational tracks. By moving the first link bar 146 Front-ward and Back-ward, lateral translation along the anatomic z-axis can be achieved and maintained. By moving the mount 138 along the fixing alignment rail 114, a macro-degree of lateral rotation (trajectory) along the anatomic y-axis can be achieved and maintained. By moving the shuttle 162 along the slot 160 within the fourth link bar 158, a micro-degree of horizontal rotation (trajectory), finer than the macro-degree, along the anatomic y-axis can also be achieved and maintained.

The guide 142 further carries a lateral guide pin 172 (see FIGS. 39 and 40). The lateral guide pin 172 includes a radio-opaque material, so that the orientation of the lateral guide pin 172 can be visualized by radiographic imaging. The lateral guide pin 172 is carried in a stationary position outside the body region by an arm 174 that projects laterally from the guide 142. The axis of the lateral guide pin 172 is parallel to and axially aligned with (i.e., in the same horizontal plane as) the path along which the bone fixing device 124 is manually advanced by a caregiver. The arm 174 on which the lateral guide pin 172 is carried moves in tandem with the guide 142 within the slot 168, so the axial alignment of the lateral guide pin 172 and the path of advancement of the bone fixing device 124 is maintained while the vertical separation between the guide 142 and the mount 138 is adjusted.

Due to this purposeful alignment, when the c-arm 106 is oriented in a horizontal plane (shown in FIG. 31B), the radiographic lateral view (see FIG. 41) will include the image of the lateral guide pin 172. As the caregiver manually advances the bone fixing device 124 into the view through the guide 142, the image of the bone fixing device 124 will coincide with the image of the lateral guide pin 172. Translational and rotational adjustment of the guide 142 establishes a desired path of placement for the bone fixing device 124, prior to actual insertion of the bone fixing device, aided by lateral radiographic monitoring of the position of lateral guide pin 172.

As FIGS. 39 and 40 also show, the shuttle 162 also accommodates an a-p guide pin 176 positioned in a stationary position vertically below the guide 142 (i.e., vertically Bottom-ward of the guide 142). In this exemplary embodiment, the a-p guide pin 176 is positioned outside the body region vertically above the mount 138 (i.e., vertically Top-ward of the mount). The a-p guide pin 176 includes a radio-opaque material, so that the orientation of the a-p guide pin 176 can be visualized by radiographic imaging. The a-p guide pin 176 extends along a horizontal axis that is parallel to and axially aligned with (i.e., in the same vertical plane as) the axis of the path along which the bone fixing device 124 is manually advanced by a caregiver.

Due to this purposeful alignment, when the c-arm 106 is oriented in a vertical plane (shown in FIG. 32A), the radiographic a-p view (see FIG. 42) will include the image of the a-p guide pin 176. As the bone fixing device 124 is manually advanced by a caregiver into the view, the image of the bone fixing device 124 will coincide with the image of the a-p guide pin 176. Translational and rotational adjustment of the guide 142 establishes a desired path of placement for the bone fixing device 124, prior to actual insertion of the bone fixing device 124, aided by a-p radiographic monitoring of the position of a-p guide pin 176.

The system 136 for mechanically "fixing" a fracture as just described makes it possible to guide placement of a bone fixing device 124 in vertical, horizontal, and angular planes. By monitoring the positions of the lateral guide pin 172 (by viewing the lateral radiographic image) and the a-p guide pin 176 (by viewing the a-p radiographic image), a caregiver is able to independently locate and maintain vertical, horizontal, and angular alignment of one or more bone fixing devices 124 relative to a reduced fracture, before actual insertion of the bone fixing device 124 through the reduced fracture. Upon insertion of one or more bone fixing devices 124 through the reduced fracture (see FIG. 38, which is an a-p view after insertion of two bone fixing devices 124), the presence of the bone fixing devices 124 across the reduction stabilizes the orientation of a reduced bone fracture.

As before described, the bone fixing devices 124 as shown in FIG. 38 can serve as pin guides for the placement of bone fixing screws across the reduction. In this arrangement, following insertion of the bone fixing devices 124 using the system 136 for mechanically "fixing" a fracture, the caregiver can pass cannulated bone fixing screws over the bone fixing devices 124 and operate a cannuated driver to screw the bone fixing screws into bone. Following this, the caregiver can withdraw the bone fixing devices 124. The presence of the screws across the reduction further stabilizes the orientation of a reduced bone fracture.

VI. The Orthotic Brace

Figure 43:
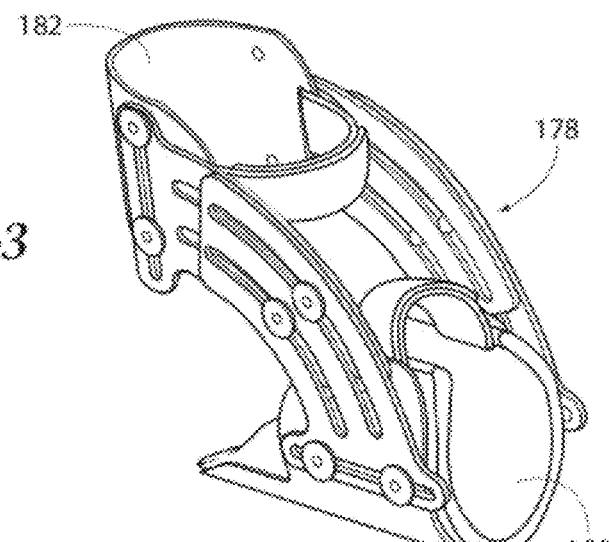
FIG. 43 is a perspective view of an orthotic that can be assembled to stabilize a fixed bone reduction for healing.

FIG. 43 shows an exemplary embodiment of an orthotic brace 178, which is sized and configured to be fully or partially assembled and fitted to a bone region having a fracture prior to, during, or after fracture reduction and fixing. The orthotic brace 178 helps to maintain and/or improve the reduction, after fixing, while healing occurs. The orthotic brace 178 performs this function by controlling, guiding, limiting and/or immobilizing the reduction after fixing; and/or restricting movement in a given direction; and/or reducing weight bearing forces; and/or otherwise maintain the orientation of the bone structures after reduction and fixing.

The orthotic brace 178 can be made from various types of materials known in the orthotics field, e.g., plastic, elastic, metal, or a combination of similar materials.

The orthotic brace 178 can be sized and configured to be part of a fracture reduction and fixing system and method, by accommodating temporary securing of the orthotic brace 178 to a force reduction frame 12, either fully or partially assembled to the region of fractured bone, to thereby reside on the reduction frame 12 while reduction is achieved and/or reside on the reduction frame 12 while mechanical reduction fixing is achieved. After reduction and fixing, the orthotic brace 178 is sized and configured worn by the individual, fully assembled to the fixed reduction, to maintain and/or improve the fixed reduction while healing occurs.

The orthotic brace 178, systems, and methods that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained in the context of previous descriptions, the technical features of the orthotic brace 178, systems, and methods can be well exemplified and highlighted with respect to the fixing of supracondylar fractures of the elbow. For this reason, the orthotic brace 178, systems, and methods will be described in this context. Nevertheless, it is to be appreciated that the orthotic brace 178, systems, and methods that embody features of the invention are not restricted to supracondylar applications. It is to be appreciated that the disclosed orthotic brace 178, systems, and methods are readily applicable for use in treating all types of bone fractures, simple or complex, of any bone type, in children or adults, anywhere in the body.

As shown in FIG. 43, the orthotic brace 178 is sized and configured for treating a supracondular fracture. In this context, the orthotic brace 178 includes a humeral brace component 180 and a radius/ulnar brace component 182. In use, see FIG. 44, the humeral brace component 180 is secured to the humerus, e.g., by straps, to hold the humerus in a laterally extended position from the shoulder. The radius/ulnar brace component 182 is secured to the radius/ulna, e.g. by straps, to hold the radius/ulna while flexed at the elbow to point the hand in a superior direction facing the shoulder.

Figure 44:
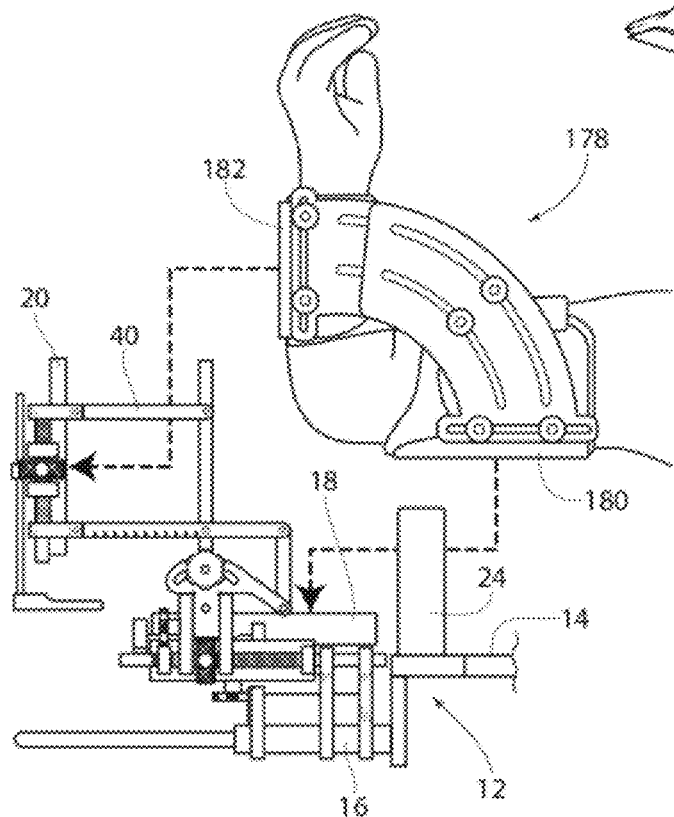
FIG. 44 is a view demonstrating the temporary placement of the orthotic shown in FIG. 43 assembled, after assembly on an arm, being fitted to a mechanical force bone reduction system.

The exemplary force reduction frames 12 previously described include a humeral support carriage 18 and a radius/ulna support carriage 20, which are likewise sized and configured to be secured to the humerus and the radius/ulna to hold the humerus and radius/ulna in the same orientation during mechanical reduction, and to maintain this orientation after reduction during mechanical fixing of the reduction. It can be appreciation that the form, fit, and function of the humeral brace component 180 and the radial/ulnar brace component 182 complement the form, fit, and function of the humeral support carriage 18 and the radius/ulna support carriage 20 of the mechanical reduction frame 12. For this reason, the orthotic brace 178 can be sized and configured to be partially or fully assembled to the individual's arm and be temporarily secured, e.g., by straps, pins, or fasteners, to the humeral support carriage 18 and the radius/ulna support carriage 20 of the reduction frame 12 prior to mechanical force reduction (as FIG. 44 shows). The orthotic brace 178 can likewise be sized and configured, while partially or fully assembled to the individual's arm, to remain secured to the humeral support carriage 18 and the radius/ulna support carriage 20 during fixing of the reduced fracture. This technical feature will be described in further detail and shown in subsequent figures. After fixing of the mechanically reduced fracture, the orthotic brace 178 is released from the reduction frame 12 and, if, required fully assembled to the individual's arm (see FIG. 45), to be worn by the individual to maintain and/or improve the reduction, after fixing, while healing occurs.

VII. Methods of Mechanically Reducing and Fixing a Bone Fracture

A. Overview

Illustrative devices and systems for achieving a mechanical force reduction and fixing of a fracture have been described, for the purpose of illustration, in the context of reducing a supracondylar fracture. Next to be described are illustrative methods for mechanically reducing and fixing a fracture using the exemplary devices and systems.

The methods that will be described are applicable to all bone fractures, simple or complex, in children or adults, and involving all bone types, including, e.g., in the arm, involving the humerus and/or forearm and/or wrist; in the leg, involving the tibia and/or fibula; and at, in, or near articulating condyles (also called a condular fracture), e.g. at, in, or near the elbow, or at, in, or near the knee. Still, as before explained in the context of previous descriptions, the technical features of the methods can be well exemplified and highlighted with respect to the fixing of supracondylar fractures of the elbow. For this reason, the methods will be described in this context. Nevertheless, it is to be appreciated that the methods that embody features of the invention are not restricted to supracondylar applications. It is to be appreciated that the disclosed methods are readily applicable for use in treating all types of bone fractures, simple or complex, of any bone type, in children or adults, anywhere in the body.

Figure 46:
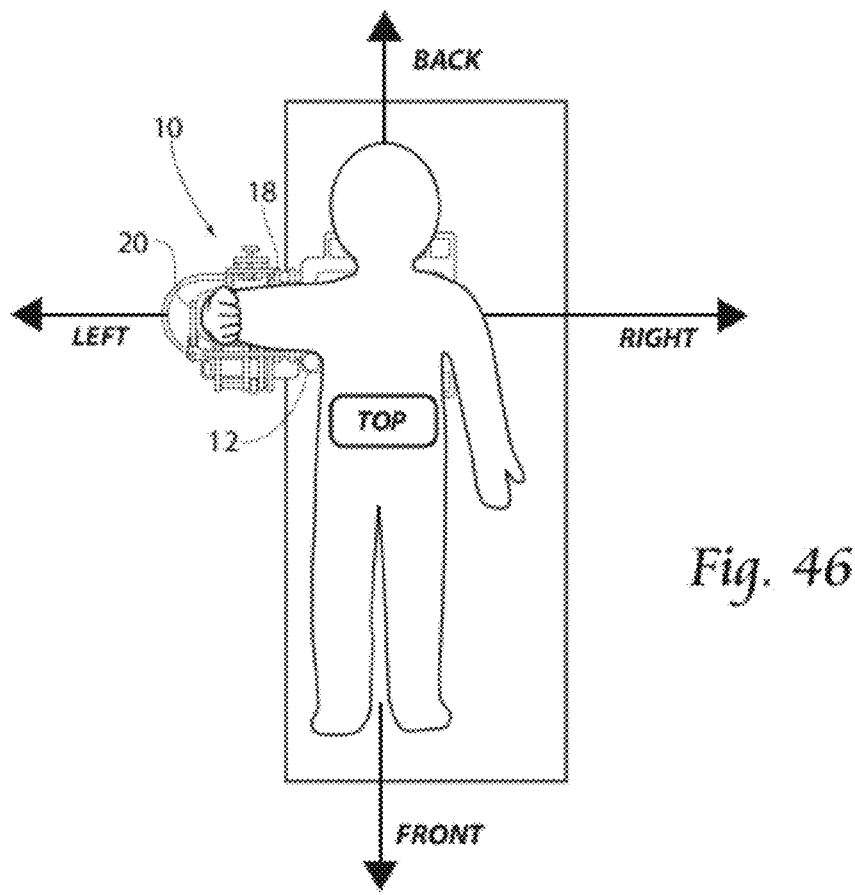

In this context, and as shown in FIG. 46, the individual having a supraconbdylar fracture to be treated in their right arm is laid in a supine position on an operating table, on which a reduction frame 12 like that shown in FIG. 17A or 33 is supported.

The directional points of reference (Front, Back, Left, Right, Top, Bottom) used in FIGS. 17A/B and FIGS. 28A/B to define the orientation of the reduction frame 12 and its structural components and mechanisms (and which annotate FIG. 46) can be readily related, if desired, to anatomic points of reference for the individual being treated.

Laying supine, the individual's anatomic anterior side faces Top-ward, and the individual's anatomic posterior side faces Bottom-ward. The individual's head (the anatomic superior or cephalad direction) faces Back-ward. The individual's feet (the anatomic inferior or caudal direction) faces Front-ward. For treatment of a right arm, the appendage support platform 16 is Left-ward, adjacent the individual's right arm side (the anatomic right lateral direction). The individual's other side (the anatomic left lateral direction) faces Right-ward. It should be appreciated that, for treatment of a left arm, the appendage support platform 16 is Right-ward, adjacent the individual's left arm side (the anatomic left lateral direction), and the individual's other side (the anatomic right lateral direction) faces Left-ward.

Thus, it can be seen how the structural directional points of reference in FIGS. 17A/B and 28A/B can be readily converted to anatomic direction points of reference relative to the individual being treated, if desired. For example, movement Left-ward corresponds (for a right arm reduction) to movement in a right lateral direction. Or, as another example, movement Top-ward corresponds (for either a right or left arm reduction) to movement in an anterior direction. Or, as another example, movement Back-ward corresponds (for either a right or left arm reduction) to movement in a superior or cephalad direction, and movement Front-ward (for either a right or left arm reduction) corresponds to movement in an inferior or caudal direction.

For the sake of consistency, subsequent description will continue to use the structural directional points of reference (Front, Back, Left, Right, Top, Bottom) used in FIGS. 17A/B and FIGS. 28A/B.

Figure 47:
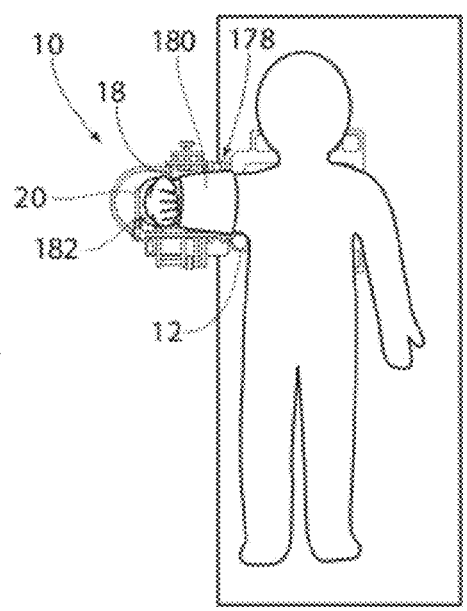

The individual's right arm is oriented with the humeral support carriage 18 and a radius/ulna support carriage 20 of the reduction frame 12. In the exemplary embodiment (see FIG. 47), the orthotic brace 178 is either fully or partially assembled on the arm and temporarily secured to the humeral brace component 180 and a radius/ulnar brace component 182. The humeral brace component 180 is secured to the humerus, e.g., by straps, to hold the humerus in a laterally extended position from the shoulder. The radius/ulnar brace component 182 is secured to the radius/ulna, e.g. by straps, to hold the radius/ulna while flexed at the elbow to point the hand in a superior direction facing the shoulder.

The c-arm 106 is oriented relative to the supracondylar region for lateral and a-p radiographic imaging of the supracondylar fracture, as shown in FIG. 48. This is also shown in FIGS. 30A (lateral imaging) and 31A (a-p imaging). FIG. 49 shows a lateral image of the displaced distal and proximal bone fragments of supracondylar fracture of a right arm, prior to reduction.

B. Mechanically Achieving Distal Traction

Figure 51:
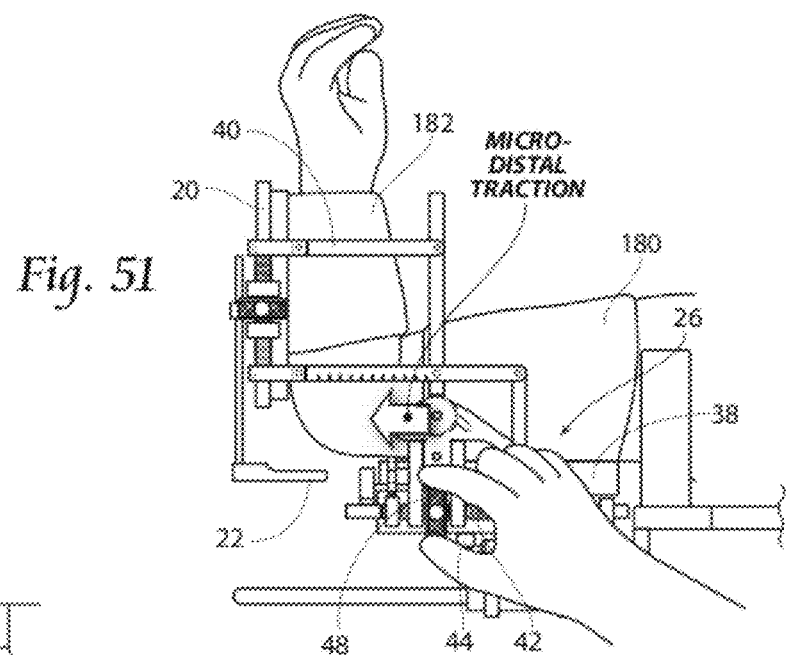
Figure 52:
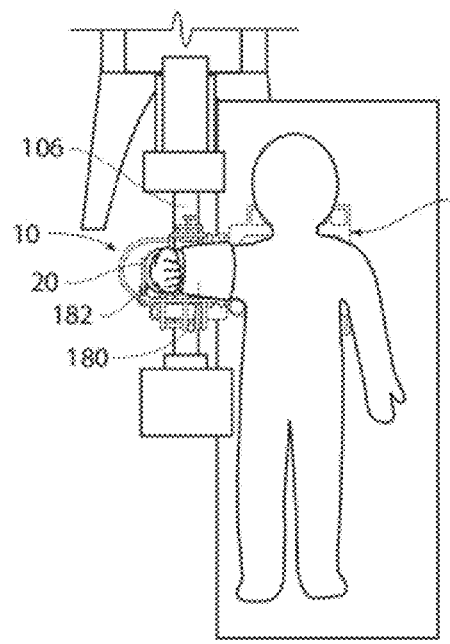
Figure 53:
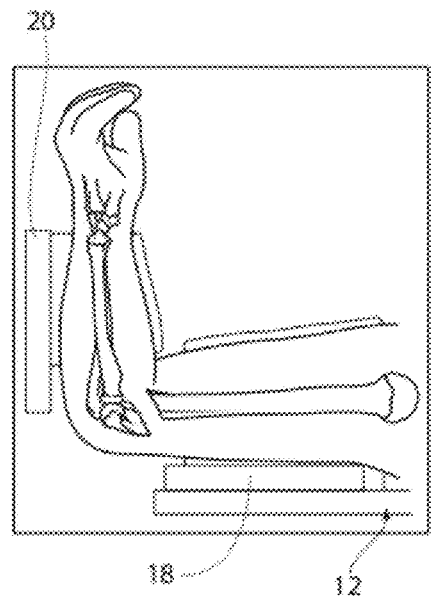

As FIGS. 50 and 51 show, the caregiver operates the distal traction mechanical force reduction assembly 26, as previously described, to move the radius/ulna support carriage 20 in a Left-ward path in the horizontal plane (refer back to FIG. 18A). The humeral support carriage 18 remains stationary during Left-ward translation of the radius/ulna support carriage 20. As previously explained, the Left-ward translation can be achieved in a macro-fashion (as FIG. 50 shows) or in a micro-fashion (as FIG. 51 shows). Aided by lateral radiographic imaging (as FIG. 52 shows), the caregiver mechanically applies linear Left-ward translation (in Macro- and/or micro-fashion) in a controlled fashion to move the radius/ulna support carriage 20 in a linear path Left-ward, laterally farther from the humeral support carriage 18. The distal traction mechanical force reduction assembly 26 mechanically achieves distal traction along the anatomic x-axis of the coordinate system of the supracondylar region (refer back to FIG. 11A), by separating the distal bone fragment and the proximal bone fragment along the anatomic x-axis (as confirmed by the lateral radiographic image of FIG. 53), until a desired alignment in this first anatomic orientation is achieved. The caregiver mechanically maintains the desired alignment in the first anatomic orientation, as previously described.

C. Mechanically Achieving Superior Traction

Figure 54:
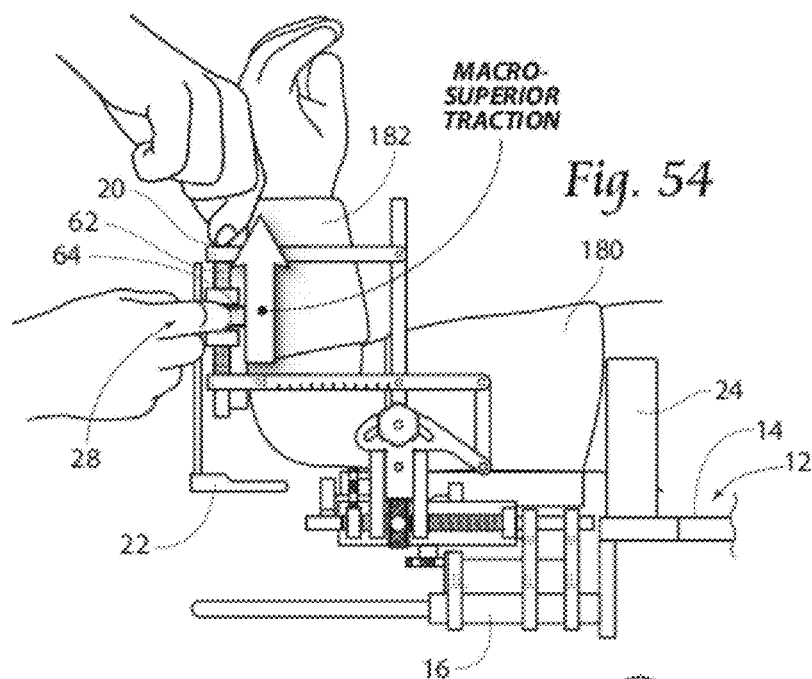
Figure 55:
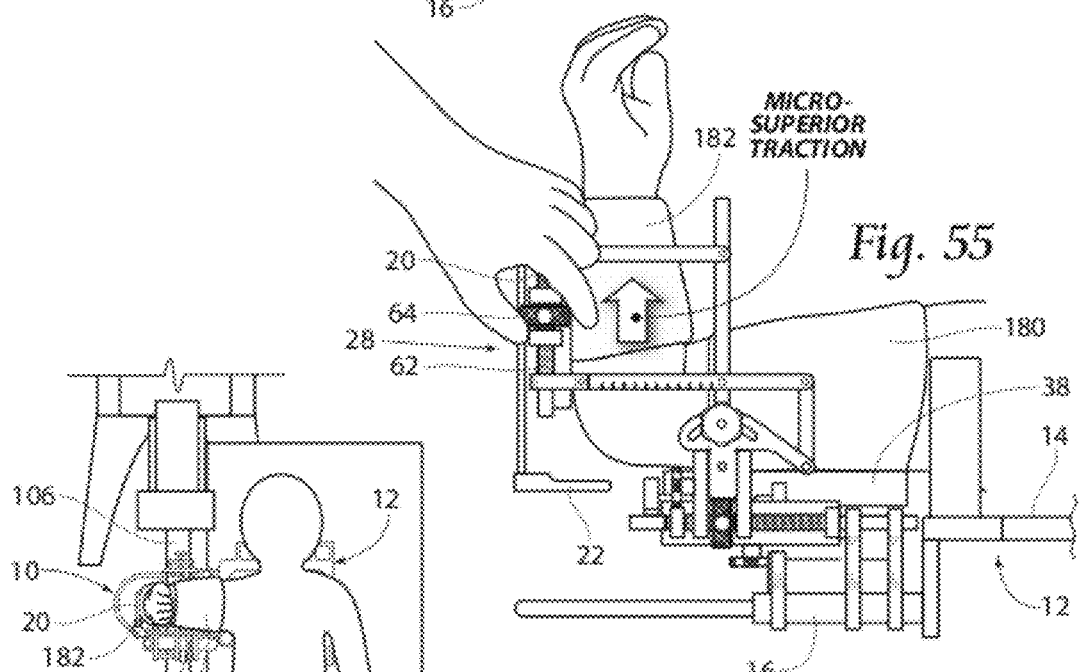
Figure 56:
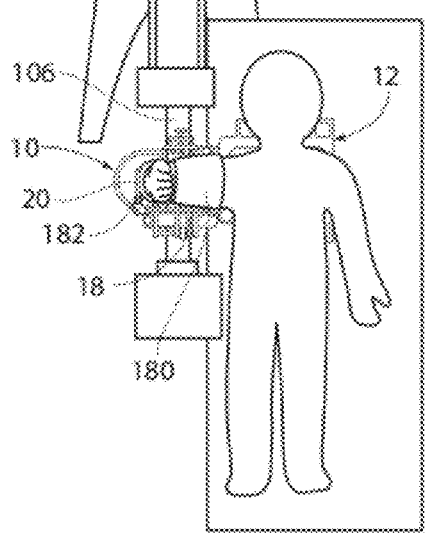
Figure 57:
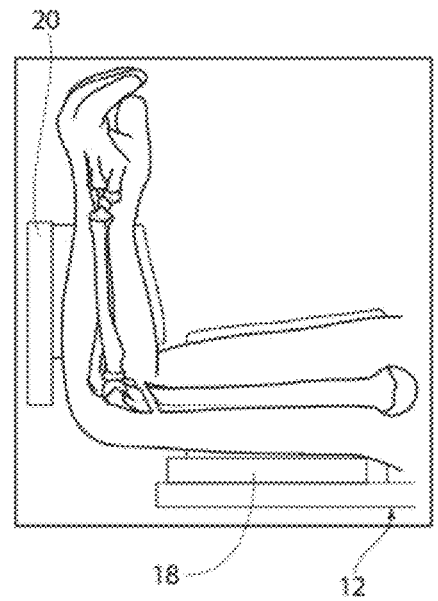

As FIGS. 54 and 55 show, the caregiver operates the superior traction mechanical force reduction assembly 28, as previously described, to move the radius/ulna support carriage 20 in a linear Top-ward path in the vertical plane (refer back to FIG. 19A). The humeral support carriage 18 remains stationary during Top-ward translation of the radius/ulna support carriage 20. As previously explained, the Top-ward translation can be achieved in a macro-fashion (as FIG. 54 shows) or in a micro-fashion (as FIG. 55 shows). Aided by lateral radiographic imaging (as FIG. 56 shows), the caregiver mechanically applies linear Top-ward translation (in Macro- and/or micro-fashion) in a controlled fashion to move the radius/ulna support carriage 20 in a linear path Top-ward, laterally farther from the humeral support carriage 18. The superior traction mechanical force reduction assembly 28 mechanically achieves superior traction along the anatomic y-axis (refer back to FIG. 12A) by separating the distal bone fragment and the proximal fracture fragment along the anatomic y-axis (as confirmed by the lateral radiographic image of FIG. 57), until a desired alignment in this second anatomic orientation is achieved. Because the first anatomic orientation is being mechanically maintained, achieving this second anatomic orientation does not alter the first-achieved anatomic orientation (in this case, distal traction). The caregiver mechanically maintains the desired alignment in the second anatomic orientation as well, as previously described.

D. Mechanically Achieving Lateral Traction

Figure 58:
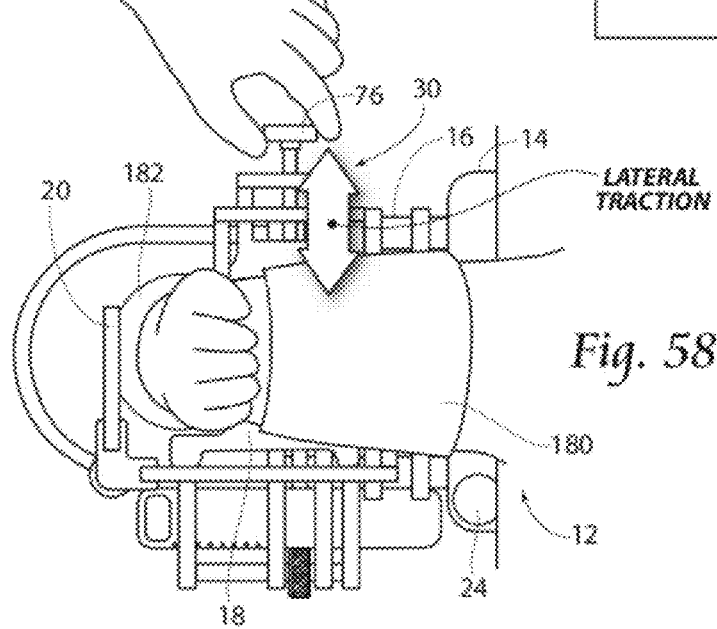
Figure 59:
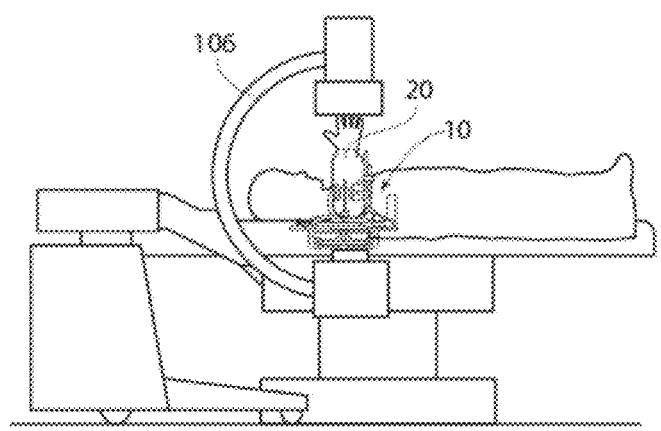
Figure 60:
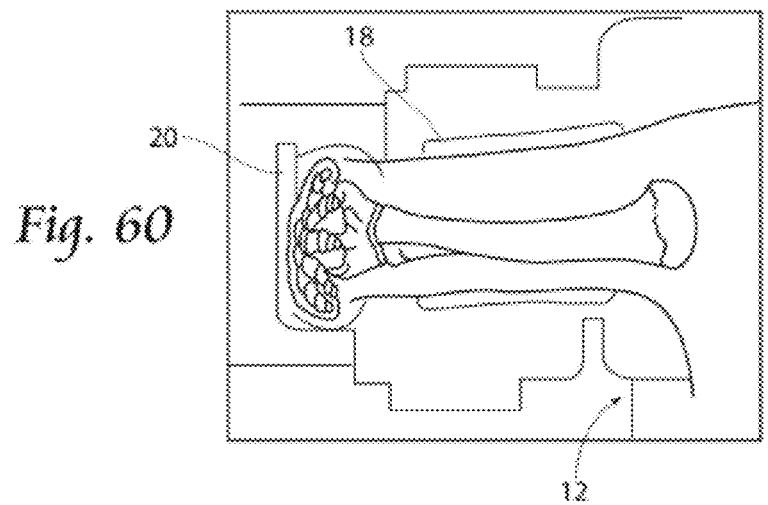

As FIG. 58 shows, the caregiver operates the lateral traction mechanical force reduction assembly 30, as previously described, to move the humeral support carriage 18 in a linear path in a horizontal plane in a Front direction (Front-ward) and a Back direction (Back-ward) on appendage support platform 16 (refer back to FIG. 20A). The radius/ulna support carriage 20 remains stationary during linear Front-ward and Back-ward movement of the humeral support carriage 18. As previously explained, in the exemplary embodiment, the Front-ward and Back-ward translation is achieved in a micro-fashion (as FIG. 58 shows). Aided by a-p radiographic imaging (as FIG. 59 shows), the caregiver mechanically applies linear Front-ward and Back-ward translation in a controlled fashion to move the humeral support carriage 18 in a linear path Front-ward and Back-ward. The superior traction mechanical force reduction assembly 28 mechanically achieves lateral traction along the anatomic z-axis (refer back to FIG. 13A) by mechanically returns proximal and distal bone fragments that have been medially displaced along the anatomic z-axis back toward the native state of alignment (as confirmed by the a-p radiographic image of FIG. 60), until a desired alignment in this third anatomic orientation is achieved. Because the first and second anatomic orientations are being mechanically maintained, achieving this third anatomic orientation does not alter the first- and second-achieved anatomic orientations (in this case, distal traction and superior traction). The caregiver mechanically maintains the desired alignment in the third anatomic orientation as well, as previously described.

E. Mechanically Achieving Varus/Valgus Rotation

Figure 61:
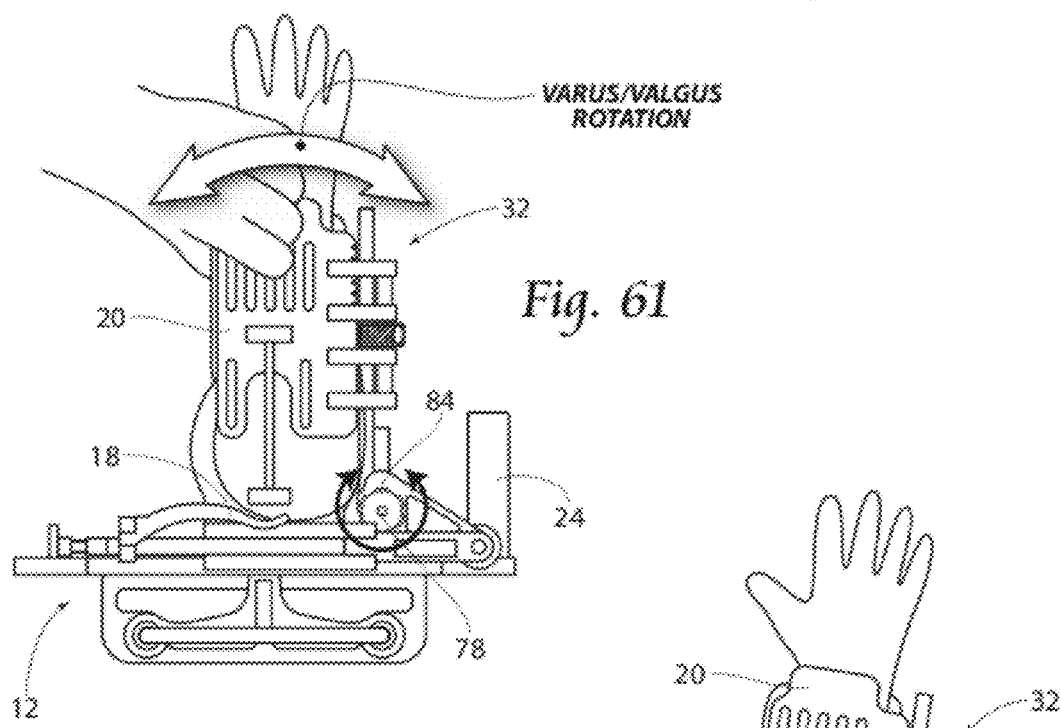
Figure 62:
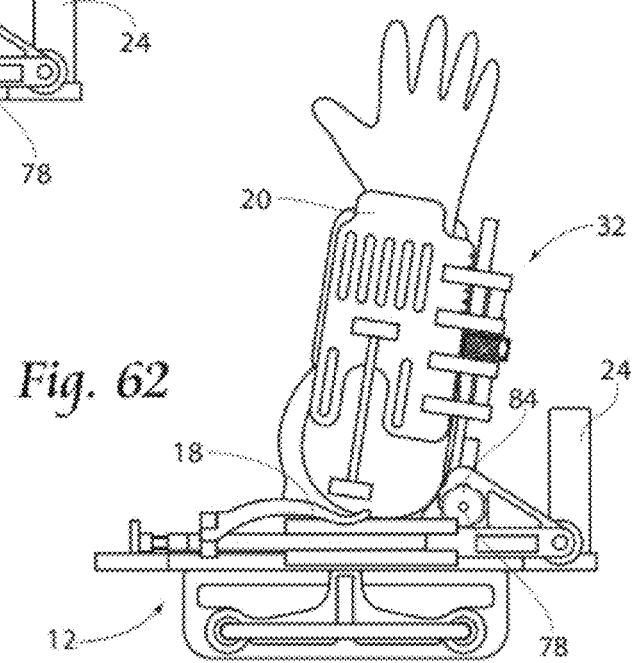
Figure 63:
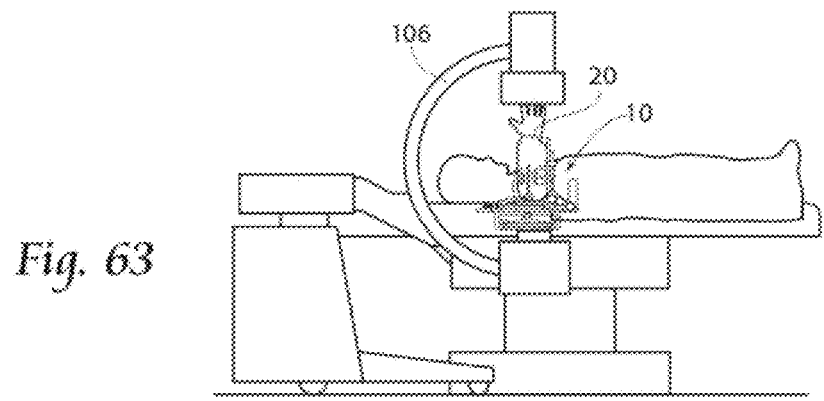
Figure 64:
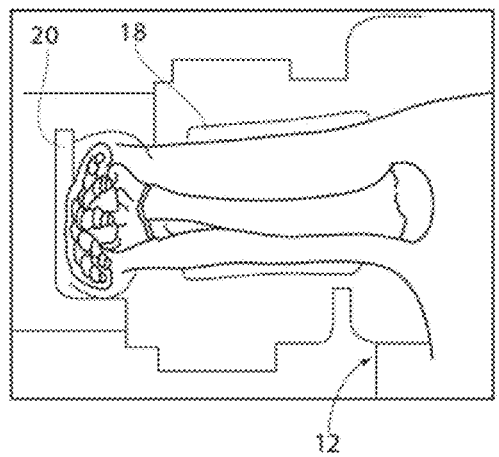

As FIGS. 61 and 62 show, the caregiver operates the varus/valgus rotation mechanical force reduction assembly 32, as previously described, to tilt the radius/ulna carriage Back-wards and Front-wards (refer back to FIG. 21A) about the pivot point connection system 78. The humeral support carriage 18 remains stationary as the radius/ulna carriage tilts Back-wards and Front-wards. As previously explained, in the exemplary embodiment, the Front-ward and Back-ward translation is achieved in a macro-fashion (as FIGS. 61 and 62 show). Aided by a-p radiographic imaging (as FIG. 63 shows), the caregiver mechanically applies Front-ward and Back-ward rotations in a controlled fashion to tilt the radius/ulna carriage Front-ward and Back-ward. The varus/valgus rotation mechanical force reduction assembly 32 mechanically achieves varus/valgus rotation about the anatomic x-axis (refer back to FIG. 14A) by applying a rotational force vector (torque) about the anatomic x-axis to the fractured end of the distal bone fragment (held in the radius/ulna support carriage 20). The varus/valgus rotation force, mechanically applied by the varus/valgus rotation mechanical force reduction assembly 32, pivots the fractured end of the distal bone fragment about the longitudinal axis of the proximal bone fragment, to return the proximal and distal bone fragments, which have been rotationally displaced due to the fracture, back toward the native state of alignment (as confirmed by the a-p radiographic image of FIG. 64), until a desired alignment in this fourth anatomic orientation is achieved, at which point the locking mechanism 84 is operated. Because the first, second, and third anatomic orientations are being mechanically maintained, achieving this fourth anatomic orientation does not alter the first-, second-, or third-achieved anatomic orientations (in this case, distal traction, superior traction, and lateral traction). The caregiver mechanically maintains the desired alignment in the fourth anatomic orientation as well, as previously described.

F. Mechanically Achieving Pronation/Supination Rotation

Figure 65:
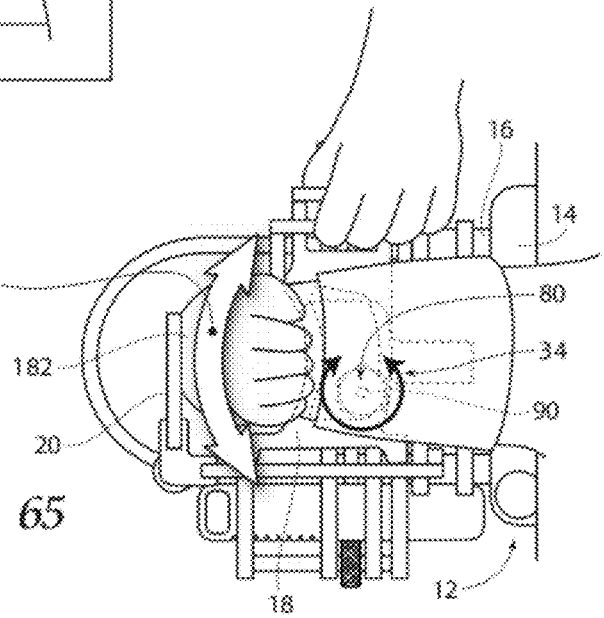
Figure 66:
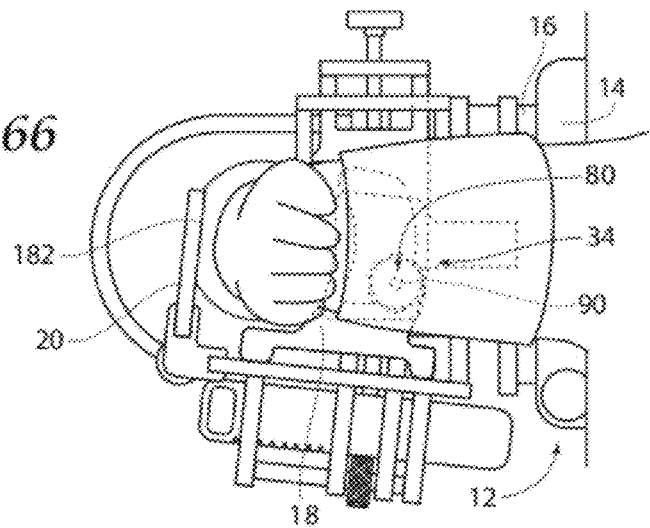
Figure 67:
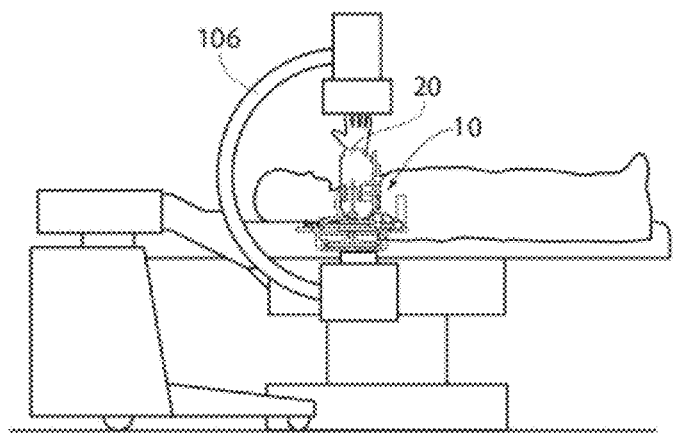
Figure 68:
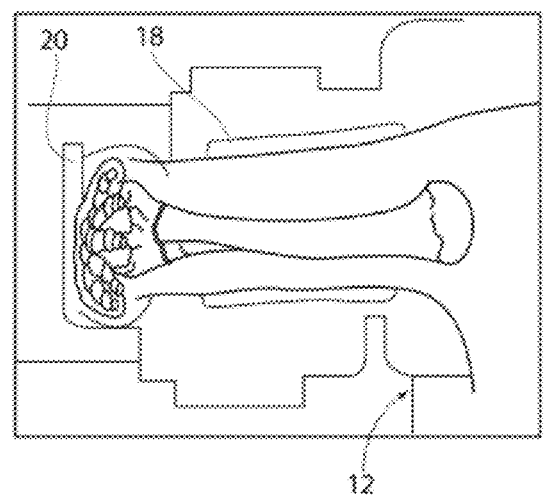

As FIGS. 65 and 66 show, the caregiver operates the pronation/supination rotation mechanical force reduction assembly 34, as previously described, to swing the radius/ulna carriage in a horizontal plane Back-ward and Front-ward about the Top-to-Bottom virtual center of rotation (refer back to FIG. 22C). The humeral support carriage 18 remains stationary as the radius/ulna carriage swings Back-wards and Front-wards. As previously explained, in the exemplary embodiment, the Front-ward and Back-ward translation is achieved in a micro-fashion (as FIGS. 65 and 66 show). Aided by a-p radiographic imaging (as FIG. 67 shows), the caregiver mechanically applies Front-ward and Back-ward rotations in a controlled fashion to swing the radius/ulna carriage Front-ward and Back-ward. The pronation/supination rotation mechanical force reduction assembly 34 mechanically achieves pronation/supination rotation about the anatomic y-axis (refer back to FIG. 15A) by swinging the radius/ulna support carriage 20 in an arcuate path in a horizontal plane Front-ward and Back-ward about the Top-to-Bottom virtual center of rotation axis relative to the stationary humeral support carriage 18. As the radius/ulna support carriage 20 swings Front-ward and Back-ward in the horizontal plane about the Top-to-Bottom virtual center of rotation axis relative to stationary humeral support carriage 18, a rotational force vector (torque) is applied about the anatomic y-axis to the fractured end of the distal bone fragment (held in the radius/ulna support carriage 20). The pronation/supination rotation force, mechanically applied by the pronation/supination rotation mechanical force reduction assembly 34, pivots the fractured end of the distal bone fragment about the longitudinal axis of distal bone fragment, back toward the native state of alignment (as confirmed by the a-p radiographic image of FIG. 68), until a desired alignment in this fifth anatomic orientation is achieved, at which time the locking mechanism 90 is actuated. Because the first, second, third, and fourth anatomic orientations are being mechanically maintained, achieving this fifth anatomic orientation does not alter the first-, second-, third-, or fourth-achieved anatomic orientations (in this case, distal traction, superior traction, lateral traction, and varus/valgus rotation). The caregiver mechanically maintains the desired alignment in the fifth anatomic orientation as well, as previously described.

G. Mechanically Achieving Flexion/Extension Rotation

Figure 69:
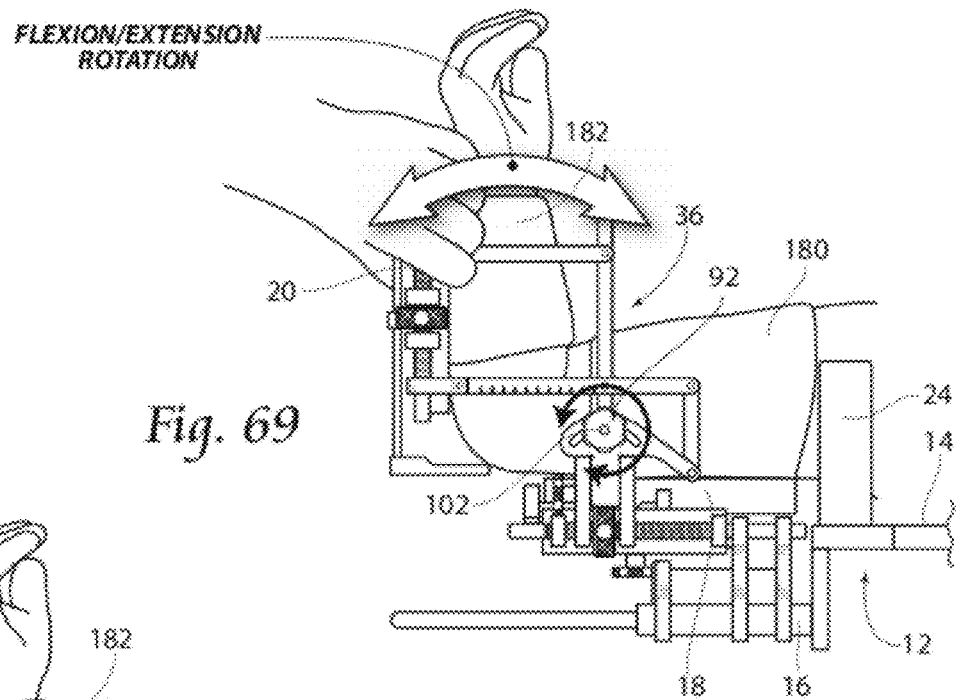
Figure 70:
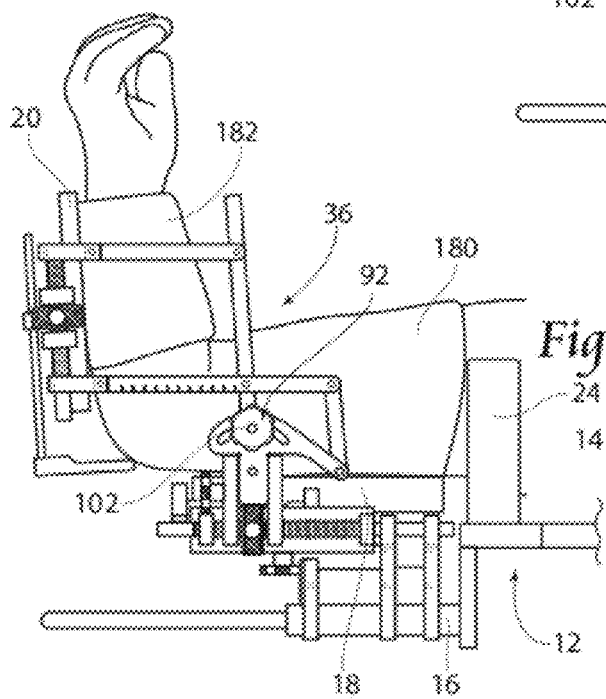
Figure 71:
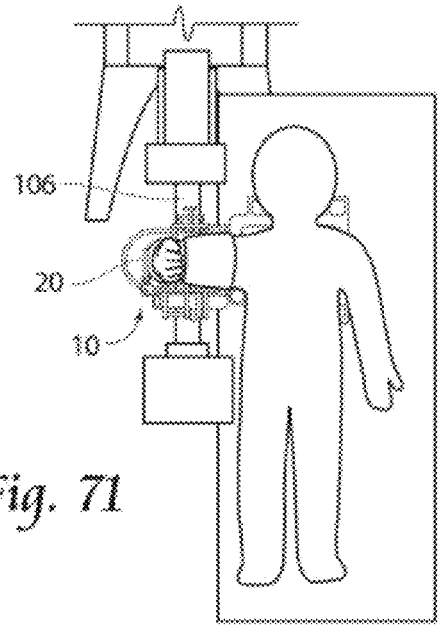
Figure 72:
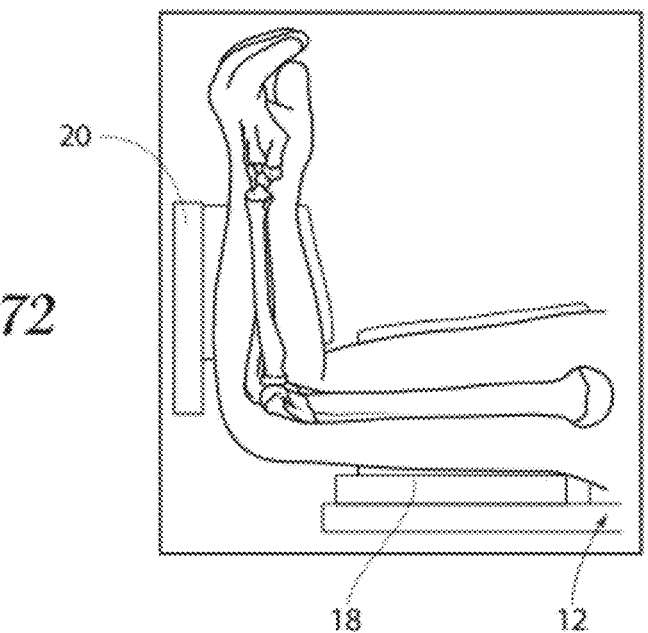

As FIGS. 69 and 70 show, the caregiver operates the flexion/extension rotation mechanical force reduction assembly 36, as previously described, to tilt the radius/ulna support carrier Left-ward (refer back to FIG. 23A) about the pivot point 92. The humeral support carriage 18 remains stationary as the radius/ulna carriage tilts Left-ward. As previously explained, in the exemplary embodiment, the Left-ward and Back-ward translation is achieved in a macro-fashion (as FIGS. 69 and 70 show). Aided by lateral radiographic imaging (as FIG. 71 shows), the caregiver mechanically applies Left-ward rotation in a controlled fashion to swing the radius/ulna carriage Left-ward. The flexion/extension rotation mechanical force reduction assembly 36 mechanically achieves flexion/extension rotation about the anatomic z-axis (refer back to FIG. 16A) by tilting the radius/ulna support carriage 20 in an arcuate path in a vertical plane Left-ward about the Front-to-Back axis relative to the stationary humeral support carriage 18. As the radius/ulna support carriage 20 tilts Left-ward in the vertical plane relative to stationary humeral support carriage 18, a rotational force vector (torque) is applied about the anatomic z-axis to the fractured end of the distal bone fragment (held in the radius/ulna support carriage 20). The flexion/extension rotation force, mechanically applied by the flexion/extension rotation mechanical force reduction assembly 36, pivots the fractured end of the distal bone fragment about the longitudinal axis of the proximal bone fragment, to return the proximal and distal bone fragments, which have been rotationally displaced due to the fracture, back toward the native state of alignment (as confirmed by the lateral radiographic image of FIG. 72), until a desired alignment in this sixth anatomic orientation is achieved, at which point the locking mechanism 102 is actuated. Because the first, second, third, fourth, and fifth anatomic orientations are being mechanically maintained, achieving this sixth anatomic orientation does not alter the first-, second-, third-, fourth-, or fifth-achieved anatomic orientations (in this case, distal traction, superior traction, lateral traction, varus/valgus rotation, and pronation/supination rotation). The caregiver mechanically maintains the desired alignment in the six anatomic orientation as well, as previously described.

H. Fracture Reduction Review

To summarize, the fracture reduction method, as just described, includes (i) supporting a body region having the bone fracture on a frame, (ii) operating a first reduction mechanism on the frame 12 to apply to the bone fracture a first predefined force reduction vector that returns the bone fracture to a corrective alignment in a first anatomic orientation, (iii) mechanically maintaining the corrective alignment in the first anatomic orientation, (iv) independent of (ii) and (iii), operating a second reduction mechanism on the frame to apply a second predefined force reduction vector that returns the bone fracture to a corrective alignment in a second anatomic orientation different than the first anatomic orientation without altering the corrective alignment in the first anatomic orientation, and (v) mechanically maintaining the corrective alignment in the second anatomic orientation.

The force reduction assemblies carried by the reduction frame 12 make possible a mechanically-achieved complete composite reduction of a complex fracture. In the exemplary case of a supracondylar fracture, the method can the operation of up to six force reduction assemblies, corresponding to the up to six mechanical force reductions identified for a supracondylar fracture; namely, (i) a distal traction mechanical force reduction assembly 26; (ii) a superior traction mechanical force reduction assembly 28; (iii) a lateral traction mechanical force reduction assembly 30; (iv) a varus/valgus rotation mechanical force reduction assembly 32; (v) a pronation/supination rotation mechanical force reduction assembly 34; and (vi) a flexion/extension rotation mechanical force reduction assembly 36.

Reduction can proceed in a systematic, stepwise fashion, by applying predefined force reduction vectors one at a time, and mechanically maintaining one corrective alignment before proceeding with the next, until alignment in all desired anatomic orientations is achieved. Alternatively, however, the caregiver can chose to proceed to apply two or more predefined force reduction vectors concurrently, to achieve concurrent corrective alignments in more than one anatomic orientation at the same time, and mechanically maintaining the concurrently-achieved corrective alignments. The former, stepwise approach is preferred, particularly when the predefined force reduction vectors are applied with manual control and/or guidance. Still, it should be appreciated that the technical features of the invention can be achieved without a stepwise approach.

I. Mechanically Achieving Reduction Fixing Guidance

Figure 73:
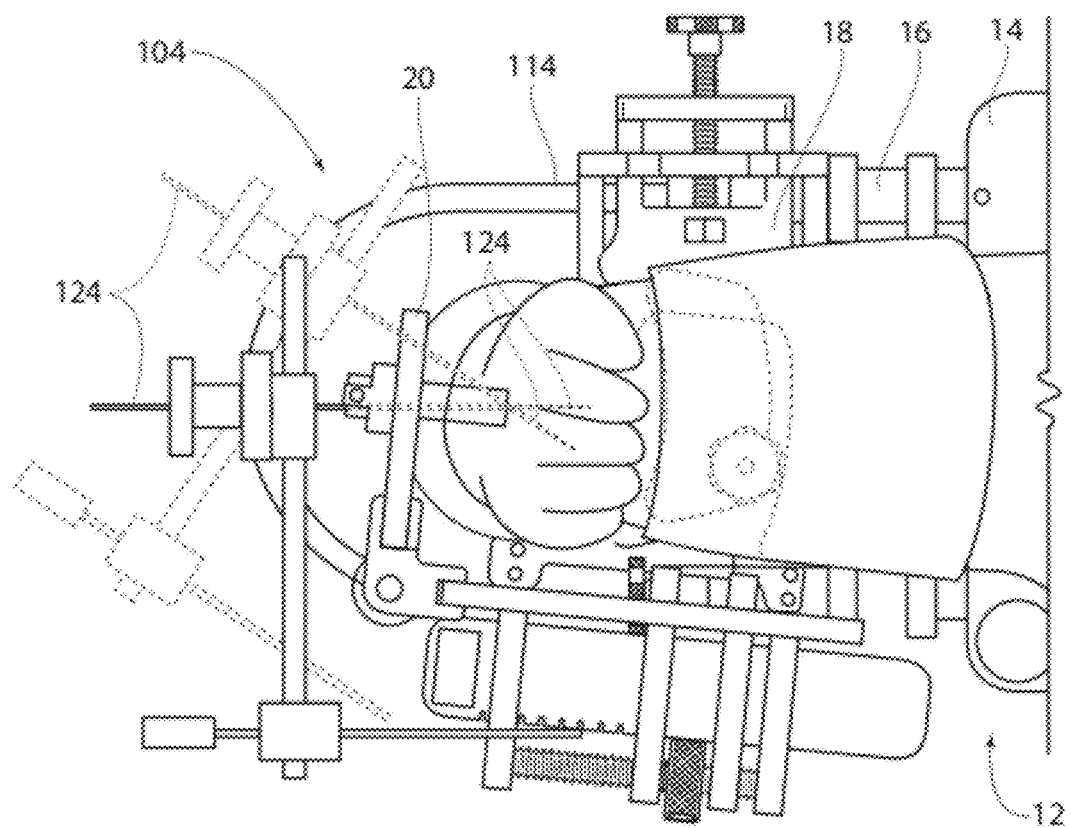

Once mechanical force reduction is achieved, the caregiver can, without removal of the orthotic brace 178 and without otherwise altering the composite reduction mechanically achieved, proceed to operate a mechanical bone fixing instrument or tool 104 on the frame 12 like that shown in FIGS. 33/34 or FIGS. 39/40. As shown in FIG. 70, by operating the mechanical bone fixing instrument or tool 104, the caregiver guides insertion of one or more bone fixing devices to maintain the desired alignment in the anatomic orientations, as previously described, and as generally shown for the purpose of illustration in FIG. 73.

To summarize, the method for mechanically guiding a fixing of a bone fracture reduction comprising (i) supporting a body region having bone fracture reduction on a frame, (ii) providing a guide that defines a path along which a bone fixing device can be placed to fix the bone fracture reduction, (iii) moving the guide on a first mount on the frame 12 relative the bone fracture reduction in a range of positions orientated with the bone fracture reduction in a first plane to guide placement of the bone fixing device in the first plane, (iv) mechanically maintaining a desired orientation in the first plane, (v) moving the guide on a second mount relative the bone fracture reduction in a range of positions oriented with the bone fracture reduction within a second plane, different than the first plane, to guide placement of the bone fixing device in the second plane, (vi) mechanically maintaining with a desired orientation in the second plane, and (vii) placing the bone fixing device through the guide into the bone fracture reduction to fix the bone fracture reduction.

Desirably, at least one radio-opaque guide is provided parallel to and axially aligned with the path of the bone fixing device 142 in at least one the respective planes. In this arrangement, before placing the bone fixing device 142 through the guide, a radiographic image is generated of the radio-opaque guide relative to the bone fracture reduction As before explained, either the first or second plane can comprise a horizontal plane, a vertical plane, or a plane that intersects a horizontal or vertical plane at an angle.

J. Conclusion

Figure 45:
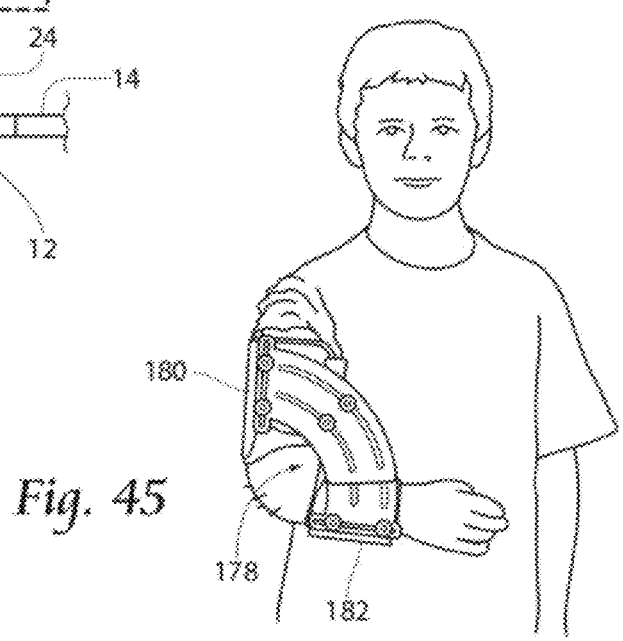
FIG. 45 is a perspective view of the orthotic shown in FIG. 43 being worn by an individual after the bone fracture has been mechanically reduced and fixed.

Once mechanically guided fixing of the reduced bone fracture is achieved, the orthotic brace 178 can be released from the reduction frame 12, as FIG. 45 shows, without altering the orientation of bone structures in the reduced and fixed fracture. The individual is free to ambulate as healing occurs and the supcondylar region returns to its native state prior to injury.

Each of the mechanical force reduction assemblies is sized and configured to independently mechanically manipulate the arm resting in the humeral support carriage 18 and the radius/ulna support carriage 20. Each mechanical force reduction assembly functions independently of the other mechanical force reduction assemblies, to independently apply and maintain one of the prescribed mechanical reduction forces to the fracture. Concurrently, the mechanical force reduction assemblies mechanically apply and maintain a plurality of independent mechanical reduction forces, to thereby mechanically reduce the fracture in the desired reduction planes.

In the context of reducing a supracondylar fracture, there are six mechanical force reduction assemblies. The six mechanical force reduction assemblies correspond to six mechanical force reductions identified for a supracondylar fracture. In this context, the mechanical force reduction assemblies carried by the main appendage support platform 16 comprise (i) a distal traction mechanical force reduction assembly 26; (ii) a superior traction mechanical force reduction assembly 28; (iii) a lateral traction mechanical force reduction assembly 30; (iv) a varus/valgus rotation mechanical force reduction assembly 32; (v) a pronation/supination rotation mechanical force reduction assembly 34; and (vi) a flexion/extension rotation mechanical force reduction assembly 36. Concurrently, the six mechanical force reduction assemblies carried by the reduction frame 12 make possible a mechanically-achieved complete composite reduction of a supracondylar fracture and a mechanically guided fixing of the mechanically-achieved complete composite reduction.

K. Robotic/Computer Control

Figure 74:
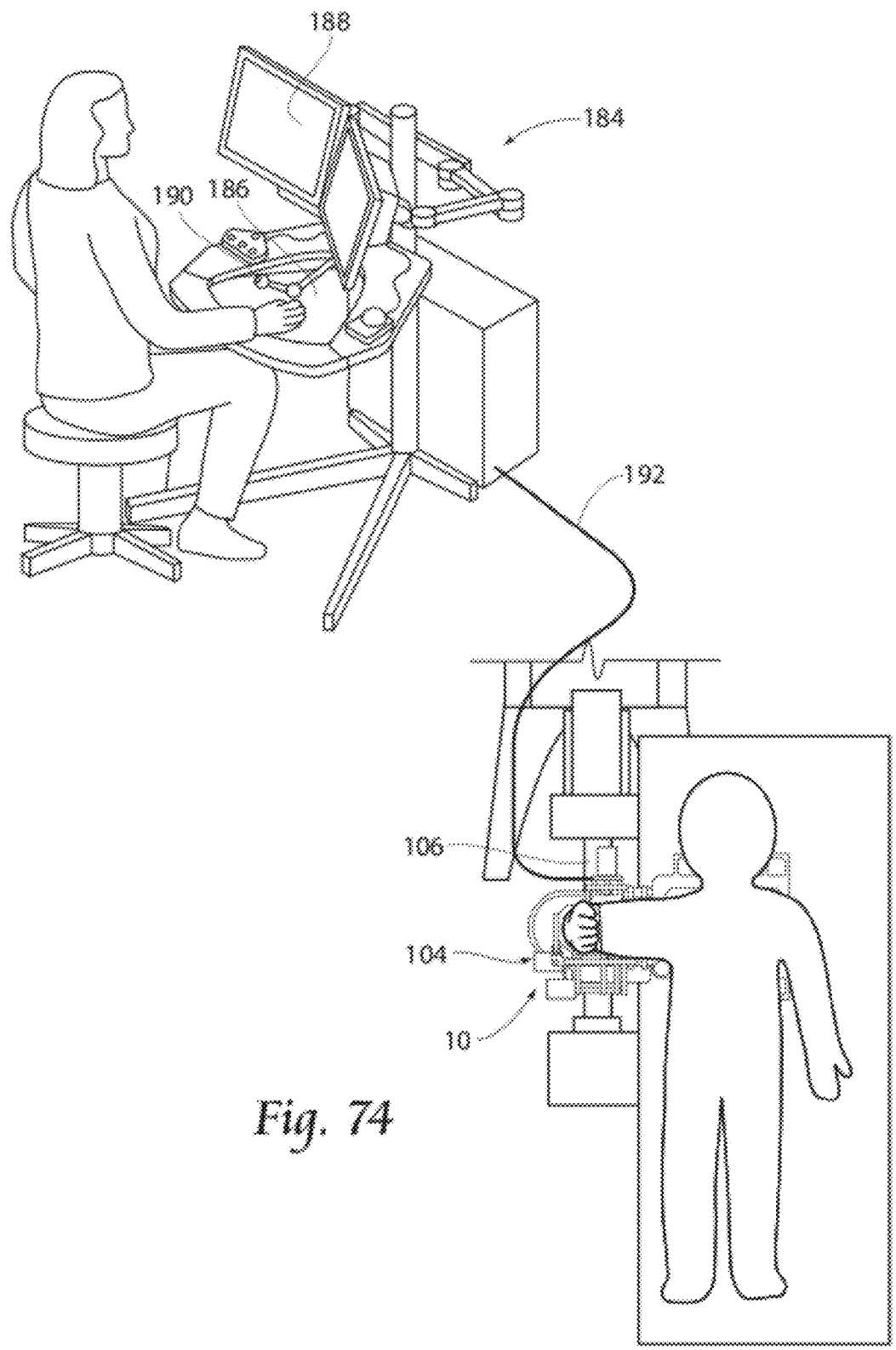
FIG. 74 is a perspective view of a system that includes robotic/computer control for achieving mechanical force reduction of a bone fracture by the application of force reduction vectors.

A fracture reduction system 10 comprising one or more mechanical force reduction assemblies and/or mechanical reduction fixing guidance mechanisms 104 can include a robotic/computer control system 184 (see FIG. 74). The robotic/computer control system 184 includes a remote control console 186 that includes a radiographic image viewer 188 coupled to the c-arm 106 mechanism to facilitate imaging, as well as one or more instrument drivers coupled by a communication link 192 to the mechanical force reduction assemblies and/or mechanical reduction fixing guidance mechanisms carried by the reduction frame 12. The communication link 192 transfers control signals from the instrument drivers to the mechanical force reduction assemblies and/or mechanical reduction fixing guidance mechanisms. The control signals operate the mechanical force reduction assemblies and/or mechanical reduction fixing guidance mechanisms in the manners described, under radiographic image guidance. The fracture reduction system comprising a robotic/computer control system makes it possible to achieve, mechanically and under precise, robotic/computer control, a complete composite reduction of a fracture and/or a mechanically guided fixing of a mechanically-achieved complete composite reduction of a fracture.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A bone fracture reduction system comprising
    a frame that is sized and configured to support a body region having a bone fracture
    a first reduction mechanism on the frame that is sized and configured to apply to the bone fracture a first mechanical force vector that moves the bone fracture into alignment in a first anatomic orientation, including a mechanism that is sized and configured to mechanically interact with the first reduction mechanism to maintain a desired alignment in the first anatomic orientation, and
    a second reduction mechanism on the frame that is sized and configured to apply to the bone fracture, independent of the application of the first mechanical force vector, a second mechanical force vector that moves the bone fracture into alignment in a second anatomic orientation different than the first anatomic orientation, including a mechanism that is sized and configured to mechanically interact with the second reduction mechanism to maintain a desired alignment in the second anatomic orientation
    and further including an orthotic that is sized and configured to be assembled on the body region about the bone fracture, and
    wherein the frame includes a carrier for the orthotic either partially or fully assembled on the body region.

2. A system as defined in claim 1
    and further including a mechanical guidance mechanism on the frame that is sized and configured to guide placement of one or more bone fixing devices to maintain desired alignments in the first and second anatomic orientations.

3. A system as defined in claim 1
    wherein at least one of the first and second mechanical force vectors is applied along a horizontal axis.

4. A system as defined in claim 1
    wherein at least one of the first and second mechanical force vectors is applied along a vertical axis.

5. A system as defined in claim 1
    wherein at least one of the first and second mechanical force vectors comprises a torque applied about an axis.

6. A system as defined in claim 1
    wherein said carrier allows for releasable attachment of the orthotic either partially or fully assembled on the body region.

7. A system as defined in claim 1
    and further including at least one additional reduction mechanism on the frame that is sized and configured to apply to the bone fracture, independent of both the first and second mechanical force vectors, at least one additional mechanical force vector that moves the bone fracture into alignment in at least one additional anatomic orientation, different than the first and second anatomic orientations, including a mechanism that is sized and configured to mechanically interact with the at least one additional reduction mechanism to maintain a desired alignment in the at least one additional anatomic orientation.

8. A system as defined in claim 1
wherein the bone region is defined by anatomic x-, y-, and z-axes,
wherein one of the first and second mechanical force vectors is applied relative to one of the anatomic x-, y-, and z-axes, and
wherein the other one of the first and second mechanical force vectors is applied relative to a different one of the anatomic x-, y-, and z-axes.

9. A system as defined in claim 8
wherein one of the first and second mechanical force vectors is applied as a linear force along one of the anatomic x-, y-, and z-axes.

10. A system as defined in claim 8
wherein one of the first and second mechanical force vectors is applied as a torque about one of the anatomic x-, y-, and z-axes.

11. A system as defined in claim 8
wherein one of the first and second mechanical force vectors is applied as a linear force along one of the anatomic x-, y-, and z-axes, and
wherein the other one of the first and second mechanical force vectors is applied as a torque about one of the anatomic x-, y-, and z-axes.

12. A system as defined in claim 1
and further including a robotic/computer control system coupled to at least one of the first and second reduction mechanisms.

13. A fracture reduction system for an arm bone region defined by anatomic x-, y-, and z-axes and having a supracondylar fracture, the system comprising
a frame that is sized and configured to support the arm bone region having the supracondylar fracture
a distal traction mechanical force reduction assembly on the frame that is sized and configured to apply to the supracondylar fracture a first mechanical force vector that moves the supracondylar fracture into alignment in a first anatomic orientation along the anatomic x-axis, achieving, at least in part, distal traction of the supracondylar fracture, including a mechanism that is sized and configured to mechanically interact with the distal traction mechanical force reduction assembly to maintain a desired alignment in the first anatomic orientation, and
a second mechanical force reduction assembly on the frame that is sized and configured to apply to the supracondylar fracture, independent of the first mechanical force vector, a second mechanical force reduction vector that moves the supracondylar fracture into alignment in a second anatomic orientation, different than the first anatomic orientation, relative to one of the anatomic x-, y-, and z-axes, without altering a desired alignment in the first anatomic orientation, the second anatomic orientation achieving, at least in part, one of superior traction, lateral traction, varus/valgus rotation, pronation/supination rotation, and flexion/extension rotation or the supracondylar fraction, the second mechanical force reduction assembly including a mechanism that is sized and configured to mechanically interact with the second mechanical force reduction assembly to maintain a desired alignment in the second anatomic orientation
and further including an orthotic that is sized and configured to be assembled on the arm bone region about the supracondylar fracture, and
wherein the frame includes a carrier for the orthotic either partially or fully assembled on the arm bone region.

14. A system as defined in claim 13
and further including a mechanical guidance mechanism on the frame that is sized and configured to guide placement of one or more bone fixing devices to maintain the desired alignment in the first and second anatomic orientations.

15. A system as defined in claim 13
the carrier allows for releasable attachment of the orthotic either partially or fully assembled on the arm bone region.

16. A system as defined in claim 13
wherein the second mechanical force vector comprises a linear force applied along one of the anatomic axes.

17. A system as defined in claim 13
wherein the second mechanical force vector comprise a torque applied about one of the anatomic axes.

18. A system as defined in claim 13
and further including a robotic/computer control system coupled to at least one of the distal traction mechanical force reduction assembly and the second mechanical force reduction assembly.

19. A fracture reduction method comprising
(i) supporting a body region having the bone fracture on a frame,
(ii) operating a first reduction mechanism on the frame to apply to the bone fracture a first predefined force reduction vector that returns the bone fracture to a corrective alignment in a first anatomic orientation,
(iii) mechanically maintaining the corrective alignment in the first anatomic orientation,
(iv) independent of (ii) and (iii), operating a second reduction mechanism on the frame to apply a second predefined force reduction vector that returns the bone fracture to a corrective alignment in a second anatomic orientation different than the first anatomic orientation without altering the corrective alignment in the first anatomic orientation,
(v) mechanically maintaining the corrective alignment in the second anatomic orientation; and
further including either partially or fully assembling an orthotic on the body region having the bone fracture, and
wherein (i) includes placing the orthotic either partially or fully assembly on the body region on the frame.

20. A method as defined in claim 19
and further including operating a mechanical guidance mechanism on the frame to guide placement of one or more bone fixing devices to maintain the corrective alignment in the first and second anatomic orientations.

21. A fracture reduction method comprising
(i) identifying a bone region having a bone fracture and defined by anatomic x-, y-, and z-axes, a frame sized and configured to support the bone region having the bone fracture,
(ii) supporting the bone region having the bone fracture on a,
(iii) operating a first reduction mechanism on the frame to apply to the bone fracture a first predefined force reduction vector that returns the bone fracture to a corrective alignment in a first anatomic orientation relative to the anatomic x-axis,
(iv) mechanically maintaining the corrective alignment in the first anatomic orientation,
(v) independent of (iii) and (iv), operating a second reduction mechanism on the frame to apply a second predefined force reduction vector that returns the bone fracture to a corrective alignment in a second anatomic orientation relative to the anatomic y-axis without altering the corrective alignment in the first anatomic orientation, (vi) mechanically maintaining the corrective alignment in the second anatomic orientation, (vii) independent of (iii), (iv), (v), and (vi), operating a third reduction mechanism on the frame to apply a third predefined force reduction vector that returns the bone fracture to a corrective alignment in a third anatomic orientation along the anatomic z-axis without altering the corrective alignment in either the first or second anatomic orientations (viii) mechanically holding stationary the corrective alignment in the third anatomic orientation; and further including either partially or fully assembling an orthotic on the bone region having the bone fracture, and wherein (ii) includes placing the orthotic either partially or fully assembled on the bone region on the frame.

22. A method according to claim 21 and further including operating a mechanical guidance mechanism on the frame to guide placement of one or more bone fixing devices to maintain the corrective alignment in the first, second, and third anatomic orientations.

23. A fracture reduction method for an arm bone region defined by anatomic x-, y-, and z-axes and having a supracondylar fracture, the method comprising (i) supporting the arm bone region having the supracondylar fracture on a frame, (ii) operating a distal traction mechanical force reduction assembly on the frame to apply to the supracondylar fracture a first mechanical force vector that moves the supracondylar fracture into alignment in a first anatomic orientation along the anatomic x-axis, achieving, at least in part, distal traction of the supracondylar fracture, (iii) mechanically maintaining a desired alignment in the first anatomic orientation, and (iv) operating a second mechanical force reduction assembly on the frame to apply to the supracondylar fracture, independent of the first mechanical force vector, a second mechanical force reduction vector that moves the supracondylar fracture into alignment in a second anatomic orientation, different than the first anatomic orientation, relative to one of the anatomic x-, y-, and z-axes, without altering a desired alignment in the first anatomic orientation, the second anatomic orientation achieving, at least in part, one of superior traction, lateral traction, varus/valgus rotation, pronation/supination rotation, and flexion/extension rotation or the supracondylar fraction;

(v) mechanically maintaining a desired alignment in the second anatomic orientation, and further including either partially or fully assembling an orthotic on the arm bone region having the supracondylar fracture, and wherein (i) includes placing the orthotic either partially or fully assembled on the arm bone region on the frame.

24. A method according to claim 23 and further including operating a mechanical guidance mechanism on the frame to guide placement of one or more bone fixing devices to maintain the desired alignment in the first and second anatomic orientations.

25. A fracture reduction method for an arm bone region defined by anatomic x-, y-, and z-axes and having a supracondylar the method comprising (i) supporting the arm bone region having the supracondylar fracture on a frame (ii) operating a first reduction mechanism on the frame to apply to the supracondylar fracture a first mechanical force vector that moves the supracondylar fracture into alignment in a first anatomic orientation relative to the anatomic x-axis, (iii) mechanically maintaining a desired alignment in the first anatomic orientation, (iv) operating a second reduction mechanism on the frame to apply to the supracondylar fracture, independent of the application of the first mechanical force vector, a second mechanical force vector that moves the supracondylar fracture into alignment in a second anatomic orientation relative to the anatomic y-axis, (v) mechanically maintaining a desired alignment in the second anatomic orientation, (vi) operating a third reduction mechanism on the frame to apply to the supracondylar fracture, independent of the application of the first and second mechanical force vectors, a third mechanical force vector that moves the supracondylar fracture into alignment in a third anatomic orientation relative to the anatomic z-axis, (vii) mechanically maintaining a desired alignment in the third anatomic orientation, whereby the first mechanical force vector moves the supracondylar fracture into alignment in a first anatomic orientation relative the anatomic x-axis without altering a desired alignment in either the second or third anatomic orientations, whereby the second mechanical force vector moves the supracondylar fracture into alignment in a second anatomic orientation relative the anatomic y-axis without altering a desired alignment in either the first or third anatomic orientations whereby the third mechanical force vector moves the supracondylar fracture into alignment in a first anatomic orientation relative the anatomic z-axis without altering a desired alignment in either the first or second anatomic orientations, and further including either partially or fully assembling an orthotic on the arm bone region having the supracondylar fracture, and wherein (i) includes placing the orthotic either partially or fully assembled on the arm bone region on the frame.

26. A method according to claim 25 and further including operating a mechanical guidance mechanism on the frame to guide placement of one or more bone fixing devices to maintain desired alignments in the first, second, and third anatomic orientations.

27. A system for fixing a bone fracture reduction for use in conjunction with a bone fixing device comprising a frame that is sized and configured to support a body region having bone fracture reduction independent of said bone fixing device, a shuttle body, a guide carried by the shuttle body that defines a path along which a bone fixing device can be placed to fix the bone fracture reduction, a first mount on the shuttle body engaging the frame for moving the guide on the frame relative the bone fracture reduction in a range of positions orientated with the bone fracture reduction in a first plane to guide placement of the bone fixing device in the first plane, the first mount including a mechanism that is sized and configured to mechanically interact with the mount to maintain a desired orientation in the first plane, and a second mount on the shuttle body for moving the guide on the shuttle body relative the bone fracture reduction in a range of positions oriented with the bone fracture reduction within a second plane, different than the first plane, to guide placement of the bone fixing device in the second plane, the second mount including a mechanism that is sized and configured to mechanically interact with the second mount to maintain a desired orientation in the second plane.

28. A system according to claim 27 wherein at least one of the first and second mounts includes a radio-opaque guide parallel to and axially aligned with the path of the bone fixing device in the respective plane.

29. A system according to claim 27 wherein first mount includes a first radio-opaque guide parallel to and axially aligned with the path of the bone fixing device in the first plane, and wherein second mount includes a second radio-opaque guide parallel to and axially aligned with the path of the bone fixing device in the second plane.

30. A system according to claim 27 wherein at least one of the first and second planes comprises a horizontal plane.

31. A system according to claim 27 wherein at least one of the first and second planes comprises a vertical plane.

32. A system according to claim 27 wherein at least one of the first and second planes comprises a plane that intersects a horizontal or vertical plane at an angle.

33. A system according to claim 27 and further including a robotic/computer control system coupled to at least one of the first and second mounts.

34. A method for fixing a bone fracture reduction comprising
supporting a body region having bone fracture reduction on a frame,
providing a guide that defines a path along which a bone fixing device can be placed to fix the bone fracture reduction,
moving the guide on a first mount on the frame relative the bone fracture reduction in a range of positions orientated with the bone fracture reduction in a first plane to guide placement of the bone fixing device in the first plane,
mechanically maintaining a desired orientation in the first plane,
moving the guide on a second mount relative the bone fracture reduction in a range of positions oriented with the bone fracture reduction within a second plane, different than the first plane, to guide placement of the bone fixing device in the second plane,
mechanically maintaining with a desired orientation in the second plane, and
placing the bone fixing device through the guide into the bone fracture reduction to fix the bone fracture reduction.

35. A method according to claim 34
providing at least one radio-opaque guide parallel to and axially aligned with the path of the bone fixing device in at least one the respective planes, and
before placing the bone fixing device through the guide, generating a radiographic image of the radio-opaque guide relative to the bone fracture reduction.

36. A method according to claim 34 wherein at least one of the first and second planes comprises a horizontal plane.

37. A method according to claim 34 wherein at least one of the first and second planes comprises a vertical plane.

38. A method according to claim 34 wherein at least one of the first and second planes comprises a plane that intersects a horizontal or vertical plane at an angle.

39. A system comprising
a frame,
a fracture reduction mechanism on the frame for mechanically reducing a bone fracture,
a fracture fixing guidance mechanism on the frame for mechanically guiding the placement at least one bone fixing device into the reduced bone fracture, and
and further including an orthotic that is sized and configured to be assembled about the bone fracture, and
wherein the frame includes a carrier for the orthotic either partially or fully assembled about the bone region.

40. A system as defined in claim 39
and further including a robotic/computer control system coupled to at least one of the fracture reduction mechanism and the fracture fixing guidance mechanism.

* * * * *